(12) United States Patent
Walsh et al.

(10) Patent No.: US 11,273,057 B2
(45) Date of Patent: Mar. 15, 2022

(54) SPINAL SURGERY INSTRUMENTS, SYSTEMS, AND METHODS

(71) Applicant: GetSet Surgical SA, Epalinges (CH)

(72) Inventors: David Walsh, Reading, MA (US); Ole Stoklund, Lausanne (CH); John Kapitan, Leicester, NC (US)

(73) Assignee: GetSet Surgical SA

( * ) Notice: Subject to any disclaimer, the term of this patent is extended or adjusted under 35 U.S.C. 154(b) by 282 days.

(21) Appl. No.: 16/696,648

(22) Filed: Nov. 26, 2019

(65) Prior Publication Data

US 2021/0153913 A1 May 27, 2021

Related U.S. Application Data

(63) Continuation-in-part of application No. 16/695,952, filed on Nov. 26, 2019.

(51) Int. Cl.
*A61F 2/46* (2006.01)
*A61F 2/44* (2006.01)
(Continued)

(52) U.S. Cl.
CPC ........ *A61F 2/4611* (2013.01); *A61B 17/1631* (2013.01); *A61B 17/17* (2013.01);
(Continued)

(58) Field of Classification Search
CPC .......... A61F 2/44; A61F 2/442; A61F 2/4455; A61F 2/446; A61F 2/4465; A61F 2/447; A61F 2/46; A61F 2/4603; A61F 2/4611
See application file for complete search history.

(56) References Cited

U.S. PATENT DOCUMENTS 2,796,101 A 6/1957 Hasemann
5,364,399 A 11/1994 Lowery et al.
(Continued)

FOREIGN PATENT DOCUMENTS

EP 2391308 B1 12/2015
EP 2688520 B1 9/2017
(Continued)

OTHER PUBLICATIONS

International Search Report and Written Opinion dated Mar. 1, 2021 for corresponding International Application No. PCT/US2020/062421.
(Continued)

*Primary Examiner* — Eric S Gibson
(74) *Attorney, Agent, or Firm* — David Meibos; Maywood IP Law

(57) ABSTRACT

An insertion assembly may include a flexible tool and a DTS guide configured to engage an intervertebral spacer having a fastener channel oriented at a first angle. The DTS guide may include a DTS guide channel oriented at the first angle which may be aligned with the fastener channel. The flexible tool may include a flexible shaft and a working member disposed at a distal end of the flexible shaft. The working member may be received through the DTS guide channel at the first angle. At least a portion of the flexible shaft adjacent the DTS guide member may flex while the working member is received through the DTS guide channel, such that a distal portion of the flexible shaft may be at a greater absolute angle relative to a DTS guide shaft than a proximal portion of the flexible shaft.

20 Claims, 45 Drawing Sheets

(51) Int. Cl.
*A61B 17/16* (2006.01)
*A61B 17/17* (2006.01)
*A61B 17/68* (2006.01)
*A61B 17/84* (2006.01)

(52) U.S. Cl.
CPC ............ *A61B 17/686* (2013.01); *A61B 17/84* (2013.01); *A61F 2/4455* (2013.01)

(56) References Cited

U.S. PATENT DOCUMENTS

| | | | |
|---|---|---|---|
| 5,423,826 A | 6/1995 | Coates et al. | |
| 5,549,612 A | 8/1996 | Yapp et al. | |
| 5,951,558 A | 9/1999 | Fiz | |
| 6,152,927 A | 11/2000 | Farris et al. | |
| 6,193,721 B1 | 2/2001 | Michelson | |
| 6,306,139 B1 | 10/2001 | Fuentes | |
| 6,383,186 B1 | 5/2002 | Michelson | |
| 6,428,542 B1 | 8/2002 | Michelson | |
| 6,558,432 B2 | 5/2003 | Schulte et al. | |
| 6,730,127 B2 | 5/2004 | Michelson | |
| 6,884,242 B2 | 4/2005 | LeHuec et al. | |
| 6,890,335 B2 | 5/2005 | Grabowski et al. | |
| 7,288,094 B2 | 10/2007 | Lindemann et al. | |
| 7,651,497 B2 | 1/2010 | Michelson | |
| 7,674,279 B2 * | 3/2010 | Johnson | A61B 17/8042 606/295 |
| 7,833,226 B2 | 11/2010 | Grabowski et al. | |
| 7,875,062 B2 * | 1/2011 | Lindemann | A61B 17/8042 606/295 |
| 7,901,413 B1 | 3/2011 | Lewis | |
| 7,998,180 B2 | 8/2011 | Erickson et al. | |
| 8,048,075 B2 | 11/2011 | Michelson | |
| 8,066,750 B2 | 11/2011 | Oi et al. | |
| 8,211,148 B2 | 7/2012 | Zhang et al. | |
| 8,216,285 B2 | 7/2012 | Markworth | |
| 8,246,660 B2 | 8/2012 | Boris et al. | |
| 8,262,705 B2 | 9/2012 | Bray | |
| 8,277,493 B2 | 10/2012 | Farris et al. | |
| 8,328,872 B2 * | 12/2012 | Duffield | A61F 2/44 623/17.16 |
| 8,348,982 B2 | 1/2013 | Baynham et al. | |
| 8,419,795 B2 | 4/2013 | Sweeney | |
| 8,439,593 B2 | 5/2013 | Slater et al. | |
| 8,480,717 B2 | 7/2013 | Michelson | |
| 8,523,920 B2 | 9/2013 | Gause et al. | |
| 8,562,655 B2 | 10/2013 | Butler | |
| 8,591,556 B2 | 11/2013 | Hansell et al. | |
| 8,613,761 B2 | 12/2013 | Lindemann et al. | |
| 8,617,222 B2 | 12/2013 | Shipp et al. | |
| 8,672,984 B2 | 3/2014 | Lindemann et al. | |
| 8,696,721 B2 | 4/2014 | Blain | |
| 8,795,341 B2 | 8/2014 | Walker et al. | |
| 8,795,373 B2 * | 8/2014 | Jones | A61B 17/8042 623/17.16 |
| 8,858,603 B1 | 10/2014 | Zufelt | |
| 8,858,604 B2 | 10/2014 | Biyani et al. | |
| 8,882,843 B2 | 11/2014 | Michelson | |
| 8,932,335 B2 | 1/2015 | Humphreys | |
| 8,940,030 B1 | 1/2015 | Stein et al. | |
| 8,979,910 B2 | 3/2015 | Stanaford et al. | |
| 9,005,288 B2 | 4/2015 | McCormack et al. | |
| 9,005,293 B2 | 4/2015 | Moskowitz et al. | |
| 9,017,412 B2 * | 4/2015 | Wolters | A61F 2/442 623/17.16 |
| 9,028,498 B2 | 5/2015 | Hershgold et al. | |
| 9,107,710 B1 | 8/2015 | Swann | |
| 9,114,023 B2 | 8/2015 | Kana et al. | |
| 9,119,682 B2 | 9/2015 | Stoll et al. | |
| 9,155,572 B2 | 10/2015 | Altarac et al. | |
| 9,179,952 B2 | 11/2015 | Biedermann et al. | |
| 9,180,020 B2 | 11/2015 | Gause et al. | |
| 9,186,189 B2 | 11/2015 | Campbell et al. | |
| 9,220,548 B2 | 12/2015 | Duong et al. | |
| 9,241,749 B2 | 1/2016 | Lombardo et al. | |
| 9,265,546 B2 | 2/2016 | Blain | |
| 9,277,943 B2 | 3/2016 | Holly et al. | |
| 9,326,803 B2 | 5/2016 | Humphreys | |
| 9,351,768 B2 | 5/2016 | Rinner et al. | |
| 9,364,340 B2 * | 6/2016 | Lawson | A61F 2/4455 |
| 9,381,093 B1 | 7/2016 | Morris et al. | |
| 9,402,735 B2 | 8/2016 | McDonough et al. | |
| 9,414,935 B2 | 8/2016 | McDonough et al. | |
| 9,421,055 B2 | 8/2016 | Suh | |
| 9,445,851 B2 | 9/2016 | Walker et al. | |
| 9,451,951 B2 | 9/2016 | Sullivan et al. | |
| 9,468,534 B2 | 10/2016 | Garber et al. | |
| 9,622,875 B2 | 4/2017 | Moskowitz et al. | |
| 9,744,052 B2 | 8/2017 | Moskowitz et al. | |
| 9,814,601 B2 | 11/2017 | Moskowitz et al. | |
| 9,826,973 B2 | 11/2017 | Graul et al. | |
| 9,867,719 B2 | 1/2018 | Moskowitz et al. | |
| 9,889,022 B2 | 2/2018 | Moskowitz et al. | |
| 9,937,060 B2 | 4/2018 | Fuhrer et al. | |
| 9,980,826 B2 * | 5/2018 | Martynova | A61F 2/442 |
| 2004/0133280 A1 | 7/2004 | Trieu | |
| 2006/0293668 A1 | 12/2006 | May et al. | |
| 2007/0123995 A1 | 5/2007 | Thelen et al. | |
| 2008/0033440 A1 | 2/2008 | Moskowitz et al. | |
| 2010/0016901 A1 | 1/2010 | Robinson | |
| 2010/0057206 A1 * | 3/2010 | Duffield | A61F 2/30771 623/17.16 |
| 2010/0292696 A1 | 11/2010 | Chantelot et al. | |
| 2012/0071933 A1 | 3/2012 | DeRidder | |
| 2012/0150301 A1 * | 6/2012 | Gamache | A61F 2/447 623/17.16 |
| 2012/0158068 A1 | 6/2012 | Humphreys | |
| 2012/0277803 A1 | 11/2012 | Remesh et al. | |
| 2013/0197588 A1 | 8/2013 | Abdou | |
| 2014/0012384 A1 | 1/2014 | Kana et al. | |
| 2014/0046377 A1 | 2/2014 | Hansell et al. | |
| 2014/0180422 A1 * | 6/2014 | Klimek | A61F 2/30744 623/17.16 |
| 2014/0214081 A1 | 7/2014 | Schwab et al. | |
| 2014/0257487 A1 * | 9/2014 | Lawson | A61B 17/8042 623/17.16 |
| 2014/0288655 A1 | 9/2014 | Parry et al. | |
| 2014/0336770 A1 * | 11/2014 | Petersheim | A61F 2/447 623/17.16 |
| 2014/0371859 A1 * | 12/2014 | Petersheim | A61F 2/447 623/17.16 |
| 2015/0025635 A1 | 1/2015 | Laubert | |
| 2015/0066096 A1 | 3/2015 | Bush, Jr. et al. | |
| 2015/0201982 A1 | 7/2015 | Altarac et al. | |
| 2016/0022335 A1 | 1/2016 | Humphreys | |
| 2016/0038309 A1 | 2/2016 | Doyle | |
| 2016/0128737 A1 | 5/2016 | Coric et al. | |
| 2016/0128746 A1 | 5/2016 | Dunaway | |
| 2016/0151171 A1 * | 6/2016 | Mozeleski | A61B 17/7059 623/17.16 |
| 2016/0166396 A1 | 6/2016 | McClintock | |
| 2016/0213410 A1 | 7/2016 | Humphreys | |
| 2016/0220388 A1 * | 8/2016 | Flores | A61F 2/4611 |
| 2016/0228156 A1 | 8/2016 | Morris et al. | |
| 2016/0228165 A1 | 8/2016 | Walker et al. | |
| 2016/0235448 A1 * | 8/2016 | Seex | A61F 2/4611 |
| 2016/0250037 A1 * | 9/2016 | Duffield | A61B 17/8042 623/17.16 |
| 2016/0270832 A1 | 9/2016 | Bush, Jr. et al. | |
| 2016/0310295 A1 * | 10/2016 | Reed | A61F 2/4611 |
| 2016/0324554 A1 | 11/2016 | Suh | |
| 2017/0049579 A1 | 2/2017 | Quinlan et al. | |
| 2017/0189204 A1 * | 7/2017 | Riemhofer | A61F 2/4611 |
| 2018/0049756 A1 * | 2/2018 | Livorsi | A61F 2/4611 |
| 2018/0055651 A1 | 3/2018 | Moskowitz et al. | |
| 2018/0318099 A1 * | 11/2018 | Altarac | A61B 17/8042 |
| 2018/0318100 A1 | 11/2018 | Altarac et al. | |
| 2019/0133778 A1 | 5/2019 | Johnston | |
| 2021/0153879 A1 * | 5/2021 | Walsh | A61B 17/1631 |
| 2021/0153913 A1 * | 5/2021 | Walsh | A61F 2/447 |
| 2021/0154022 A1 * | 5/2021 | Walsh | A61F 2/4611 |

(56) References Cited

U.S. PATENT DOCUMENTS

FOREIGN PATENT DOCUMENTS

| JP | 2016524988 A    | 8/2016 |
| -- | --------------- | ------ |
| WO | WO2007136452 A3 | 7/2008 |
| WO | WO2010054181    | 5/2010 |
| WO | WO2010078488 A2 | 7/2010 |
| WO | WO2013098828 A1 | 7/2013 |
| WO | WO2014094551 A1 | 6/2014 |
| WO | WO2015025108 A1 | 2/2015 |
| WO | WO2015051119 A1 | 4/2015 |

OTHER PUBLICATIONS

International Search Report and Written Opinion dated Apr. 6, 2021 for corresponding International Application No. PCT/US2020/062422.
International Search Report and Written Opinion dated Mar. 3, 2021 for corresponding International Application No. PCT/US2020/062424.

* cited by examiner

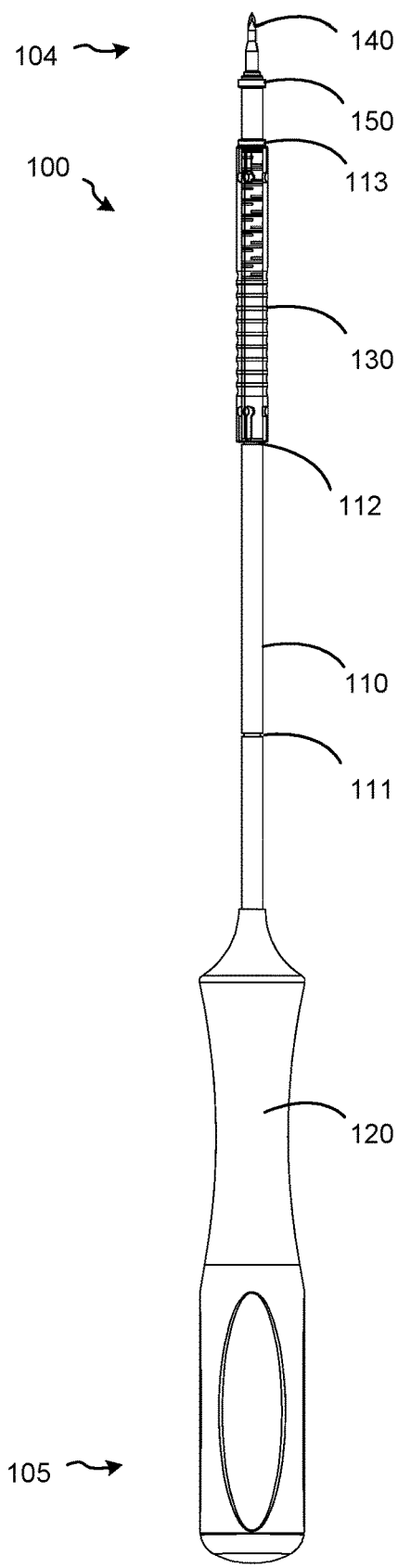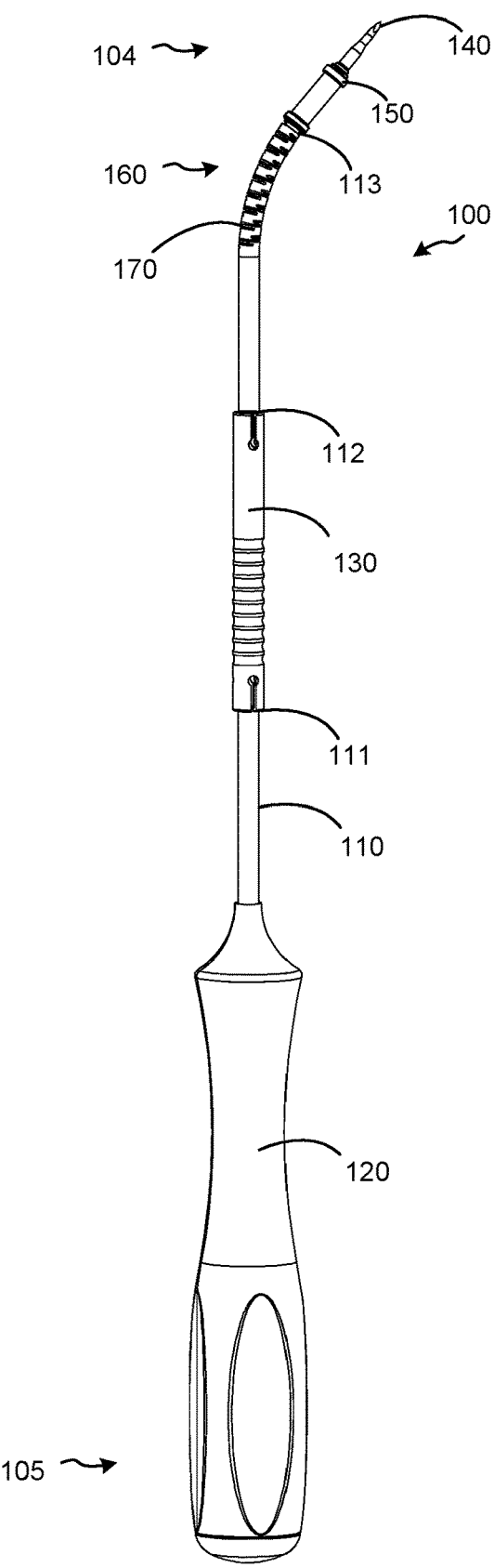
FIG. 1A
FIG. 1B

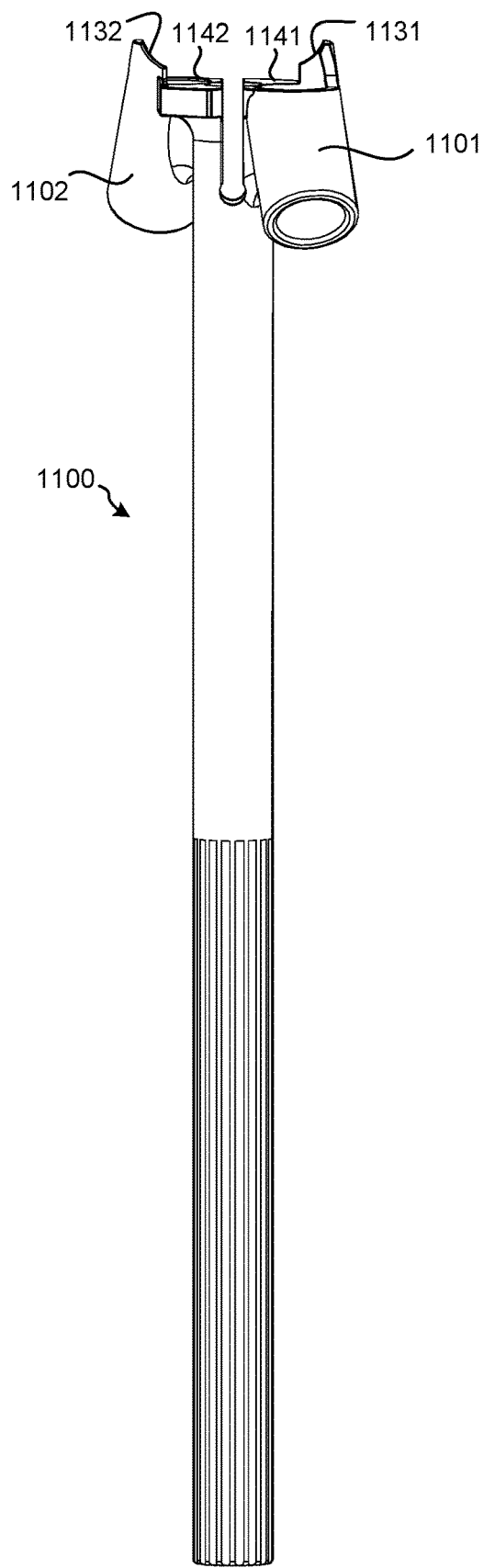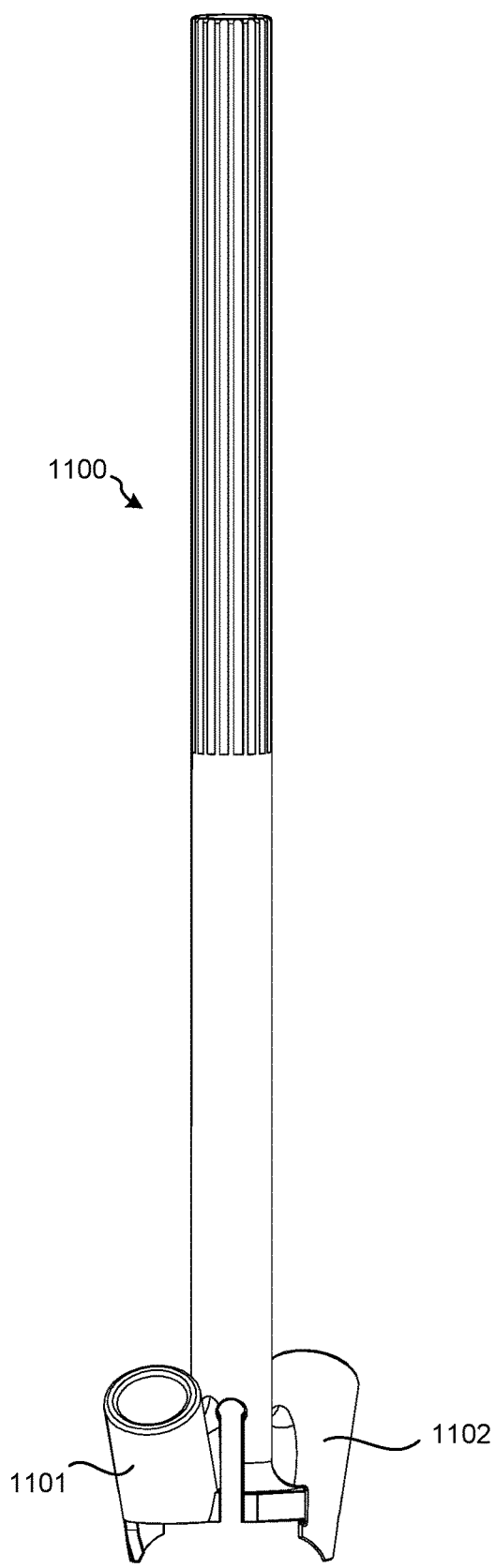
FIG. 11C    FIG. 11D

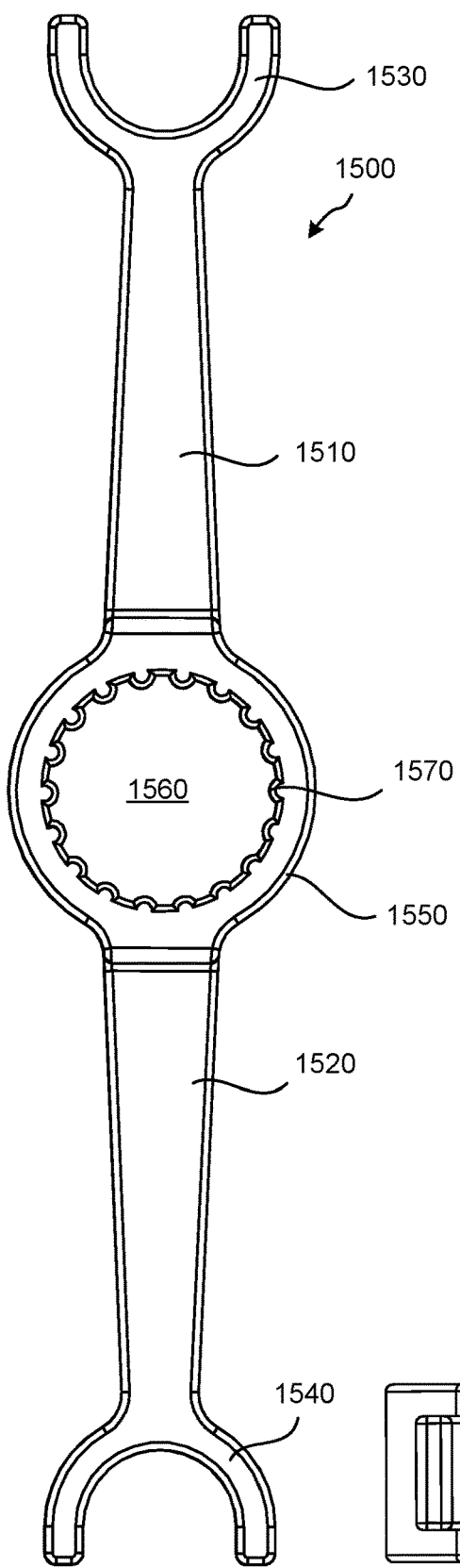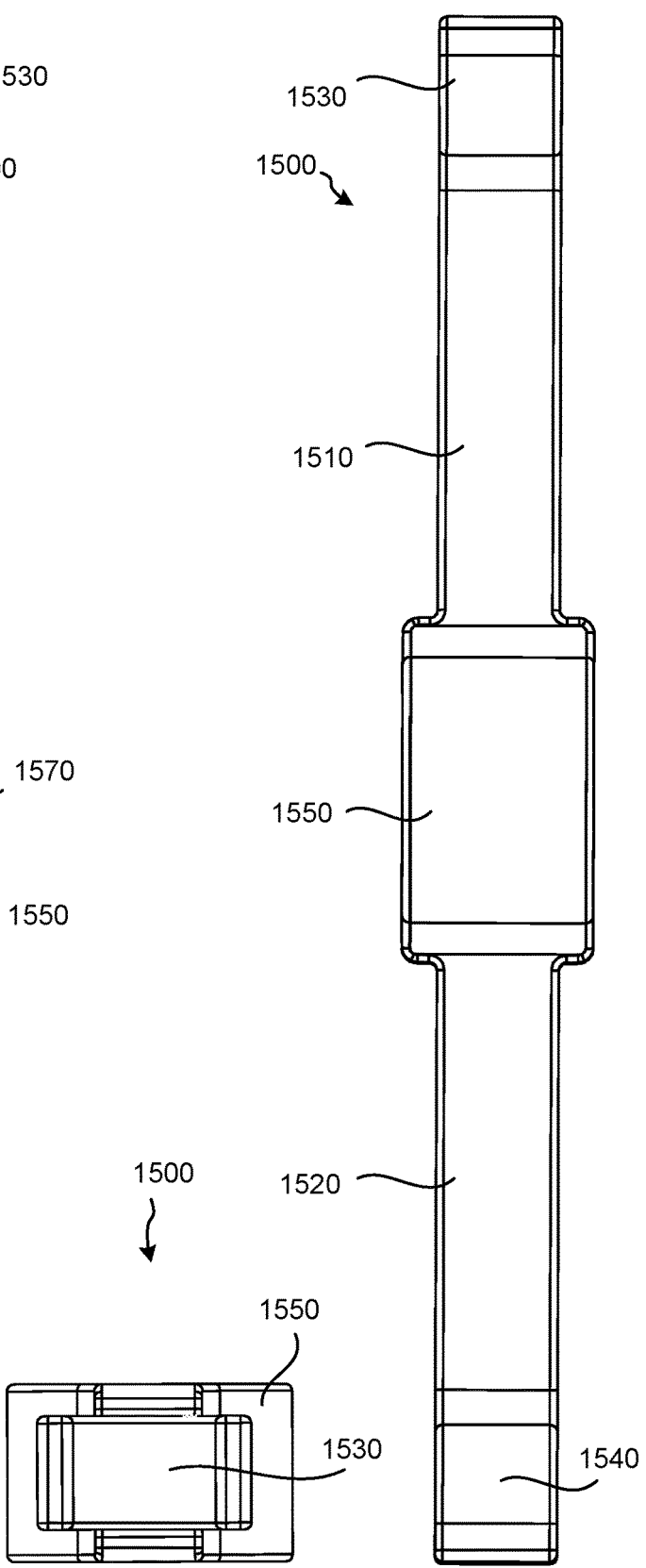
FIG. 15B  FIG. 15C  FIG. 15D

SPINAL SURGERY INSTRUMENTS, SYSTEMS, AND METHODS

CROSS-REFERENCE TO RELATED APPLICATIONS

This application is a continuation-in-part of U.S. patent application Ser. No. 16/695,952 entitled "SPINAL SURGERY DEVICES, SYSTEMS, AND METHODS," which was filed on Nov. 26, 2019, the disclosure of which is incorporated herein by reference in its entirety.

TECHNICAL FIELD

The present disclosure relates to surgical instruments, systems, and methods. More specifically, the present disclosure relates to improved surgical instruments, systems, and methods for implanting intervertebral spacers between adjacent vertebral bodies in a patient.

BACKGROUND

Spinal fixation procedures utilizing intervertebral spacers can be used to correct spinal conditions such as degenerative disc disease, spondylolisthesis, spinal deformities, or other spinal conditions through minimally invasive or invasive spinal surgery. For example, intervertebral discs can degenerate or otherwise become damaged over time. In some instances, an intervertebral spacer can be positioned within a space previously occupied by a disc between adjacent vertebral bodies. Such intervertebral spacers can help maintain a desired spacing between adjacent vertebrae and/or promote fusion between adjacent vertebrae. The use of bone graft and/or other materials within an intervertebral spacer can facilitate the fusion of adjacent vertebral bodies. One or more bone screws may also be utilized to help stabilize the intervertebral spacer during the fusion process.

During implantation, an intervertebral spacer may be provisionally placed between two vertebral bodies. One or more bone tunnels may then be formed within the vertebral bodies via an awl tool projecting through angled fastener channels of the intervertebral spacer. Bone screws may then be placed through the fastener channels and driven into the bone tunnels formed in the vertebral bodies via a suitable driver tool in order to secure the intervertebral spacer between the vertebral bodies.

However, traditional awl tools and driver tools typically include straight shafts that require a larger surgical incision (or additional surgical incisions) to be formed in the patient's tissues in order to implant the intervertebral spacer with these traditional awl tools and driver tools. Accordingly, a need exists for improved surgical instruments, systems, and methods.

SUMMARY

The various instruments, systems, and methods of the present disclosure have been developed in response to the present state of the art, and in particular, in response to the problems and needs in the art that have not yet been fully solved by currently available surgical instruments, systems, and methods for implanting intervertebral spacers between adjacent vertebral bodies of a patient.

According to some embodiments, an intervertebral spacer insertion system may include an intervertebral spacer and an insertion assembly comprising an inserter tool, a Drill, Tap, and Screw guide (hereinafter, "DTS guide"), and a flexible tool. The intervertebral spacer may include a superior surface configured to engage a superior vertebral body, an inferior surface configured to engage an inferior vertebral body, and a proximal surface. The proximal surface may include a first fastener channel configured to receive a first fastener, the first fastener channel oriented to pass through the proximal and superior surfaces of the intervertebral spacer at a first angle, a second fastener channel configured to receive a second fastener, the second fastener channel oriented to pass through the proximal and inferior surfaces of the intervertebral spacer at a second angle, and a locking member channel intermediate the first and second fastener channels. The locking member channel may include a first engagement feature formed therein. The inserter tool may include an inserter tool shaft and a second engagement feature formed on a distal end of the inserter tool shaft. The second engagement feature may be configured to engage the first engagement feature in order to removably couple the intervertebral spacer with the inserter tool. The DTS guide may include a DTS guide shaft and a DTS guide shaft lumen passing through the DTS guide shaft, the DTS guide shaft lumen configured to receive the inserter tool shaft therein to slidably couple the DTS guide with the inserter tool. The DTS guide may also include a first DTS guide member having a first DTS guide channel configured to receive the first fastener at the first angle to guide the first fastener into the first fastener channel of the intervertebral spacer. The DTS guide may further include a second DTS guide member having a second DTS guide channel configured to receive the second fastener at the second angle to guide the second fastener into the second fastener channel of the intervertebral spacer. The DTS guide may additionally include a first DTS guide wing proximate the first DTS guide member, the first DTS guide wing configured to abut against a first surface of the intervertebral spacer, and a second DTS guide wing proximate the second DTS guide member, the second DTS guide wing configured to abut against a second surface of the intervertebral spacer. The first and second DTS guide wings may be configured to align the first and second DTS guide channels with respect to the first and second fastener channels, independently of any additional apertures or recesses formed in the intervertebral spacer, in order to respectively guide the first and second fasteners through the first and second DTS guide channels and into the first and second fastener channels of the intervertebral spacer. The flexible tool may include a flexible shaft and a working member disposed at a distal end of the flexible shaft. The working member may be configured to be received through the first DTS guide channel at the first angle and the second DTS guide channel at the second angle. At least a portion of the flexible shaft adjacent the first or second DTS guide members may be configured to flex while the working member is received through the first or second DTS guide channels. The working member that is received through the first or second DTS guide channels at the first or second angles may be at a greater absolute angle relative to the DTS guide shaft than a proximal portion of the flexible shaft.

In some embodiments of the intervertebral spacer insertion system, the proximal portion of the flexible shaft may be substantially parallel to the DTS guide shaft while the working member is received through the first or second DTS guide channels at the first or second angles.

In some embodiments of the intervertebral spacer insertion system, the flexible shaft may comprise a plurality of slots formed in at least a portion of the flexible shaft and the plurality of slots may be configured to permit at least a portion of the flexible shaft to flex away from a longitudinal axis of the flexible shaft.

In some embodiments of the intervertebral spacer insertion system, the proximal portion of the flexible shaft may remain substantially parallel to the DTS guide shaft as the flexible shaft is rotated about the longitudinal axis.

In some embodiments the intervertebral spacer insertion system may further comprise a U-support tool coupled to the DTS guide shaft and configured to guide the flexible shaft as it is rotated about the longitudinal axis in order to maintain the proximal portion of the flexible shaft substantially parallel to the DTS guide shaft as the flexible shaft is rotated about the longitudinal axis.

In some embodiments of the intervertebral spacer insertion system, the flexible tool further may comprise a sleeve slidably coupled to the flexible shaft and configured to move between a locked position and an unlocked position. In the locked position, the sleeve may prevent flexion of the flexible shaft. In the unlocked position, the sleeve may allow flexion of the flexible shaft. The sleeve may comprise a first ridge disposed at a proximal end of the sleeve and a second ridge disposed at a distal end of the sleeve. The flexible shaft may comprise a first notch, a second notch, and a third notch. In the unlocked position, the first ridge may be received within the first notch and the second ridge may be received within the second notch. In the locked position, the first ridge may be received within the second notch and the second ridge may be received within the third notch.

In some embodiments of the intervertebral spacer insertion system, the working member may comprise at least one of a drill tip, an awl tip, and a driver engagement feature.

In other embodiments, an insertion assembly configured to insert an intervertebral spacer between two vertebral bodies of a patient may include a DTS guide and a flexible tool. The intervertebral spacer may include a superior surface configured to engage a superior vertebral body, an inferior surface configured to engage an inferior vertebral body, and a peripheral wall extending from the superior surface to the inferior surface. The peripheral wall may include a fastener channel configured to receive a fastener, the fastener channel oriented to pass through the peripheral wall and the superior or inferior surface of the intervertebral spacer at a first angle. The DTS guide may include a DTS guide shaft, a DTS guide member coupled to a distal end of the DTS guide shaft, and a DTS guide channel formed through the DTS guide member at the first angle relative to the DTS guide shaft and configured to receive the fastener therethrough. The DTS guide may be configured to engage the intervertebral spacer and align the DTS guide channel with the fastener channel at the first angle. The flexible tool may include a flexible shaft and a working member disposed at a distal end of the flexible shaft. The working member may be configured to be received through the DTS guide channel at the first angle. At least a portion of the flexible shaft adjacent the DTS guide member may be configured to flex while the working member is received through the DTS guide channel, and a distal portion of the flexible shaft may be at a greater absolute angle relative to the DTS guide shaft than a proximal portion of the flexible shaft.

In some embodiments of the insertion assembly, the proximal portion of the flexible shaft may be substantially parallel to the DTS guide shaft while the working member is received through the DTS guide channel at the first angle.

In some embodiments of the insertion assembly, the flexible shaft may comprise a plurality of slots formed in at least a portion of the flexible shaft. The plurality of slots may be configured to permit at least a portion of the flexible shaft to flex away from a longitudinal axis of the flexible shaft.

In some embodiments of the insertion assembly, the proximal portion of the flexible shaft may remain substantially parallel to the DTS guide shaft as the flexible shaft is rotated about the longitudinal axis.

In some embodiments the insertion assembly may further comprise a U-support tool coupled to the DTS guide shaft and configured to guide the flexible shaft as it is rotated about the longitudinal axis in order to maintain the proximal portion of the flexible shaft substantially parallel to the DTS guide shaft as the flexible shaft is rotated about the longitudinal axis.

In some embodiments of the insertion assembly, the flexible tool may further comprise a sleeve slidably coupled to the flexible shaft and configured to move between a locked position and an unlocked position. In the locked position, the sleeve may prevent flexion of the flexible shaft. In the unlocked position, the sleeve may allow flexion of the flexible shaft.

In some embodiments of the insertion assembly, the sleeve may comprise a first ridge disposed at a proximal end of the sleeve, and a second ridge disposed at a distal end of the sleeve. The flexible shaft may comprise a first notch, a second notch, and a third notch. In the unlocked position, the first ridge may be received within the first notch and the second ridge may be received within the second notch. In the locked position, the first ridge may be received within the second notch, and the second ridge may be received within the third notch.

In some embodiments of the insertion assembly, the working member may comprise at least one of a drill tip, an awl tip, and a driver engagement feature.

In some embodiments the intervertebral spacer may further comprises a locking member channel adjacent the fastener channel and comprising a first engagement feature. The insertion assembly may further comprise an inserter tool. The inserter tool may comprise an inserter tool shaft and a second engagement feature formed on a distal end of the inserter tool shaft. The second engagement feature may be configured to engage the first engagement feature of the locking member channel to removably couple the intervertebral spacer with the inserter tool. The DTS guide may further comprise a DTS guide shaft lumen passing through the DTS guide shaft and configured to receive the inserter tool shaft therein to slidably couple the DTS guide to the inserter tool. The DTS guide may further comprise a DTS guide wing proximate the DTS guide member, the DTS guide wing configured to abut against a surface of the peripheral wall and align the DTS guide channel with respect to the fastener channel in order to guide the fastener through the DTS guide channel and into the fastener channel of the intervertebral spacer.

In yet other embodiments, a method of inserting an intervertebral spacer between two vertebral bodies of a patient may include orienting a DTS guide with respect to the intervertebral spacer. The intervertebral spacer may include a superior surface configured to engage a superior vertebral body, an inferior surface configured to engage an inferior vertebral body, and a peripheral wall extending from the superior surface to the inferior surface. The peripheral wall may include a fastener channel configured to receive a fastener, the fastener channel oriented to pass through the peripheral wall and the superior or inferior surface of the intervertebral spacer at a first angle. The method may include engaging a DTS guide with the intervertebral spacer. The method may also include aligning a DTS guide channel of the DTS guide with respect to the fastener channel of the intervertebral spacer via a DTS guide wing coupled to the DTS guide. The DTS guide wing may be configured to abut against a surface of the peripheral wall and align the DTS guide channel with respect to the fastener channel at the first angle in order to guide the fastener through the DTS guide channel and into the fastener channel of the intervertebral spacer. The method may also include inserting a working member (disposed at a distal end of a flexible shaft of a flexible tool) through the DTS guide channel at the first angle. The method may additionally include applying a force to the flexible shaft to cause at least a portion of the flexible shaft adjacent the DTS guide channel to flex, such that a distal portion of the flexible shaft is at a greater absolute angle relative to a DTS guide shaft than a proximal portion of the flexible shaft.

In some embodiments, the method may further comprise engaging the distal portion of the flexible shaft against a U-support member coupled to the DTS guide shaft and rotating the flexible shaft about a longitudinal axis of the flexible shaft, while applying a force to maintain the distal portion of the flexible shaft against the U-support member as the flexible shaft is rotated, such that the distal portion of the flexible shaft remains substantially parallel to the DTS guide shaft as the flexible shaft is rotated.

In some embodiments, the working member may comprise an awl tip and the method may further comprise drilling a bone tunnel in a vertebral body of the patient with the awl tip guided through the DTS guide channel, through the fastener channel of the intervertebral spacer, and into the vertebral body of the patient.

In some embodiments the working member may comprise a driver engagement feature and the method may further comprise driving a bone screw into a vertebral body of the patient with the driver engagement feature coupled to the bone screw and guided through the DTS guide channel and into the fastener channel of the intervertebral spacer.

These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

FIG. 1A is a side view of a flexible awl tool, according to an embodiment of the present disclosure;

FIG. 1B is a side view of the flexible awl tool of FIG. 1A in flexion;

FIG. 11C is a top view of the DTS guide of FIG. 11A;

FIG. 11D is a bottom view of the DTS guide of FIG. 11A;

FIG. 15B is a front side view of the U-support tool of FIG. 15A;

FIG. 15C is a top view of the U-support tool of FIG. 15A;

FIG. 15D is a left side view of the U-support tool of FIG. 15A;

Figure 1C:
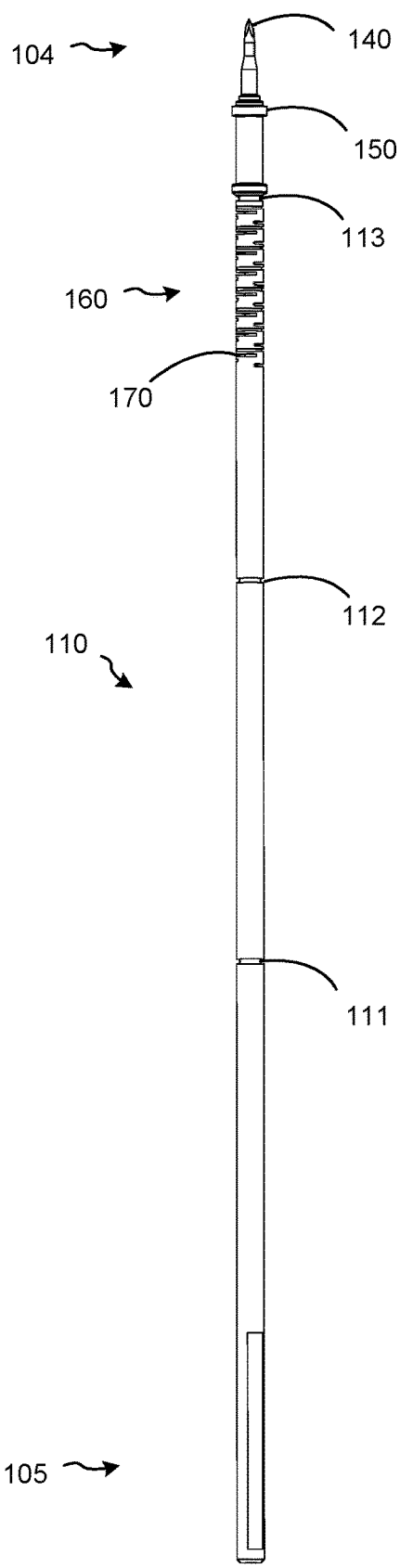
FIG. 1C is a side view of a flexible awl shaft of the flexible awl tool of FIG. 1A.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application, but is merely representative of exemplary embodiments of the present disclosure.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1D:
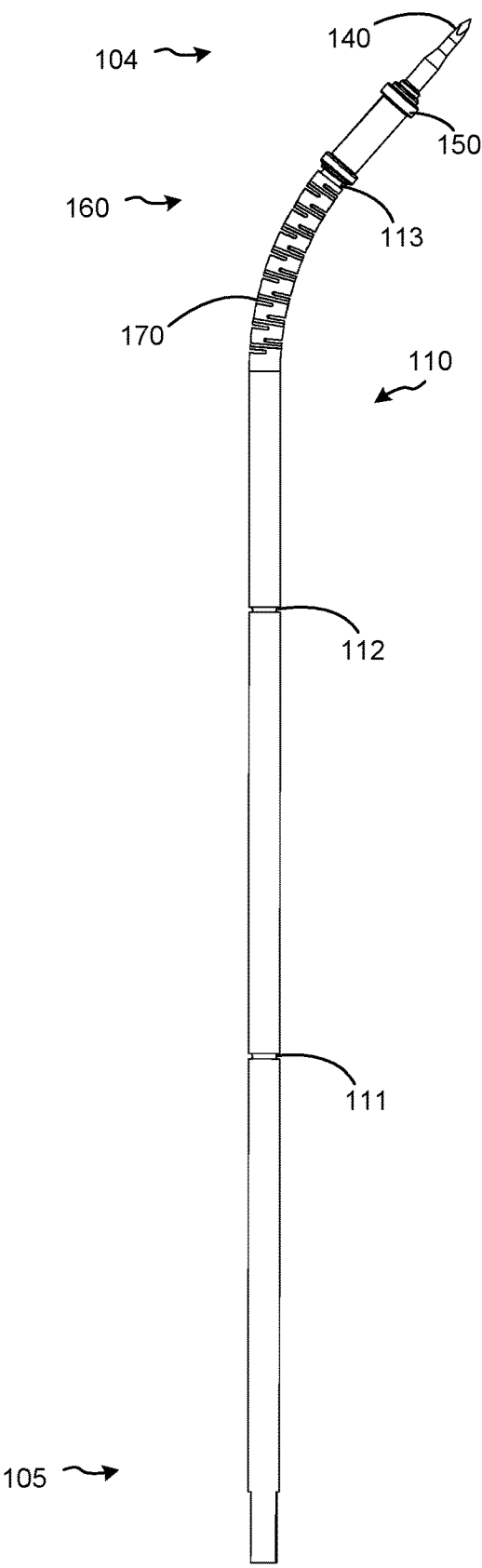
FIG. 1D is a side view of the flexible awl shaft of FIG. 1C in flexion.
Figure 1E:
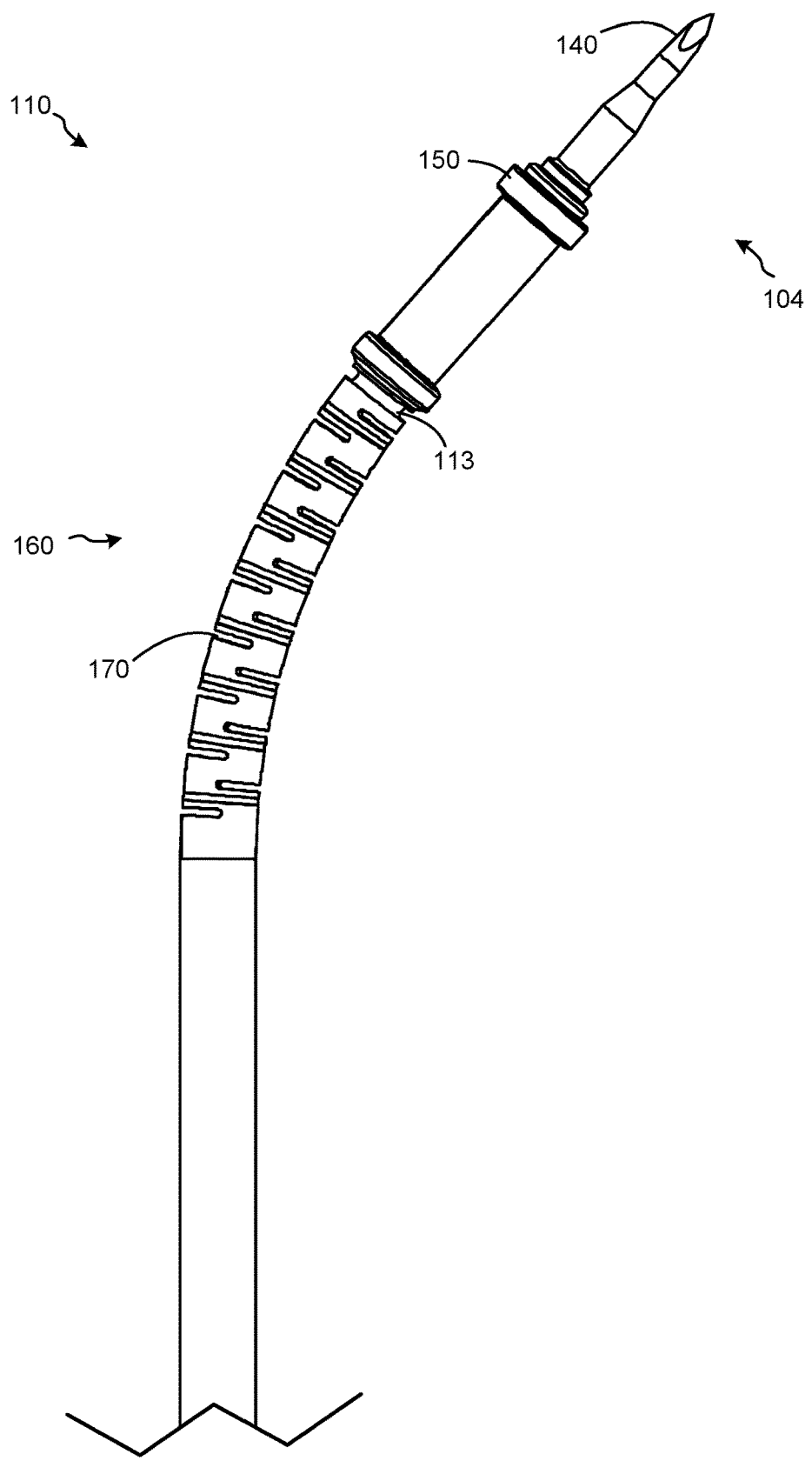
FIG. 1E is a close up view of a distal end of the flexible awl shaft of FIG. 1D.
Figure 1F:
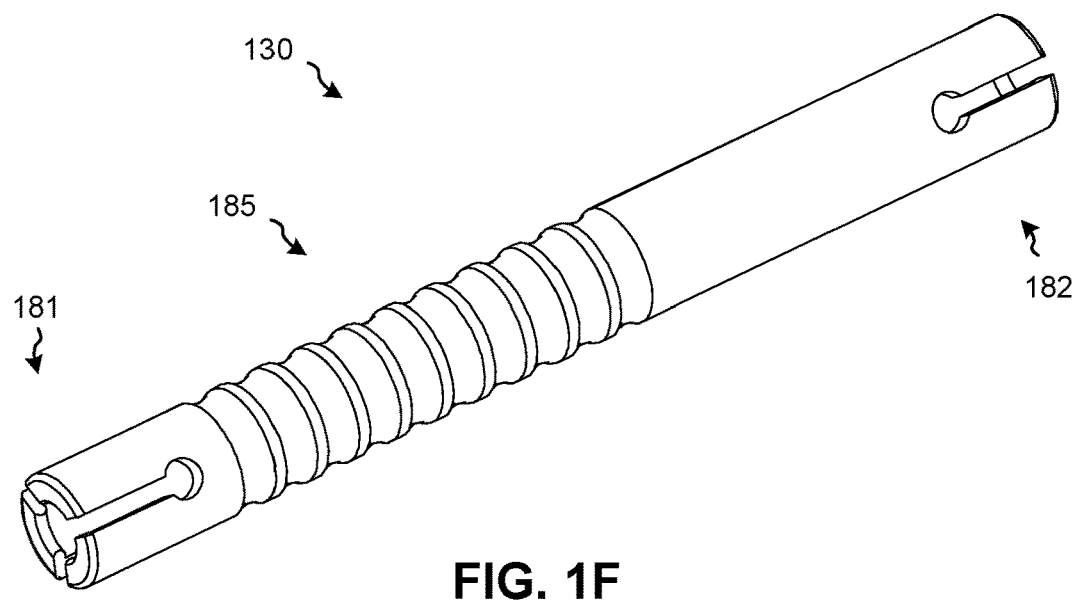
FIG. 1F is a perspective view of an awl sleeve of the flexible awl tool of FIG. 1A.
Figure 1G:
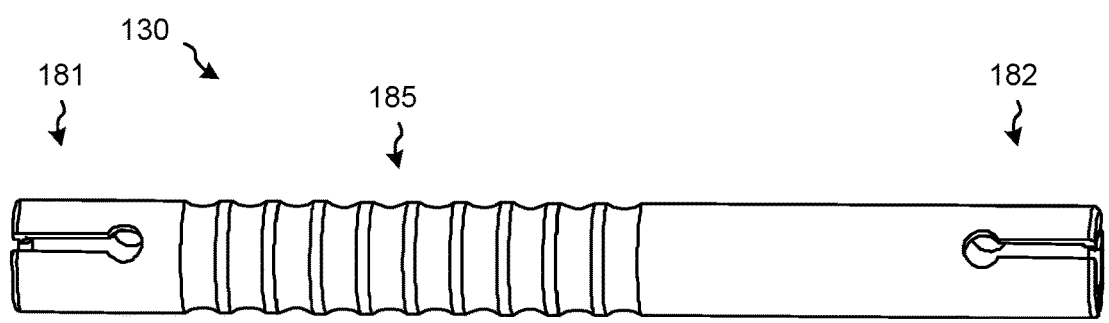
FIG. 1G is a side view of the awl sleeve of FIG. 1F.
Figure 1H:
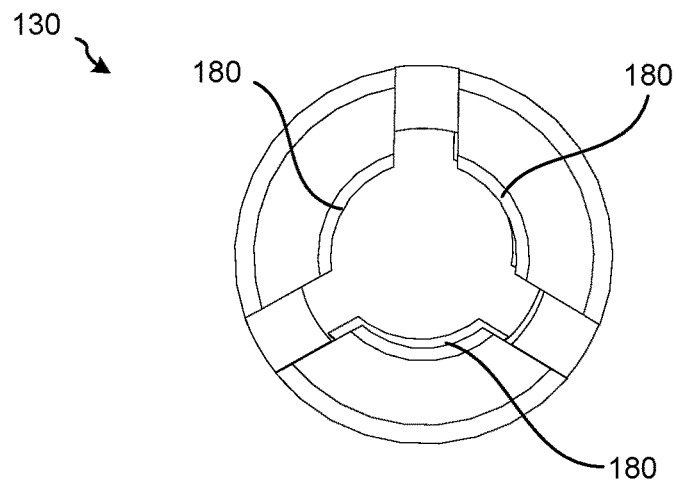
FIG. 1H is an end view of the awl sleeve of FIG. 1F.
Figure 1I:
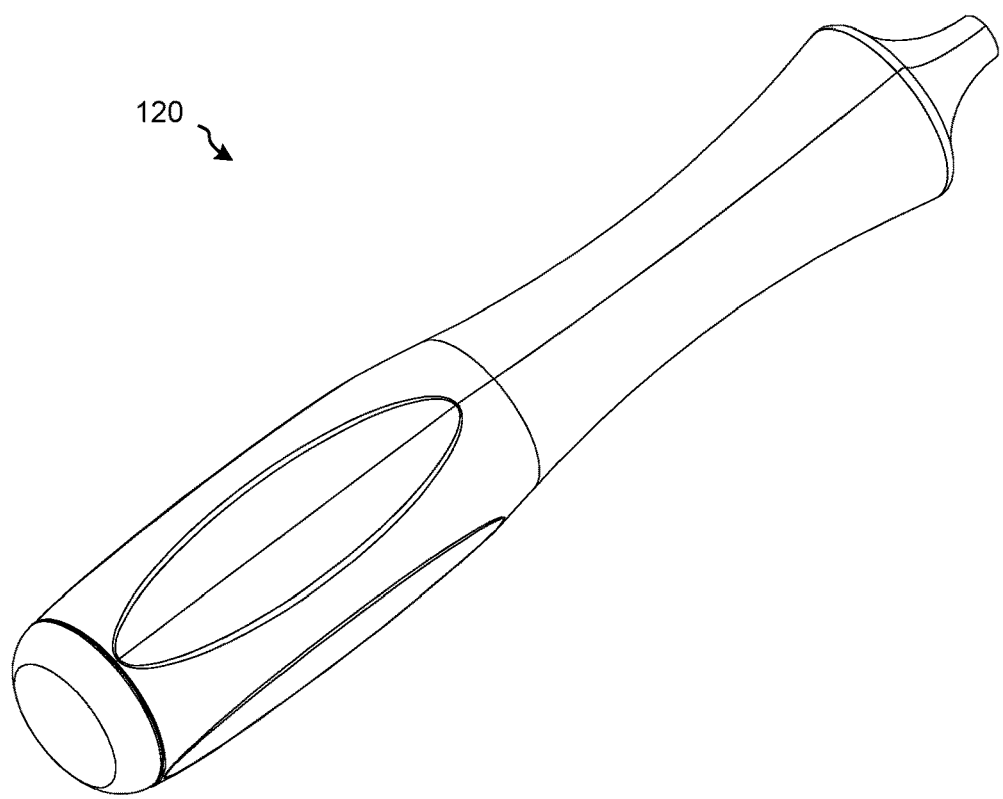
FIG. 1I is a perspective top view of an awl handle of the flexible awl tool of FIG. 1A.
Figure 1J:
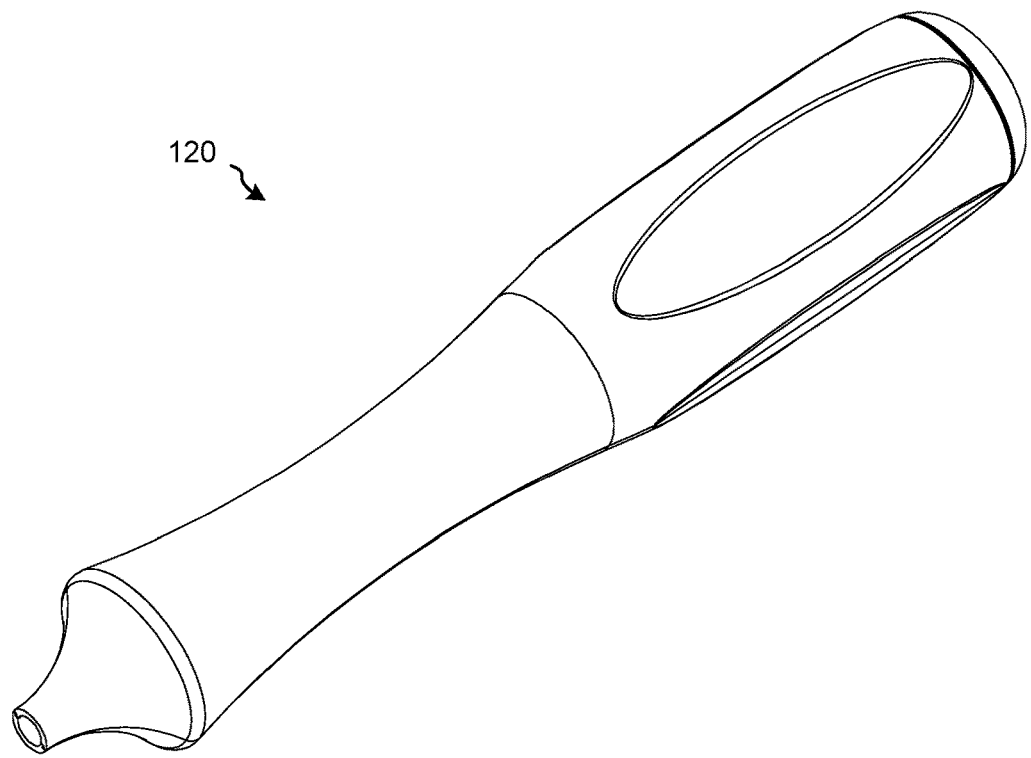
FIG. 1J is a perspective bottom view of the awl handle of FIG. 1I.

FIGS. 1A-1J illustrate various views of a flexible awl tool 100 and its components, according to an embodiment of the present disclosure. Specifically, FIG. 1A is a side view of the flexible awl tool 100; FIG. 1B is a side view of the flexible awl tool 100 in flexion; FIG. 1C is a side view of a flexible awl shaft 110 of the flexible awl tool 100; FIG. 1D is a side view of the flexible awl shaft 110 in flexion; FIG. 1E is a close up view of a distal end 104 of the flexible awl shaft 110; FIG. 1F is a perspective view of an awl sleeve 130 of the flexible awl tool 100; FIG. 1G is a side view of the awl sleeve 130; FIG. 1H is an end view of the awl sleeve 130; FIG. 1I is a perspective top view of an awl handle 120 of the flexible awl tool 100; and FIG. 1J is a perspective bottom view of the awl handle 120.

The flexible awl tool 100 may include a proximal end 105, a distal end 104, a flexible awl shaft 110, an awl handle 120, an awl sleeve 130, an awl depth stop ring 150, and a working member comprising an awl tip or a drill tip or 140. The awl sleeve 130 may translate in the proximal and distal directions along the flexible awl shaft 110 in order to selectively prevent or allow the flexible awl shaft 110 from bending at the flexible portion 160 of the flexible awl shaft 110. For example, FIG. 1A shows the awl sleeve 130 translated distally in order to provide rigid support to the flexible awl shaft 110 over the flexible portion 160 of the flexible awl shaft 110. FIG. 1B shows the awl sleeve 130 translated proximally in order to allow the flexible portion 160 of the flexible awl shaft 110 the freedom to bend and flex. The flexible awl shaft 110 may also include a first notch 111, a second notch 112, and a third notch 113, which may interact with corresponding protrusions 180 formed on a proximal end 181 and a distal end 182 of the awl sleeve 130 to selectively retain the awl sleeve 130 in a locked position (e.g., when the awl sleeve 130 is translated proximally) and an unlocked position (e.g., when the awl sleeve 130 is translated distally). A tactile and/or audible "click" may be felt and/or heard by the surgeon when the awl sleeve 130 reaches the unlocked and/or locked positions. In at least one embodiment, the proximal and distal ends 181, 182 of the awl sleeve 130 may also comprise collet structures that provide resiliency to the protrusions 180 of the awl sleeve 130 to allow them to selectively engage and disengage with the first, second, and third notches 111, 112, 113 of the flexible awl shaft 110. The awl sleeve 130 may also include a grip feature 185 to facilitate translation of the awl sleeve 130 between the locked and unlocked positions. In at least one embodiment, the flexible portion 160 of the flexible awl shaft 110 may comprise a plurality of slots 170 formed in the flexible awl shaft 110 and configured to allow the flexible portion 160 of the flexible awl shaft 110 to bend and flex away from a longitudinal axis of the flexible awl shaft 110. However, it will be understood that any suitable structure or arrangement may also be utilized to achieve flexion in the flexible awl shaft 110. Operation of the flexible awl tool 100 will be discussed in more detail below with respect to FIG. 17.

Figure 2A:
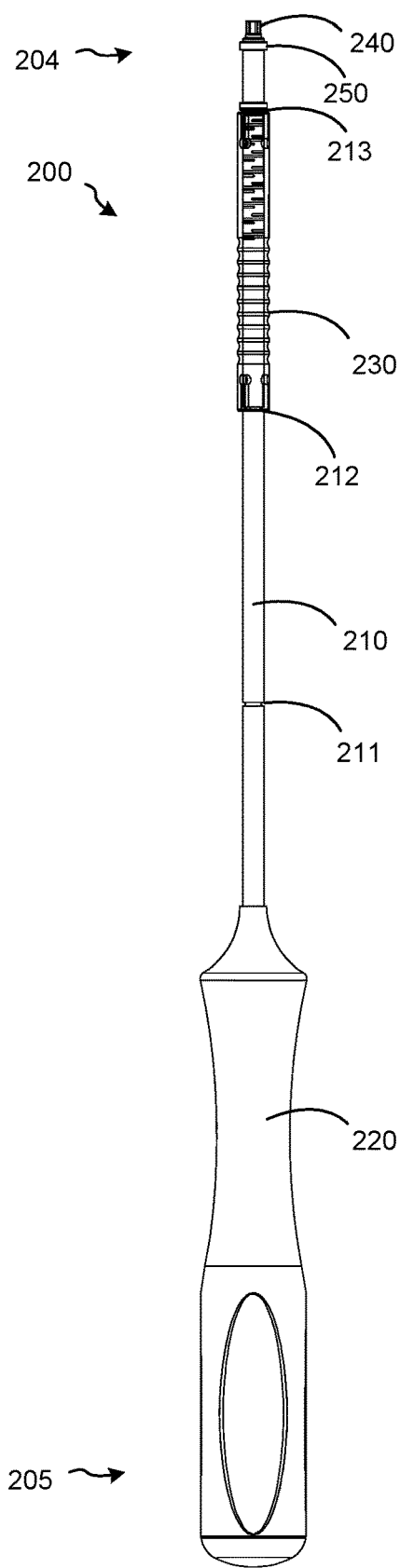
FIG. 2A is a side view of a flexible driver tool, according to an embodiment of the present disclosure.
Figure 2B:
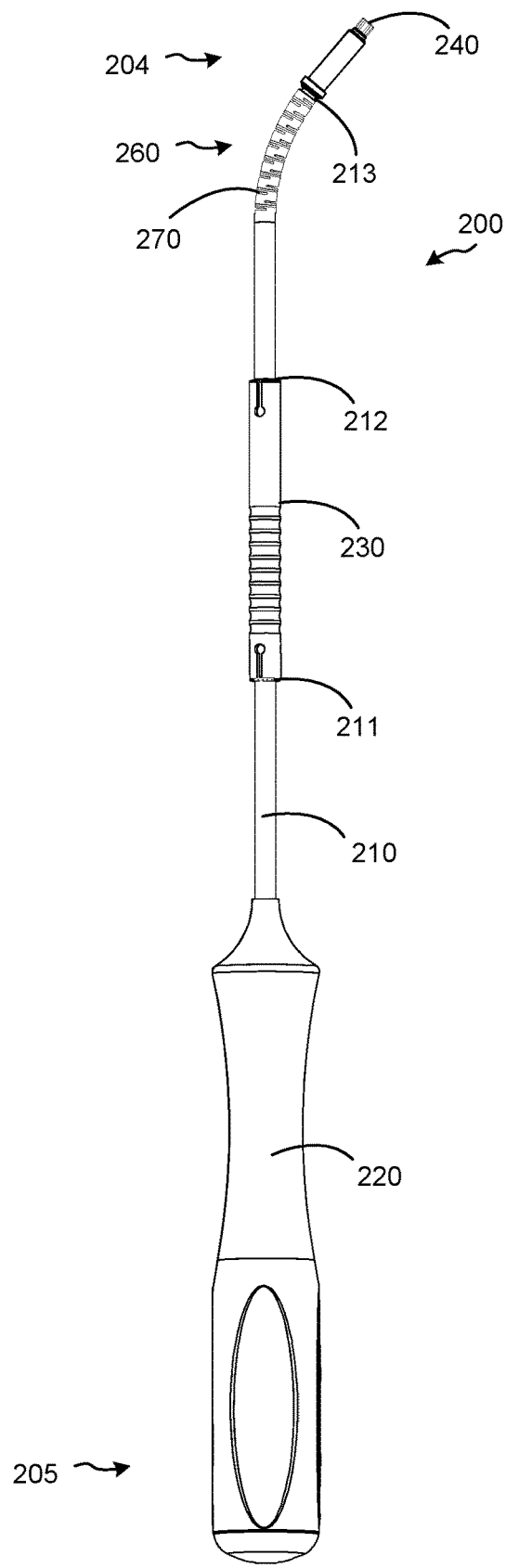
FIG. 2B is a side view of the flexible driver tool of FIG. 2A in flexion.
Figure 2C:
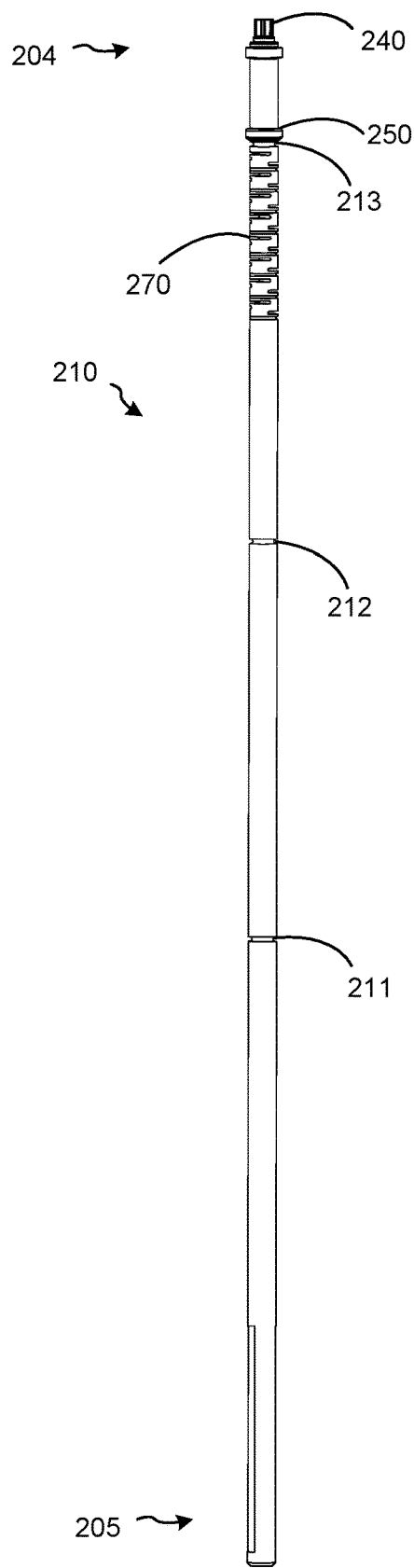
FIG. 2C is a side view of a flexible driver shaft of the flexible driver tool of FIG. 2A.
Figure 2D:
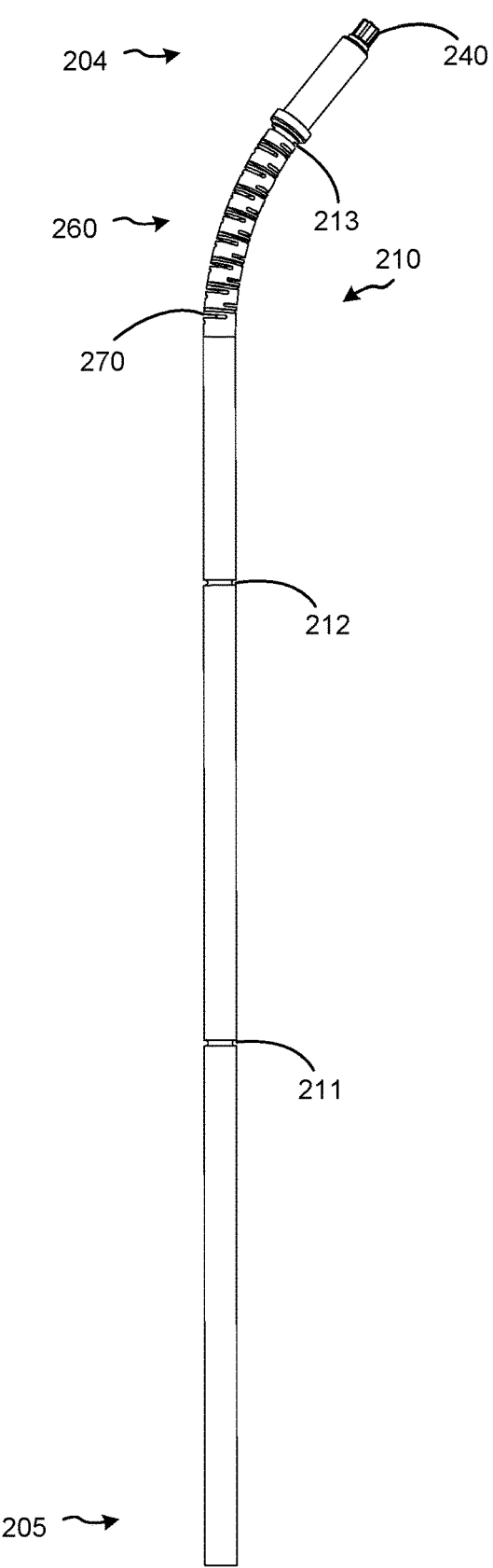
FIG. 2D is a side view of the flexible driver shaft of FIG. 2C in flexion.
Figure 2E:
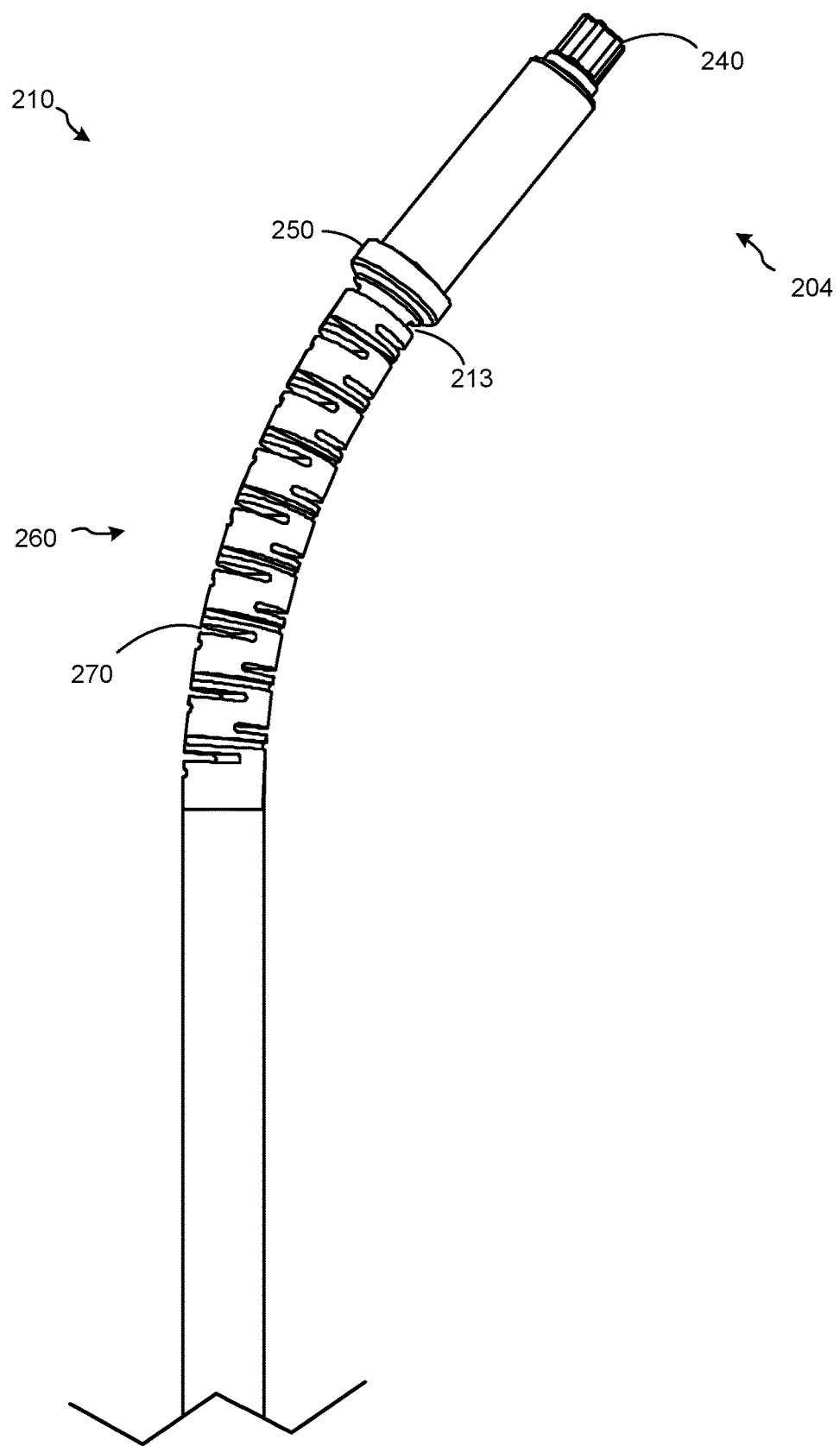
FIG. 2E is a close up view of a distal end of the flexible driver shaft of FIG. 2D.
Figure 2F:
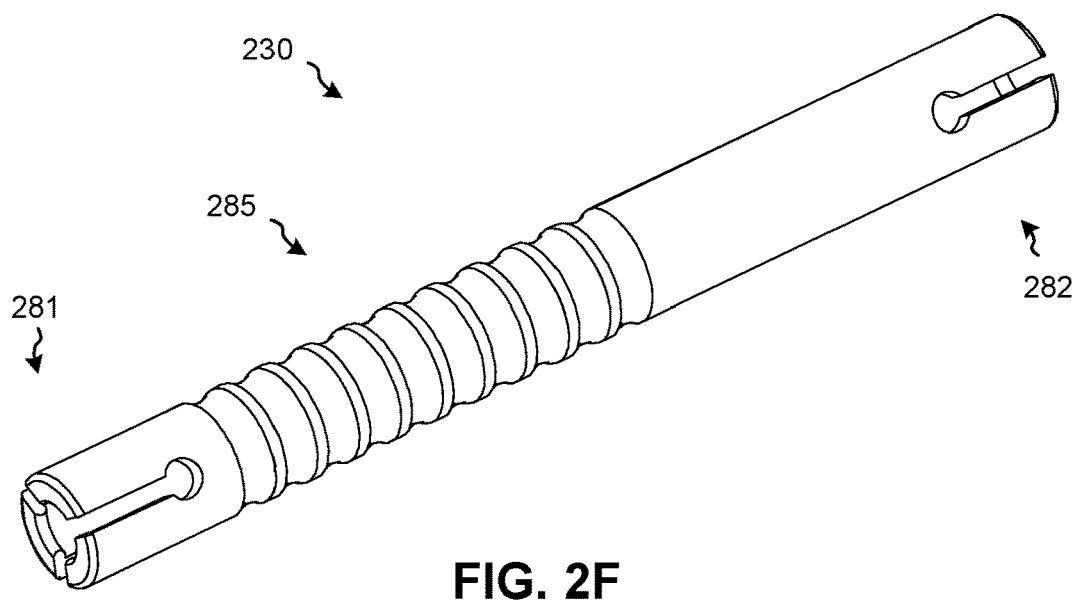
FIG. 2F is a perspective view of a driver sleeve of the flexible driver tool of FIG. 2A.
Figure 2G:
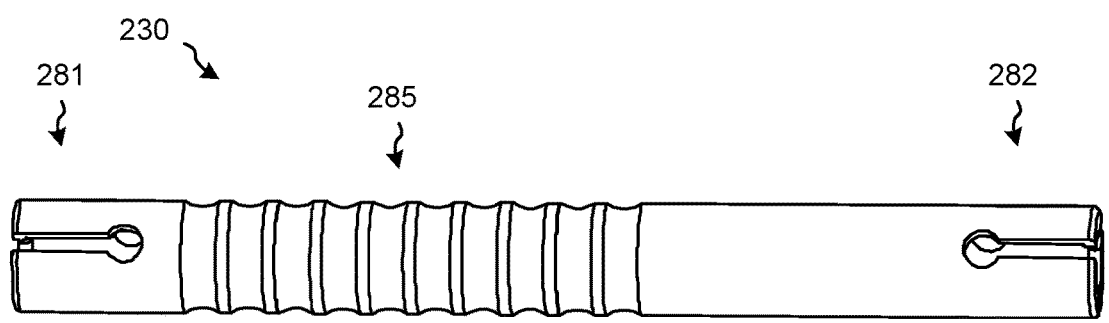
FIG. 2G is a side view of the driver sleeve of FIG. 2F.
Figure 2H:
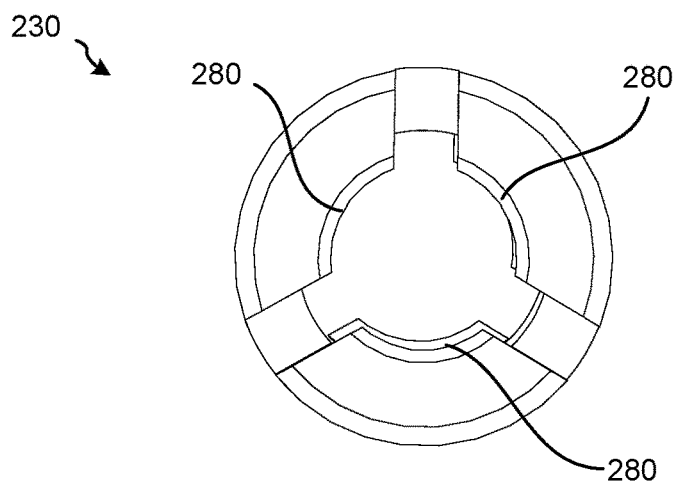
FIG. 2H is an end view of the driver sleeve of FIG. 2F.
Figure 2I:
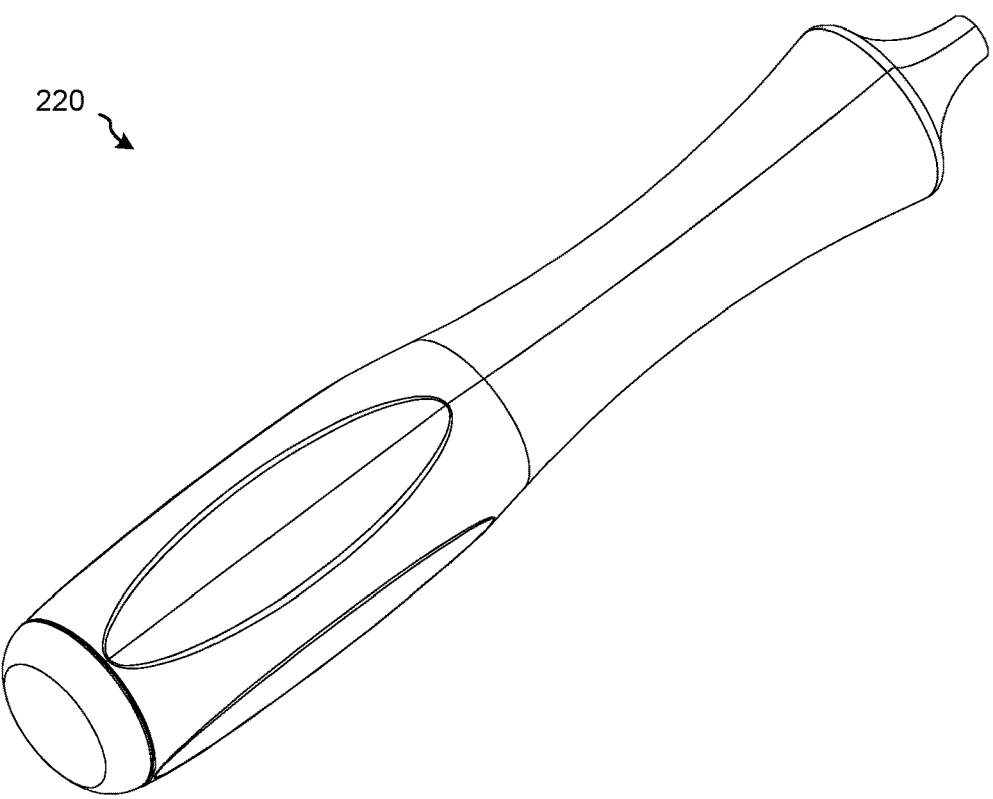
FIG. 2I is a perspective top view of a driver handle of the flexible driver tool of FIG. 2A.
Figure 2J:
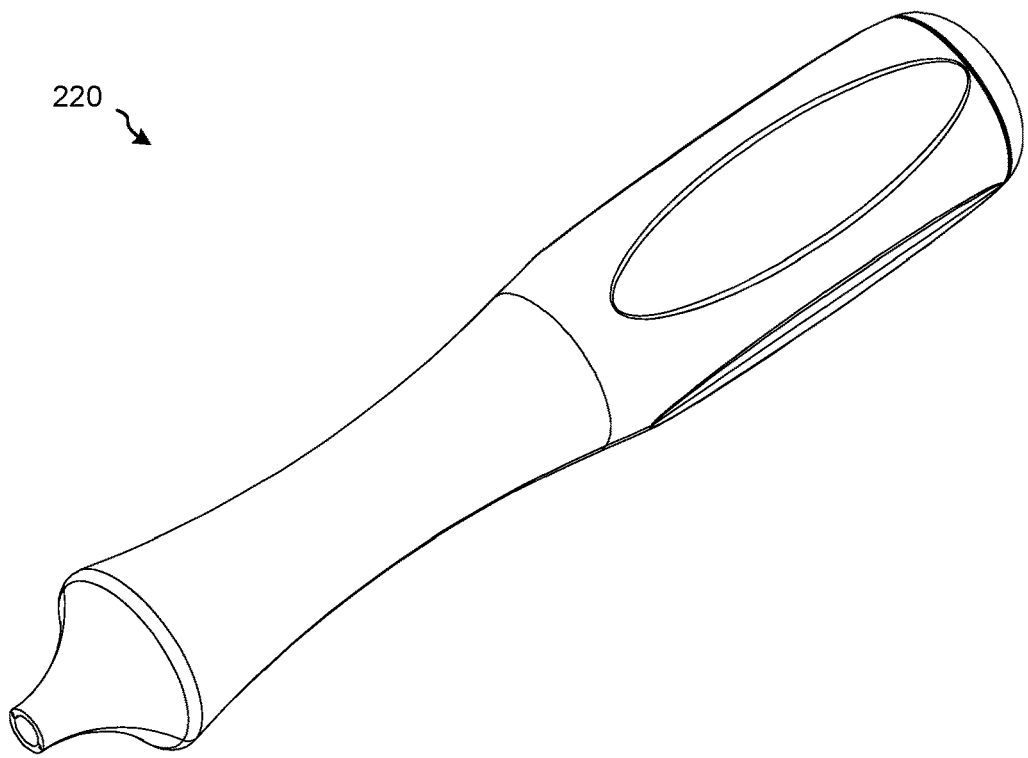
FIG. 2J is a perspective bottom view of the driver handle of FIG. 2I.

FIGS. 2A-2J illustrate various views of a flexible driver tool 200 and its components, according to an embodiment of the present disclosure. Specifically, FIG. 2A is a side view of the flexible driver tool 200; FIG. 2B is a side view of the flexible driver tool 200 in flexion; FIG. 2C is a side view of a flexible driver shaft 210 of the flexible driver tool 200; FIG. 2D is a side view of the flexible driver shaft 210 in flexion; FIG. 2E is a close up view of a distal end 204 of the flexible driver shaft 210; FIG. 2F is a perspective view of a driver sleeve 230 of the flexible driver tool 200; FIG. 2G is a side view of the driver sleeve 230; FIG. 2H is an end view of the driver sleeve 230; FIG. 2I is a perspective top view of a driver handle 220 of the flexible driver tool 200; and FIG. 2J is a perspective bottom view of the driver handle 220.

The flexible driver tool 200 may include a proximal end 205, a distal end 204, a flexible driver shaft 210, a driver handle 220, a driver sleeve 230, a driver depth stop ring 250, and a working member comprising a driver engagement feature 240. The driver sleeve 230 may similarly translate in the proximal and distal directions along the flexible driver shaft 210 in order to selectively prevent or allow the flexible driver shaft 210 from bending at the flexible portion 260 of the flexible driver shaft 210. For example, FIG. 2A shows the driver sleeve 230 translated distally in order to provide rigid support to the flexible driver shaft 210 over the flexible portion 260 of the flexible driver shaft 210. FIG. 2B shows the driver sleeve 230 translated proximally in order to allow the flexible portion 260 of the flexible driver shaft 210 the freedom to bend and flex. The flexible driver shaft 210 may also include a first notch 211, a second notch 212, and a third notch 213, which may interact with corresponding protrusions 280 formed on a proximal end 281 and a distal end 282 of the driver sleeve 230 to selectively retain the driver sleeve 230 in a locked position (e.g., when the driver sleeve 230 is translated proximally) and an unlocked position (e.g., when the driver sleeve 230 is translated distally). Likewise, a tactile and/or audible "click" may be felt and/or heard by the surgeon when the driver sleeve 230 reaches the unlocked and/or locked positions. In at least one embodiment, the proximal and distal ends 281, 282 of the driver sleeve 230 may comprise collet structures that provide resiliency to the protrusions 280 of the driver sleeve 230 to allow them to selectively engage and disengage with the first, second, and third notches 211, 212, 213 of the flexible driver shaft 210. The driver sleeve 230 may also include a grip feature 285 to facilitate translation of the driver sleeve 230 between the locked and unlocked positions. In at least one embodiment, the flexible portion 260 of the flexible driver shaft 210 may comprise a plurality of slots 270 formed in the flexible driver shaft 210 and configured to allow the flexible portion 260 of the flexible driver shaft 210 to bend and flex away from a longitudinal axis of the flexible driver shaft 210. However, it will be understood that any suitable structure or arrangement may also be utilized to achieve flexion in the flexible driver shaft 210. Operation of the flexible driver tool 200 will be discussed in more detail below with respect to FIGS. 18 and 19.

Figure 3A:
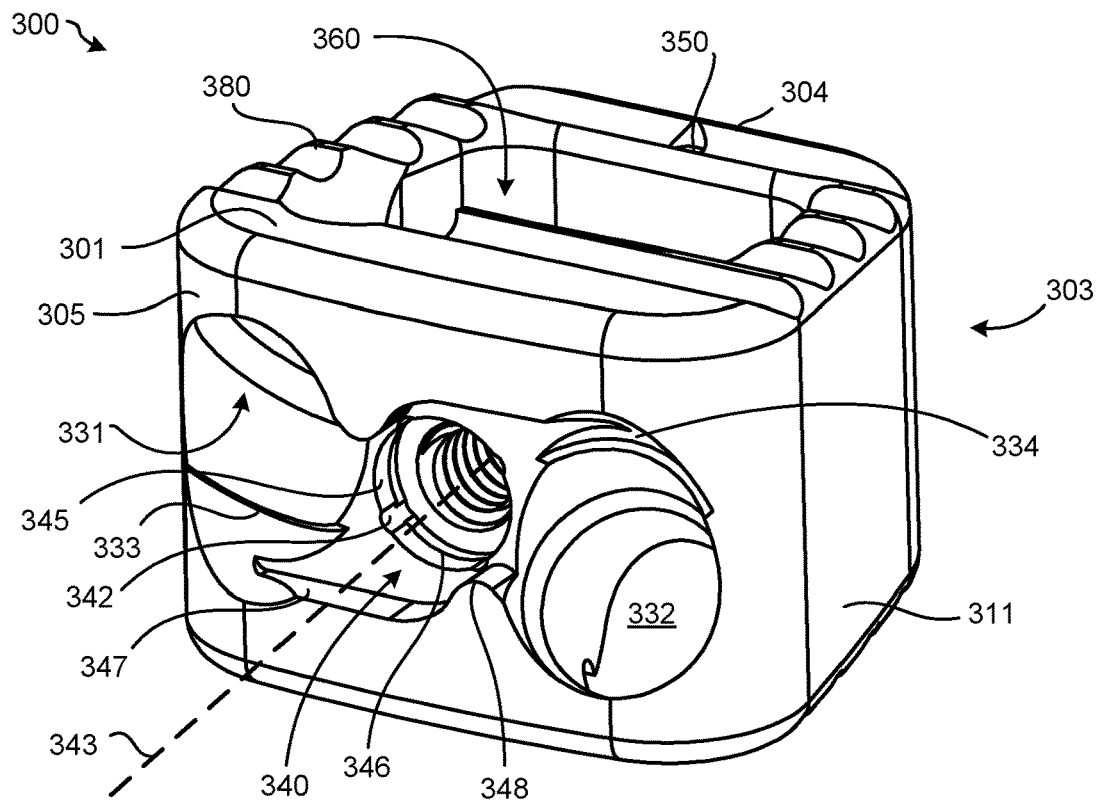
FIG. 3A is a perspective top view of a proximal end of an intervertebral spacer, according to an embodiment of the present disclosure.
Figure 3B:
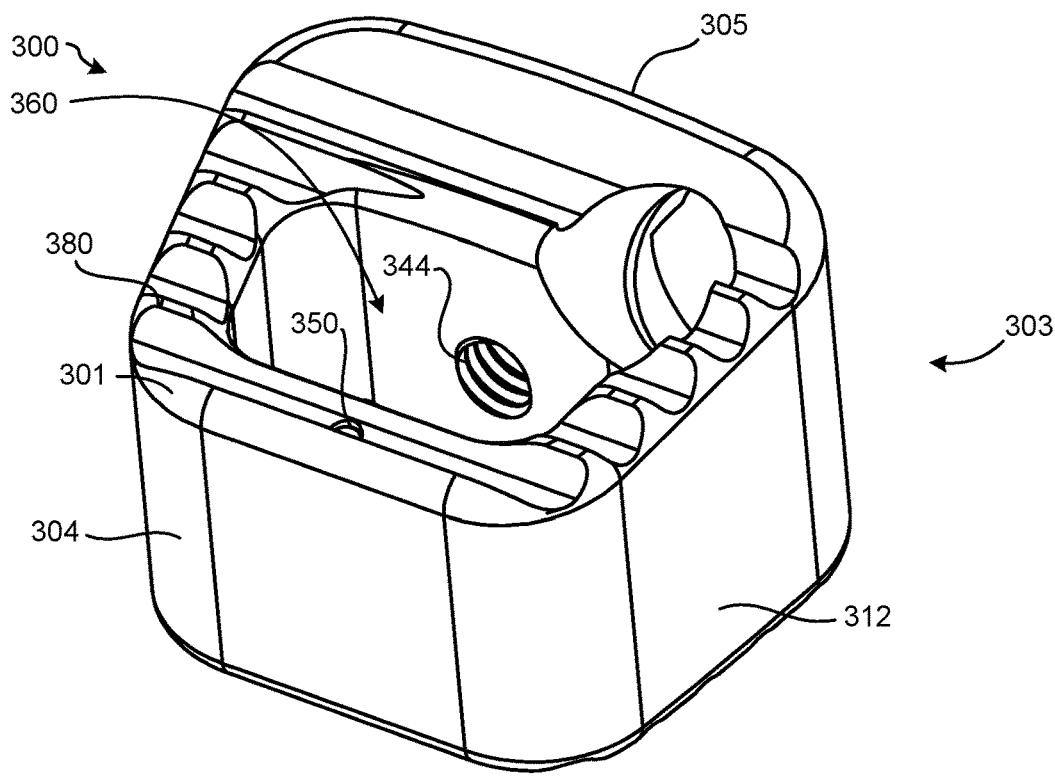
FIG. 3B is a perspective top view of a distal end of the intervertebral spacer of FIG. 3A.
Figure 3C:
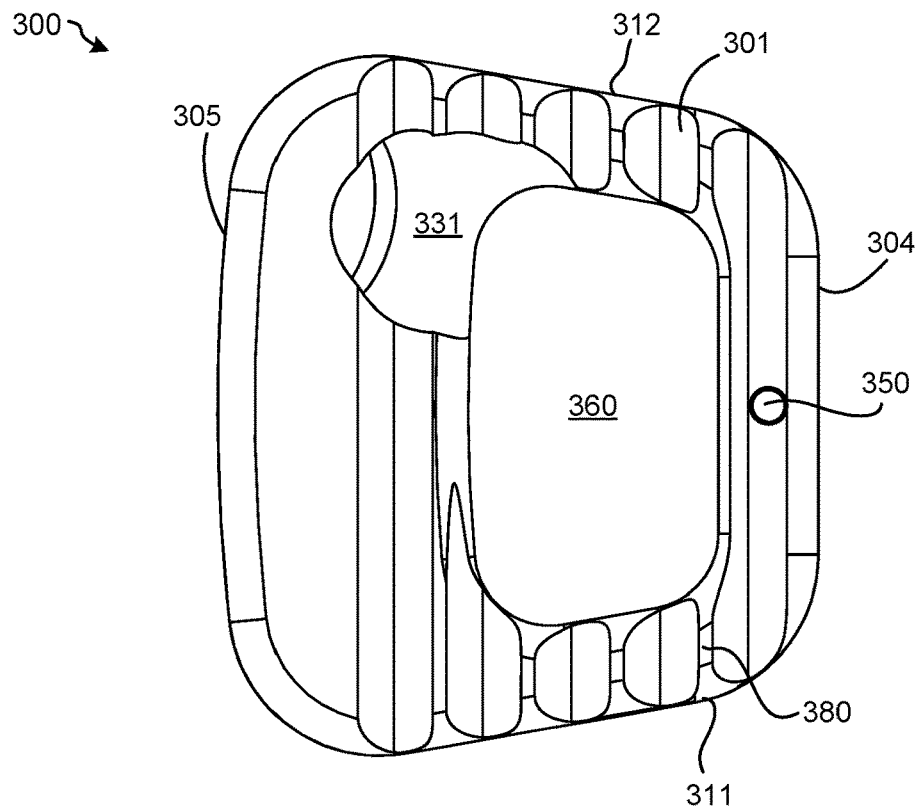
FIG. 3C is a top view of the intervertebral spacer of FIG. 3A.
Figure 3D:
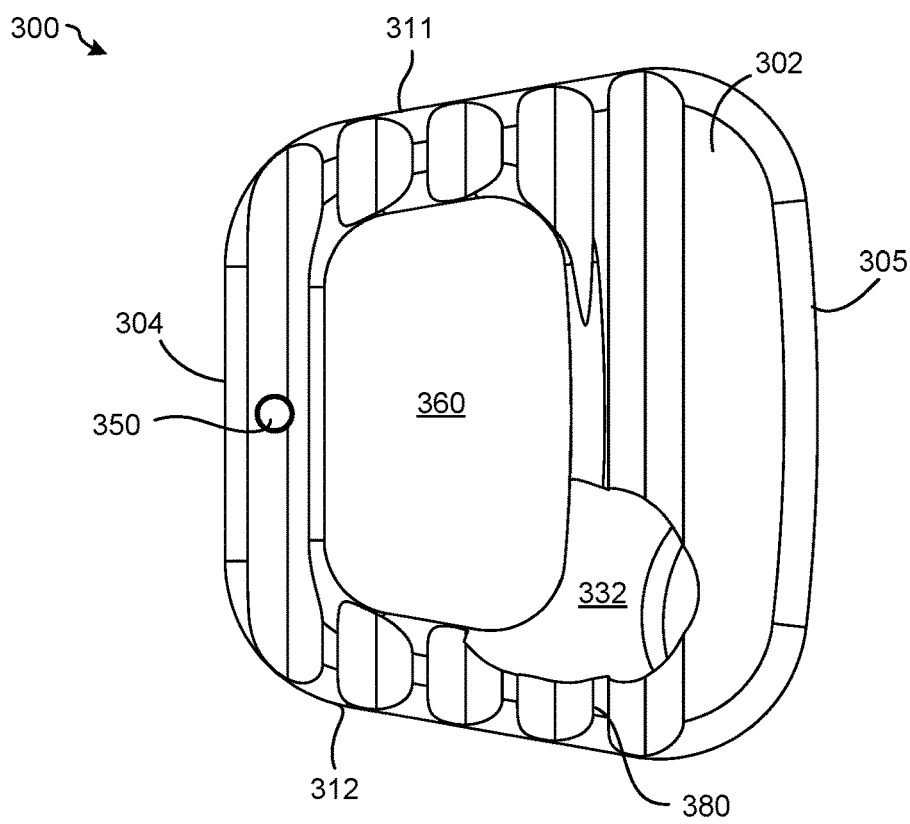
FIG. 3D is a bottom view of the intervertebral spacer of FIG. 3A.
Figure 3E:
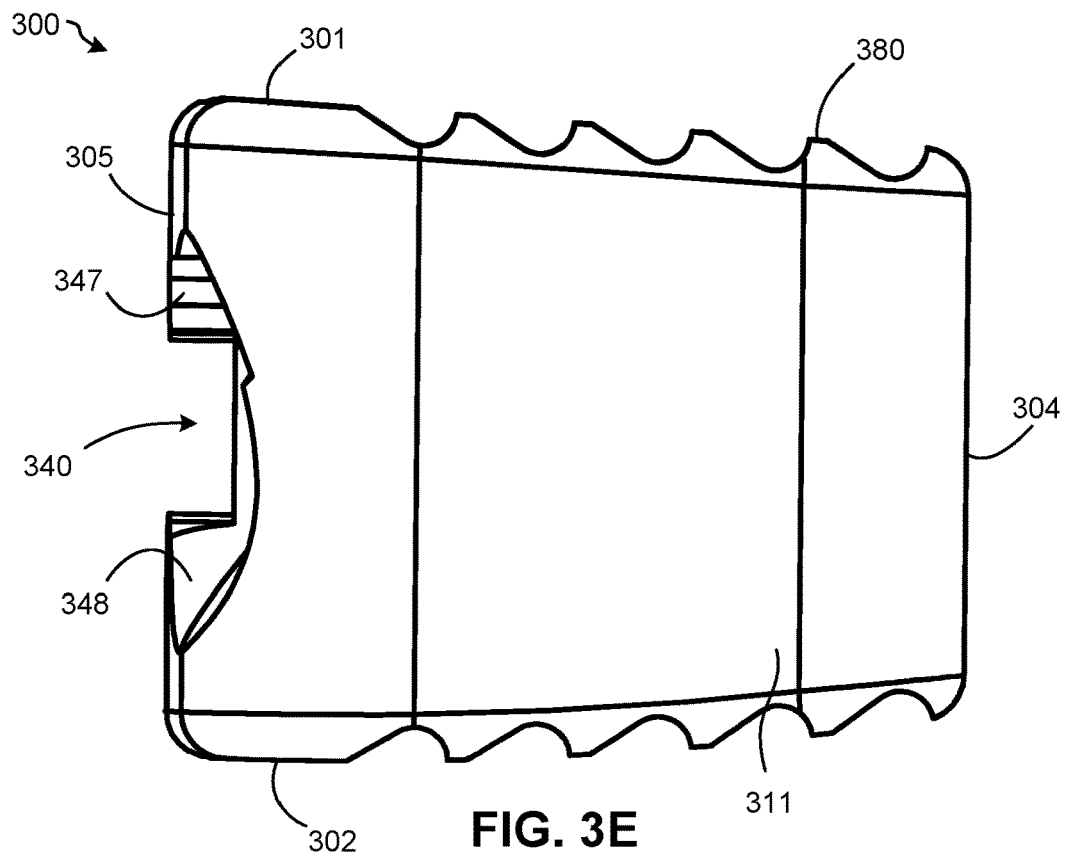
FIG. 3E illustrates a first side of the intervertebral spacer of FIG. 3A.
Figure 3F:
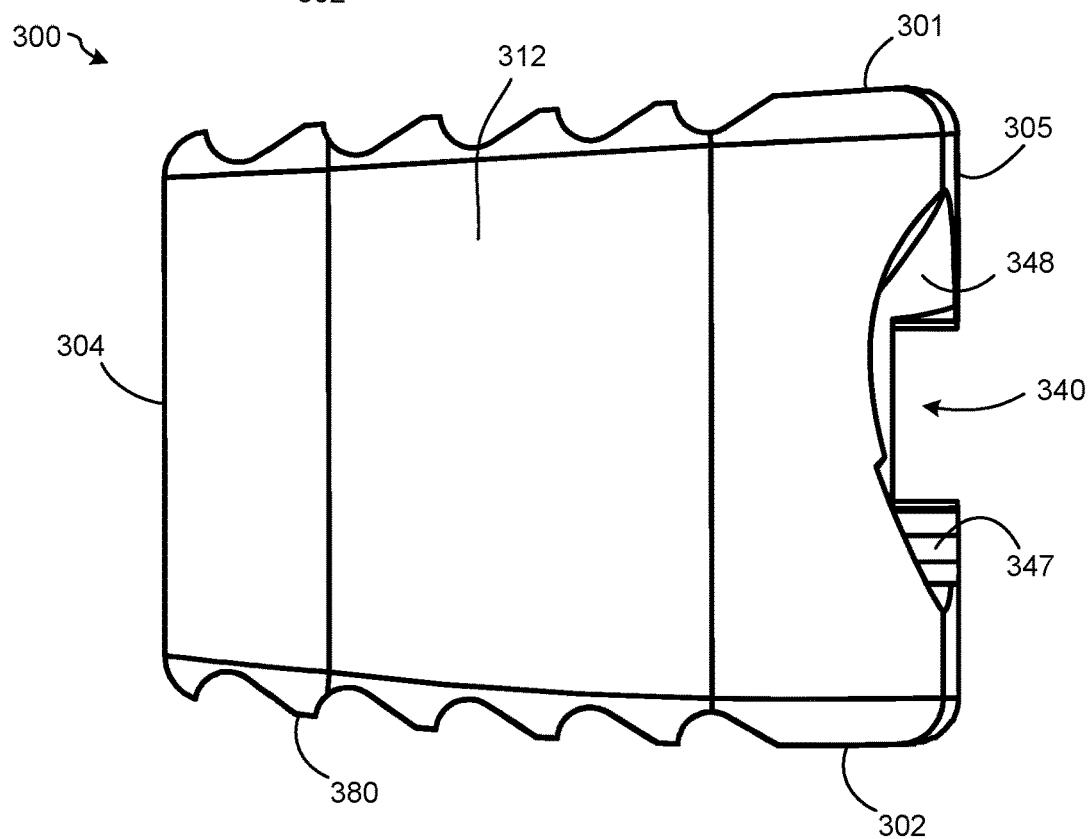
FIG. 3F illustrates a second side of the intervertebral spacer of FIG. 3A.
Figure 3G:
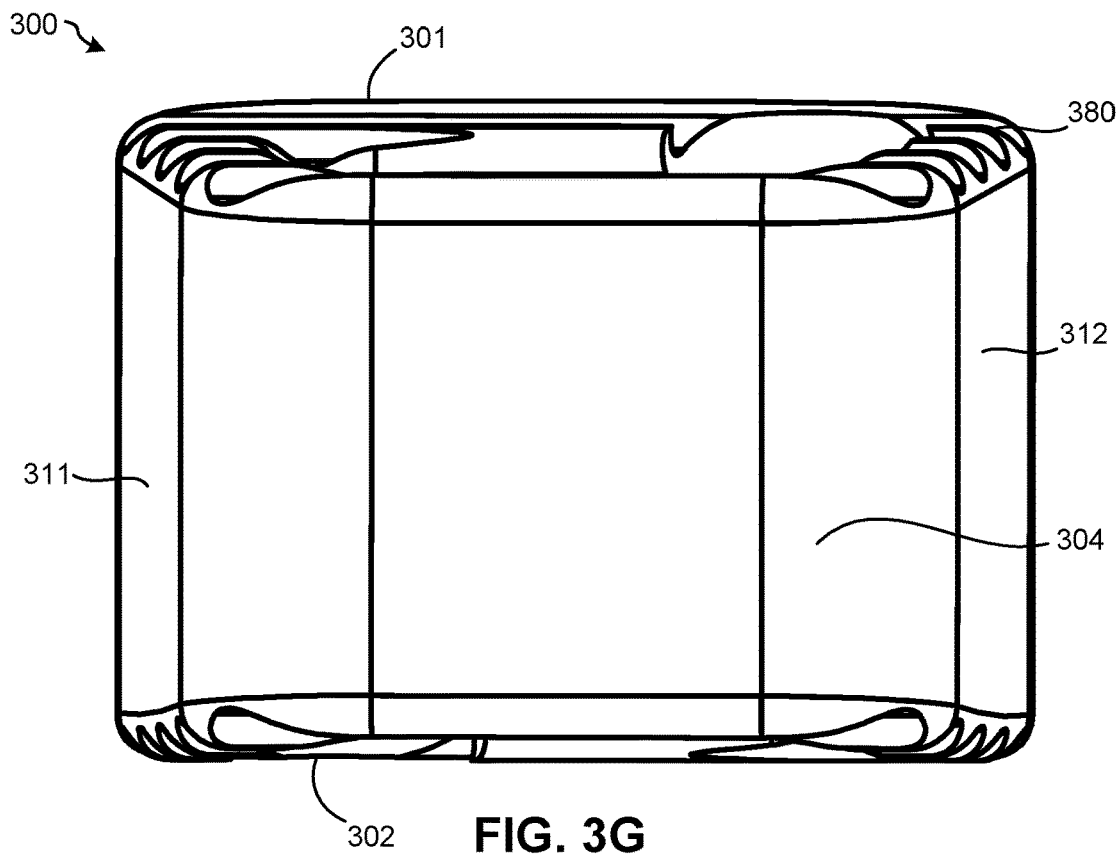
FIG. 3G illustrates the distal end of the intervertebral spacer of FIG. 3A.
Figure 3H:
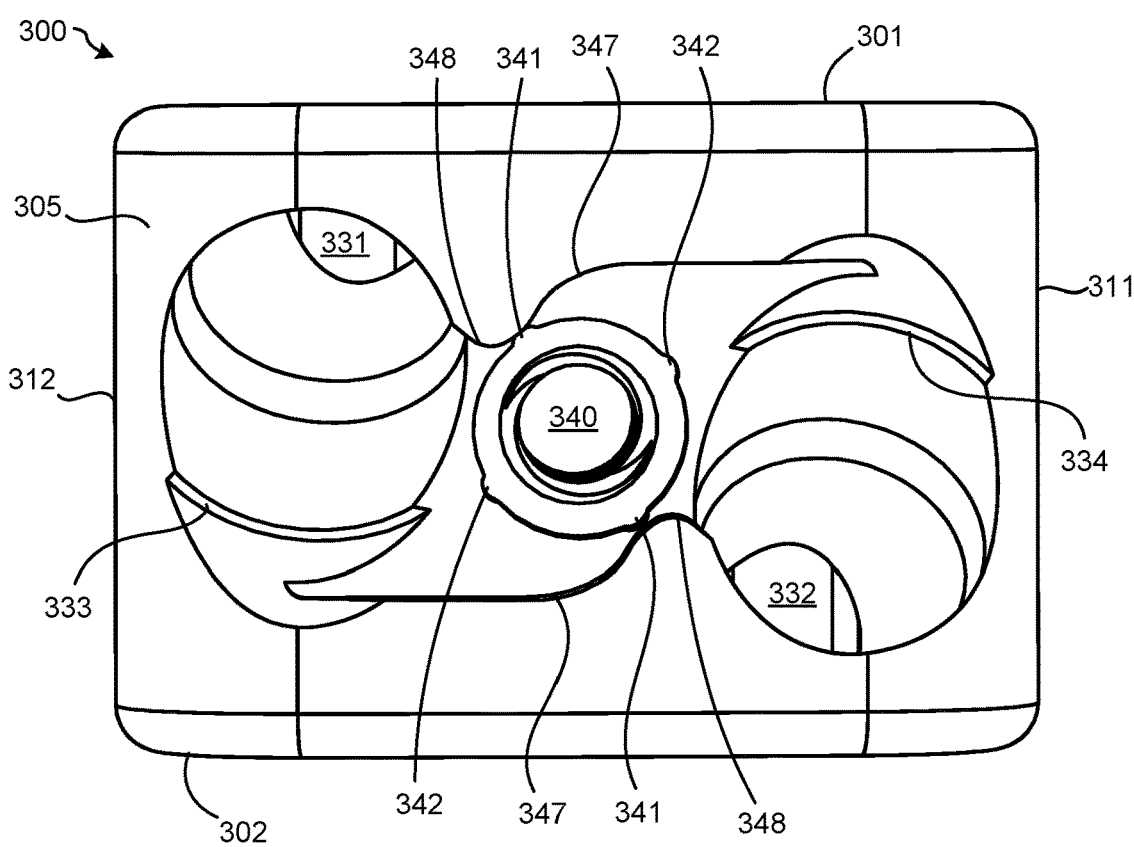
FIG. 3H illustrates the proximal end of the intervertebral spacer of FIG. 3A.

FIGS. 3A-3H illustrate various views of an intervertebral spacer 300, according to an embodiment of the present disclosure. Specifically, FIG. 3A is a perspective top view of a proximal end 305 or a proximal surface of the intervertebral spacer 300; FIG. 3B is a perspective top view of a distal end 304 of the intervertebral spacer 300; FIG. 3C is a top view of the intervertebral spacer 300; FIG. 3D is a bottom view of the intervertebral spacer 300; FIG. 3E illustrates a first side 311 of the intervertebral spacer 300; FIG. 3F illustrates a second side 312 of the intervertebral spacer 300; FIG. 3G is a view of the distal end 304 of the intervertebral spacer 300; and FIG. 3H is a view of the proximal end 305 of the intervertebral spacer 300.

The intervertebral spacer 300 may generally include a superior surface 301 configured to engage a superior vertebral body (not shown), an inferior surface 302 configured to engage an inferior vertebral body (not shown), and a peripheral wall 303 extending from the superior surface 301 to the inferior surface 302. The peripheral wall 303 may generally comprise the distal end 304, the proximal end 305, the first side 311, and the second side 312 of the intervertebral spacer 300.

The intervertebral spacer 300 may include one or more bone graft channels 360 oriented to pass through opposing ends of the intervertebral spacer 300. For example, the one or more bone graft channels 360 may be formed through the superior and inferior surfaces 301, 302 of the intervertebral spacer 300. The intervertebral spacer 300 may also include one or more side bone graft channels (not shown) that may be formed in the first and second sides 311, 312 of the intervertebral spacer 300. The bone graft channel(s) may be configured to receive bone graft material (not shown) and/or other suitable materials that are known in the art. The intervertebral spacer 300 may also include one or more serrated teeth 380 formed in the superior and inferior surfaces 301, 302 of the intervertebral spacer 300. The one or more serrated teeth 380 may be configured to help stabilize the intervertebral spacer 300 between adjacent vertebral bodies during the fusion process. Moreover, bone graft and/or other suitable materials may also be placed between adjacent serrated teeth 380 of the intervertebral spacer 300 in order to enhance the fusion process and/or help stabilize the intervertebral spacer 300 between adjacent vertebral bodies during the fusion process.

Figure 5A:
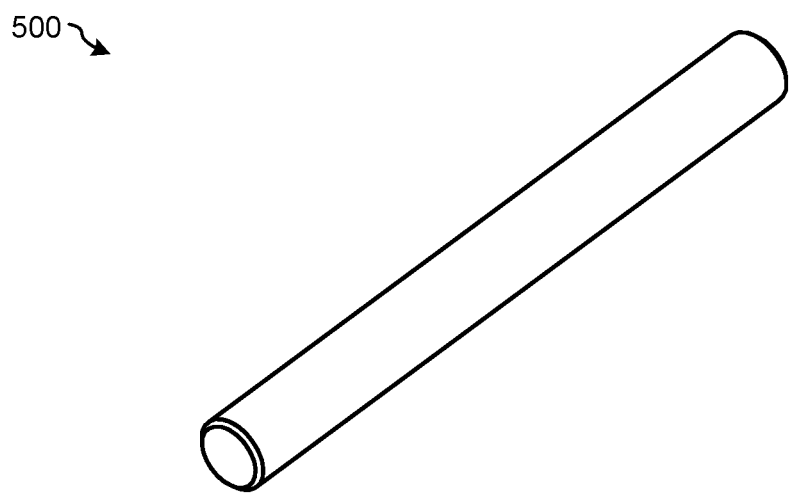
FIG. 5A is a perspective view of a radiopaque marker, according to an embodiment of the present disclosure.
Figure 5B:
FIG. 5B is a side view of the radiopaque marker of FIG. 5A.
Figure 5C:
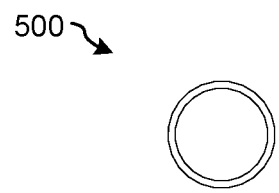
FIG. 5C is an end view of the radiopaque marker of FIG. 5A.
Figure 6A:
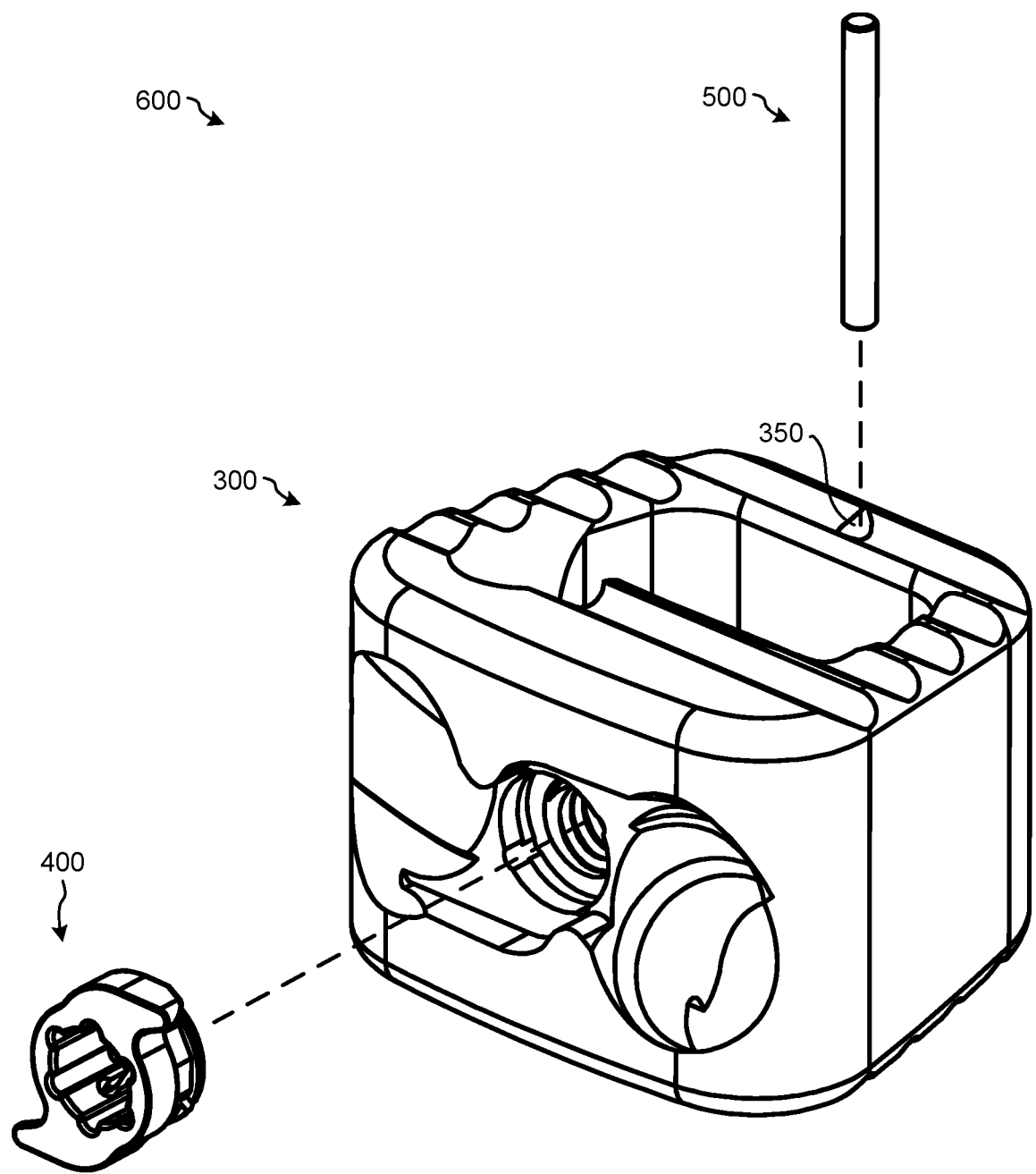
FIG. 6A is an exploded view of an intervertebral spacer assembly including the intervertebral spacer of FIGS. 3A-3H, the locking member of FIGS. 4A-4F, and the radiopaque marker of FIGS. 5A-5C.
Figure 6B:
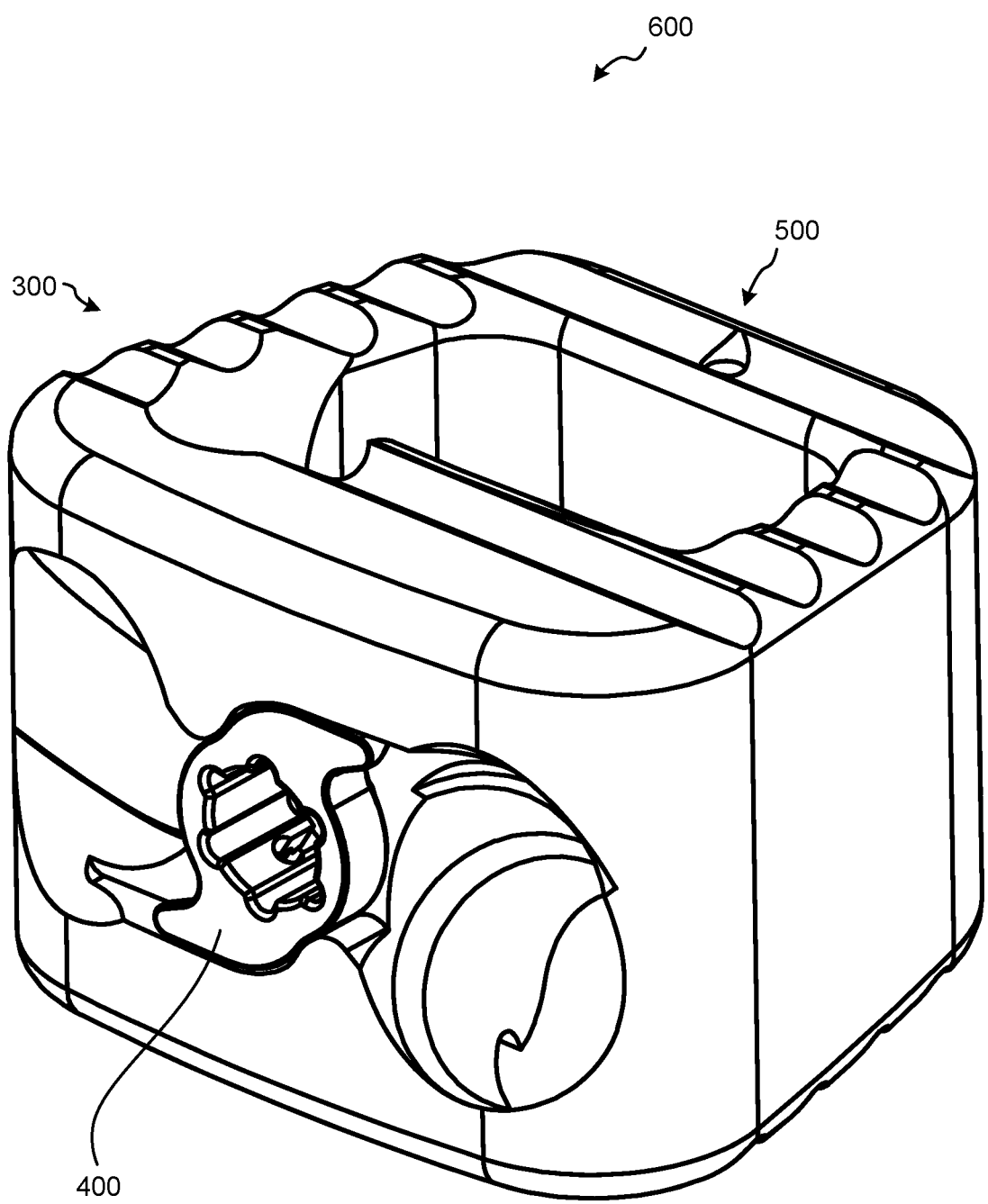
FIG. 6B is a perspective view of the intervertebral spacer assembly of FIG. 6A, after assembly.

The intervertebral spacer 300 may also include one or more marker apertures 350. The one or more marker apertures 350 may be configured to receive one or more radiopaque makers 500, as can be seen in FIGS. 5A-5C. The radiopaque makers 500 may be made from any suitable radiopaque material, such as tantalum (as one non-limiting example). The one or more radiopaque makers 500 may be respectively inserted into the one or more marker apertures 350 in order to couple the one or more radiopaque makers 500 to the intervertebral spacer 300, as can be seen in the exploded view of FIG. 6A, and in the assembled view of FIG. 6B. In this manner, the one or more radiopaque makers 500 may be utilized to verify whether or not the intervertebral spacer 300 has been correctly placed between adjacent vertebral bodies via a suitable x-ray imaging process, which may be performed intraoperatively and/or postoperatively.

Figure 7A:
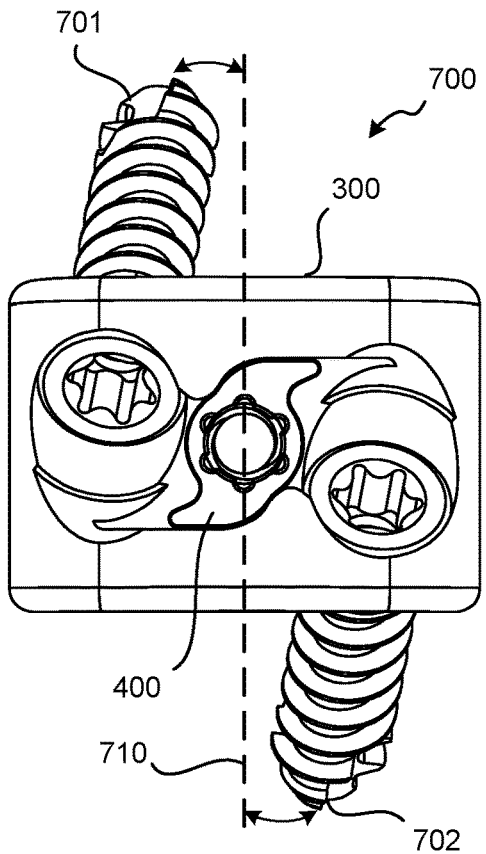
FIG. 7A is a proximal end view of an intervertebral spacer assembly including bone screws and a locking member positioned in an unlocked position, according to an embodiment of the present disclosure.
Figure 7B:
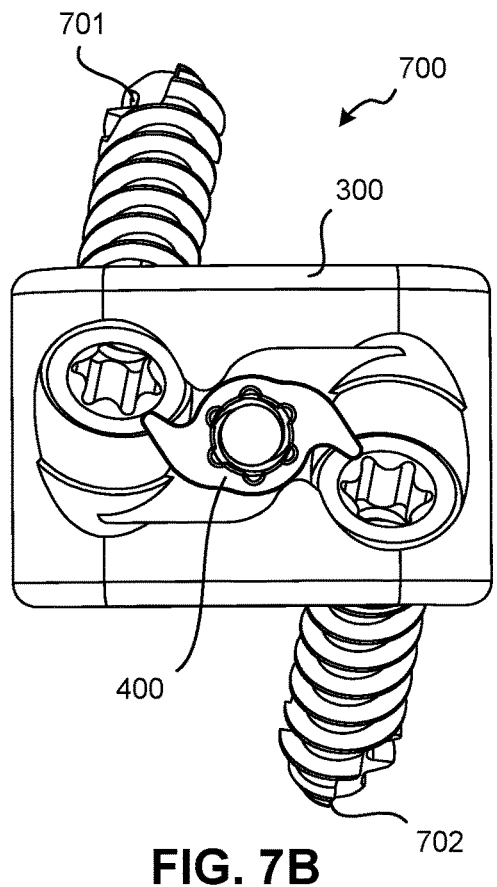
FIG. 7B is a proximal end view of the intervertebral spacer assembly of FIG. 7A with the locking member positioned in a locked position.
Figure 7C:
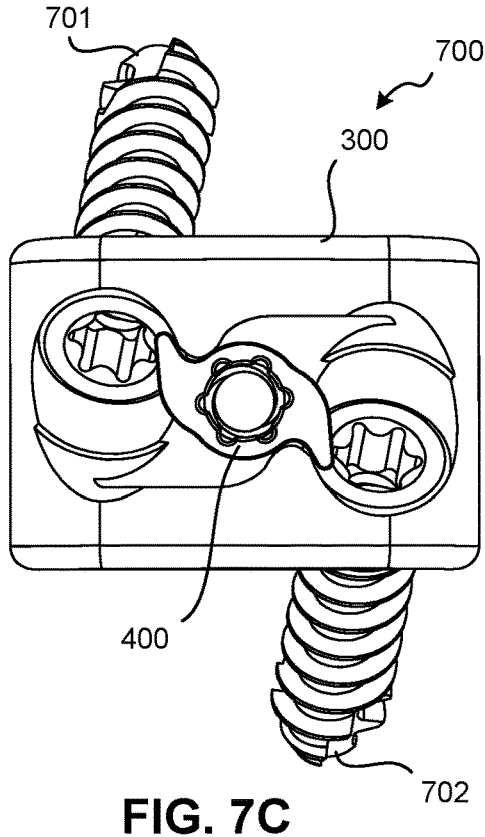
FIG. 7C is a proximal end view of the intervertebral spacer assembly of FIG. 7A with the locking member positioned in an alternative locked position.
Figure 7D:
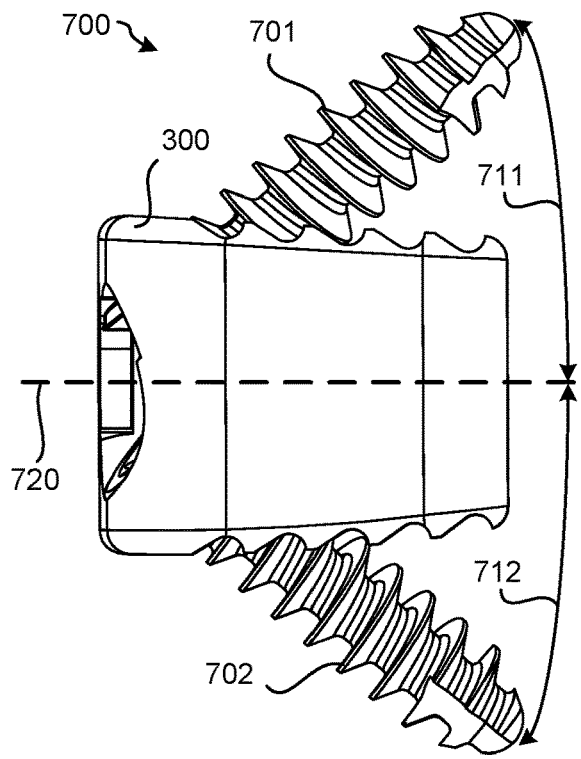
FIG. 7D is a side view of the intervertebral spacer assembly of FIG. 7A.

The proximal end 305 of the intervertebral spacer 300 may include a first fastener channel 331 configured to receive a first fastener or bone screw 701 (e.g., see FIGS. 7A-7D). The first fastener channel 331 may be oriented to pass through the proximal and superior surfaces of the intervertebral spacer 300 at a first angle 711 with respect to a mid-line 720, as shown in FIG. 7D. The proximal end 305 of the intervertebral spacer 300 may also include a second fastener channel 332 configured to receive a second fastener or bone screw 702. The second fastener channel 332 may be oriented to pass through the proximal and inferior surfaces of the intervertebral spacer 300 at a second angle 712 with respect to the mid-line 720, as shown in FIG. 7D.

In some embodiments, the first and second angles 711, 712 may be substantially equal to each other and may be between 10 and 50 degrees. In a particular embodiment, the first and second angles 711, 712 may be about 30 degrees. However, it will be understood that the first and second angles 711, 712 may utilize any angle between 0 degrees and 90 degrees.

Moreover, the first and second fastener channels 331, 332 (and thus bone screws 701, 702) may also be angled inward with respect to a mid-line 710, as shown in FIG. 7A. In at least one embodiment, the bone screws 701, 702 may be angled inward toward the mid-line 710 by about 5 degrees. However, it will be understood that the bone screws 701, 702 may be angled inward toward the mid-line 710, or outward away from the mid-line 710, according to any angle.

The first and second fastener channels 331, 332 may also comprise a first depth stop 333 and a second depth stop 334. The first and second depth stops 333, 334 may prevent the flexible awl tool 10-0 and/or the flexible driver tool 200 from penetrating too far within the first and second fastener channels 331, 332.

The proximal end 305 of the intervertebral spacer 300 may also include a locking member channel 340 intermediate the first and second fastener channels 331, 332. The locking member channel 340 may include an inner wall 345, an annular ridge 346 formed in the inner wall 345, a first pair of recesses 341 formed in the inner wall 345, and a second pair of recesses 342 formed in the inner wall 345. The second pair of recesses 342 may be angularly offset from the first pair of recesses 341 about a longitudinal axis 343 of the locking member channel 340 (see FIGS. 3A and 3H). In some embodiments, the second pair of recesses 342 may be angularly offset from the first pair of recesses 341 by about 30 degrees. In some embodiments, the second pair of recesses 342 may be angularly offset from the first pair of recesses 341 by about 90 degrees. In some embodiments, the second pair of recesses 342 may be angularly offset from the first pair of recesses 341 at any angle between 10 and 170 degrees. However, it will be also understood that the second pair of recesses 342 may be angularly offset from the first pair of recesses 341 at any angle between 0 and 360 degrees. The locking member channel 340 may also include first threading 344 configured to engage second threading formed on an inserter tool, as will be discussed below with respect to FIGS. 9A-10B.

The proximal end 305 of the intervertebral spacer 300 may also include a first pair of stop surfaces 347 configured to prevent a locking member 400 from rotating in a first direction (e.g., counter clockwise) past an unlocked position (see FIG. 7A), and a second pair of stop surfaces 348 configured to prevent the locking member 400 from rotating in a second direction (e.g., clockwise) past a locked position (see FIG. 7C).

Figure 4A:
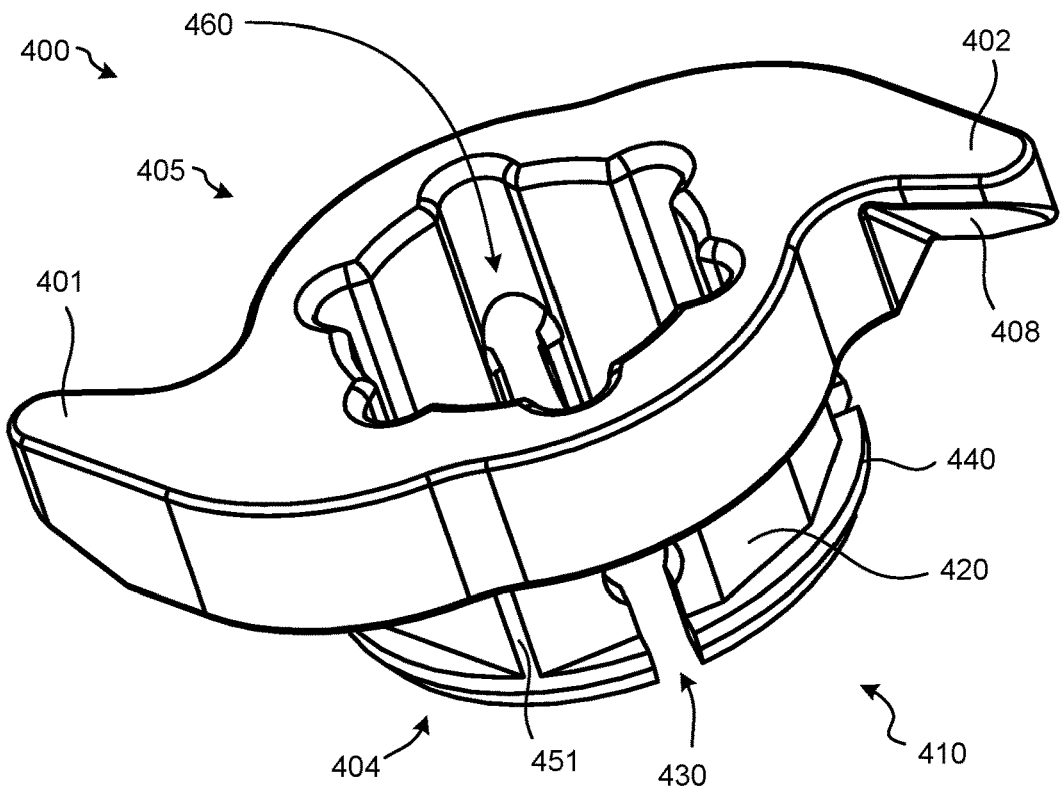
FIG. 4A is a perspective top view of a locking member, according to an embodiment of the present disclosure.
Figure 4B:
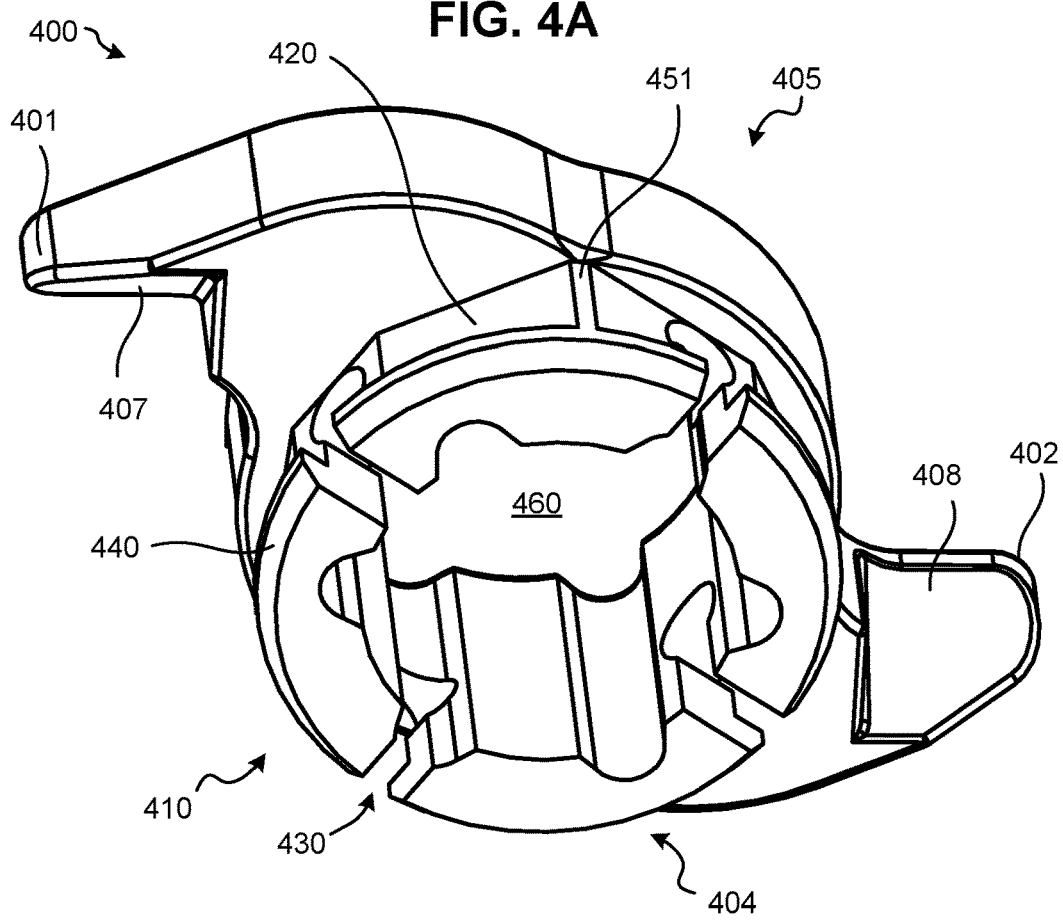
FIG. 4B is a perspective bottom view of the locking member of FIG. 4A.
Figure 4C:
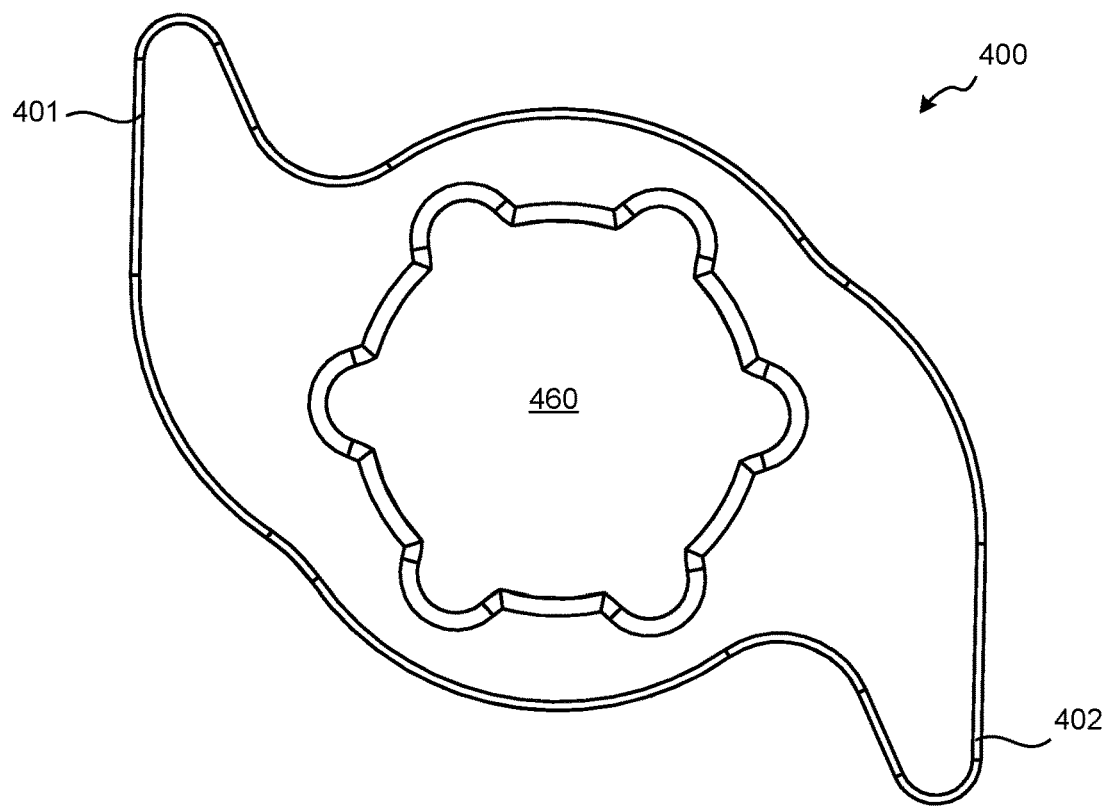
FIG. 4C is a top view of the locking member of FIG. 4A.
Figure 4D:
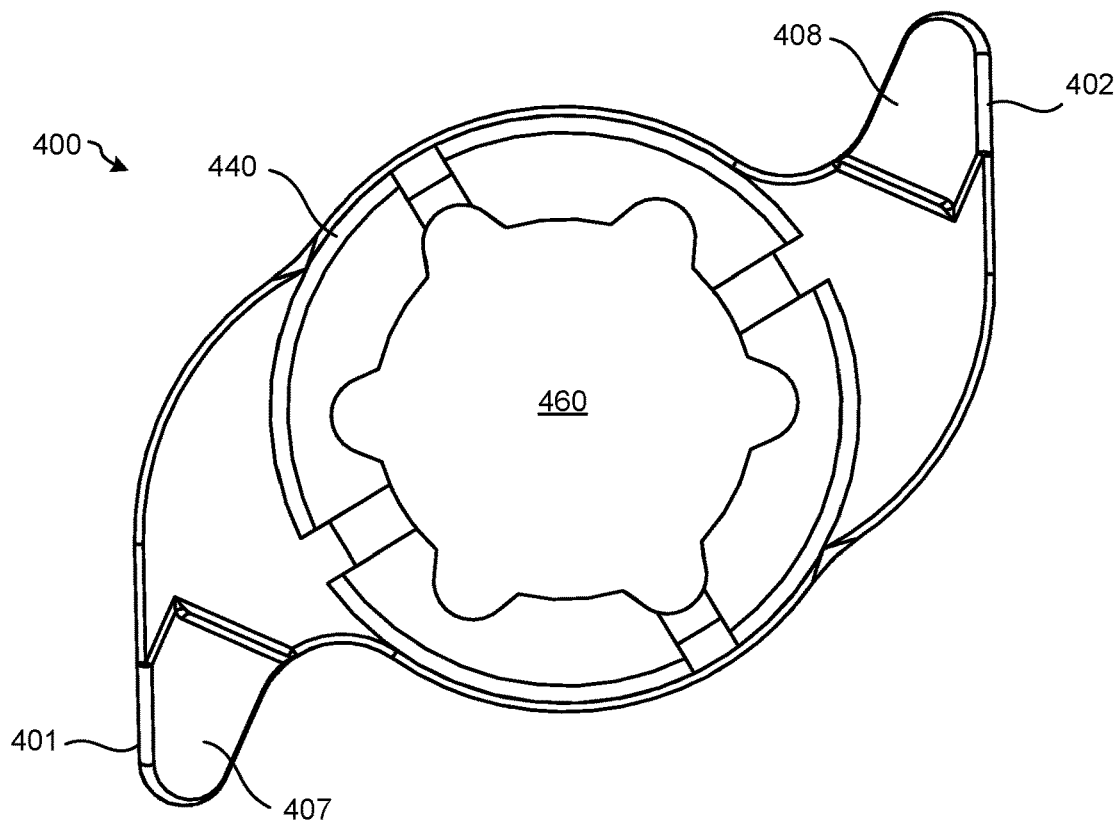
FIG. 4D is a bottom view of the locking member of FIG. 4A.
Figure 4E:
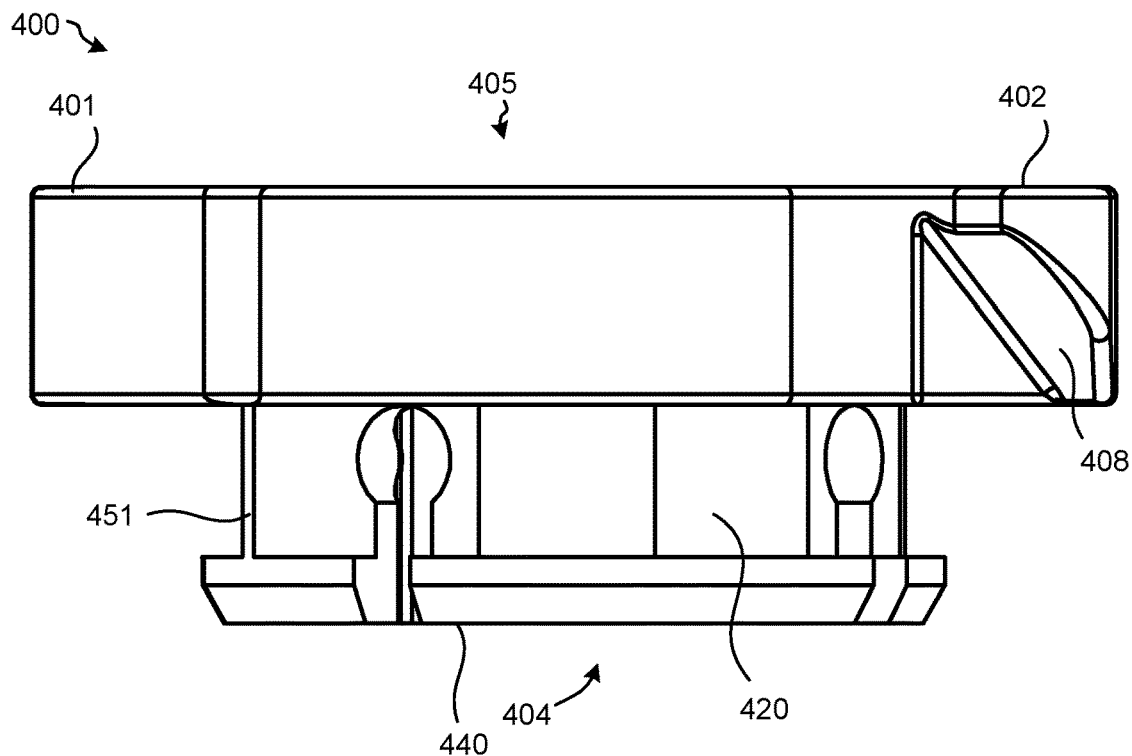
FIG. 4E illustrates a first side of the locking member of FIG. 4A.
Figure 4F:
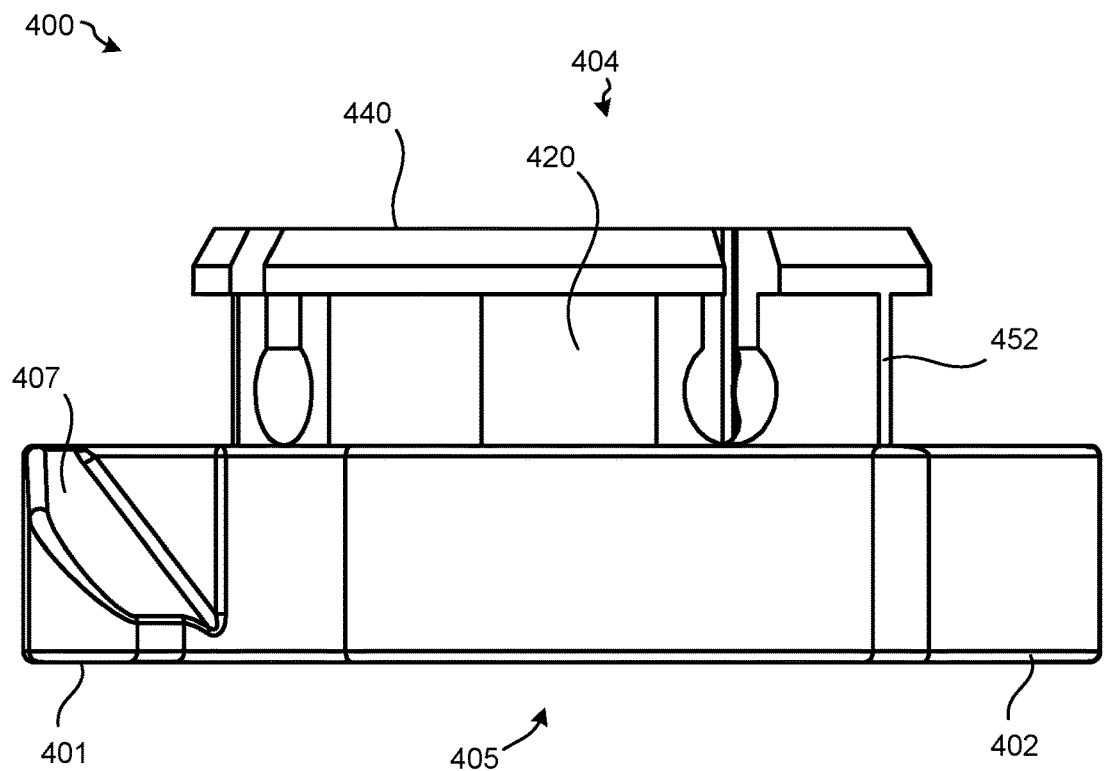
FIG. 4F illustrates a second side of the locking member of FIG. 4A.

FIGS. 4A-4F illustrate various views of a locking member 400, according to an embodiment of the present disclosure. Specifically, FIG. 4A is a perspective top view of the locking member 400; FIG. 4B is a perspective bottom view of the locking member 400; FIG. 4C is a top view of the locking member 400; FIG. 4D is a bottom view of the locking member 400; FIG. 4E illustrates a first side of the locking member 400; and FIG. 4F illustrates a second side of the locking member 400 of FIG. 4A.

The locking member 400 may generally include a proximal end 405 with a first anti-backout member 401 and a second anti-backout member 402, a distal end 404 including a collet 410, and a driver engagement channel 460 that extends through the proximal and distal ends 405, 404 of the locking member 400.

The first and second anti-backout members 401, 402 may protrude radially away from the locking member 400. The first and second anti-backout members 401, 402 may also include angled engagement surfaces 407, 408 configured to engage the second pair of stop surfaces 348 formed in the intervertebral spacer 300. The second pair of stop surfaces 348 may also include complementarily shaped angled surfaces configured to receive the angled engagement surfaces 407, 408 of the first and second anti-backout members 401, 402.

The collet 410 may include a peripheral wall 420 with one or more slits 430 formed therein. In the example shown in FIGS. 4A-4F, the peripheral wall 420 of the collet 410 includes four slits 430 which are regularly spaced apart from each other. However, it will be understood that any number of slits 430 spaced apart from each other at any distance, arrangement, or pattern may also be utilized. The collet 410 may also include an annular flange 440 at its distal end which may be configured to be retained by the annular ridge 346 of the locking member channel 340 in order to rotatably couple the locking member 400 to the intervertebral spacer 300. For example, as the collet 410 of the locking member 400 is inserted into the locking member channel 340 of the intervertebral spacer 300 (e.g., see FIG. 6A), the slits 430 of the collet 410 will permit the collet 410 to compress inwardly to allow the annular flange 440 of the collet 410 to pass distally, beyond the annular ridge 346 that is formed in the inner wall 345 of the locking member channel 340. Once the annular flange 440 of the collet 410 has moved distal to the annular ridge 346, the collet 410 will expand outwardly again and the annular ridge 346 will retain the annular flange 440 of the collet 410 in order to rotatably couple the locking member 400 to the intervertebral spacer 300.

However, other embodiments for rotatably coupling the locking member 400 to the intervertebral spacer 300 are also contemplated herein. For example, in one embodiment contemplated herein (not shown), the locking member channel 340 may include an integral collet member configured to couple a shaft protruding from a locking member. The shaft protruding from the locking member may further include a ridge that may interact with the integral collet member within the intervertebral spacer in order to rotatably couple the locking member to the intervertebral spacer. In another example embodiment contemplated herein (not shown), a shaft protruding from a locking member may be rotatably coupled to an intervertebral spacer via a fastening member that can couple the locking member to the intervertebral spacer while allowing for rotation of the locking member (e.g., a rivet, a nut, a bolt, a screw, etc.).

Returning to FIGS. 4A-4F, the peripheral wall 420 of the collet 410 may include a first stop protrusion 451 projecting from a first side of the peripheral wall 420, and a second stop protrusion 452 projecting from a second side of the peripheral wall 420, opposite the first stop protrusion 451. Once the locking member 400 is rotatably coupled to the intervertebral spacer 300, as discussed above, the locking member 400 can be rotated within the locking member channel 340 between at least two stable positions comprising an unlocked position and a locked position. In the unlocked position, the first and second stop protrusions 451, 452 may protrude into the first pair of recesses 341 in order to retain the locking member 400 in the unlocked position, such that the first and second anti-backout members 401, 402 do not obstruct the first and second fastener channels 331, 332 (e.g., see FIG. 7A). In the locked position, the first and second stop protrusions 451, 452 may protrude into the second pair of recesses 342 in order to retain the locking member 400 in the locked position, such that the first and second anti-backout members 401, 402 obstruct the first and second fastener channels 331, 332 and prevent the first and second fasteners or bone screws 701, 702 from backing out of the first and second fastener channels 331, 332 (e.g., see FIGS. 7B and 7C for two example locked positions).

However, it will also be understood that other embodiments are contemplated herein in order to position and maintain the locking member 400 in either the unlocked or locked positions. For example, the inner wall 345 of the locking member channel 340 may comprise one or more inner wall engagement features that may engage with one or more collet engagement features formed on the collet 410 in order to retain the locking member 400 in either the unlocked or locked position, independently of any additional component besides the locking member 400 and the intervertebral spacer 300, such that one or more anti-backout members 401, 401 may selectively obstruct the one or more fastener channels 331, 332. In this example, the one or more inner wall engagement features may comprise one or more recesses or one or more protrusions. Likewise, the one or more collet engagement features may comprise one or more recesses or one or more protrusions that are complementarily shaped to the one or more inner wall engagement features. In this manner, in the unlocked position, the one or more collet engagement features may engage with the one or more inner wall engagement features in order to retain the locking member 400 in the unlocked position, independently of any additional component besides the locking member 400 and the intervertebral spacer 300, and the one or more anti-backout members 401, 402 may not obstruct the one or more fastener channels 331, 332. Likewise, in the locked position, the one or more collet engagement features may engage with the one or more inner wall engagement features to retain the locking member 400 in the locked position, independently of any additional component besides the locking member 400 and the intervertebral spacer 300, and the one or more anti-backout members 401, 402 may obstruct the one or more fastener channels 331, 332 in order to prevent the one or more fasteners or bone screws 701, 702 from backing out of the one or more fastener channels 331, 332.

FIGS. 8A-19 illustrate various views of surgical instruments, tools, and assemblies that may be utilized to implant an intervertebral spacer of the present disclosure.

Figure 8A:
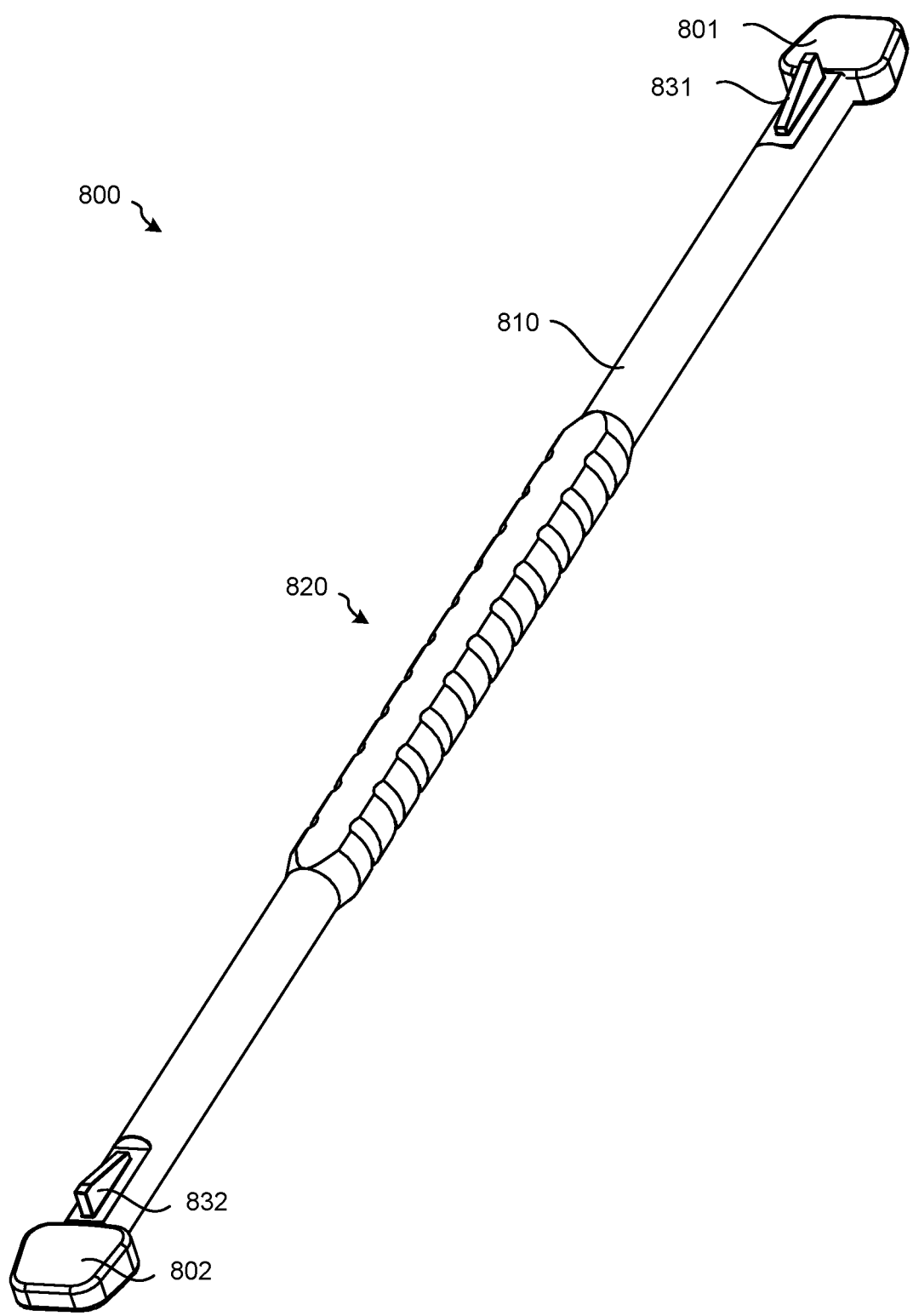
FIG. 8A is a perspective top view of a trial tool, according to an embodiment of the present disclosure.
Figure 8B:
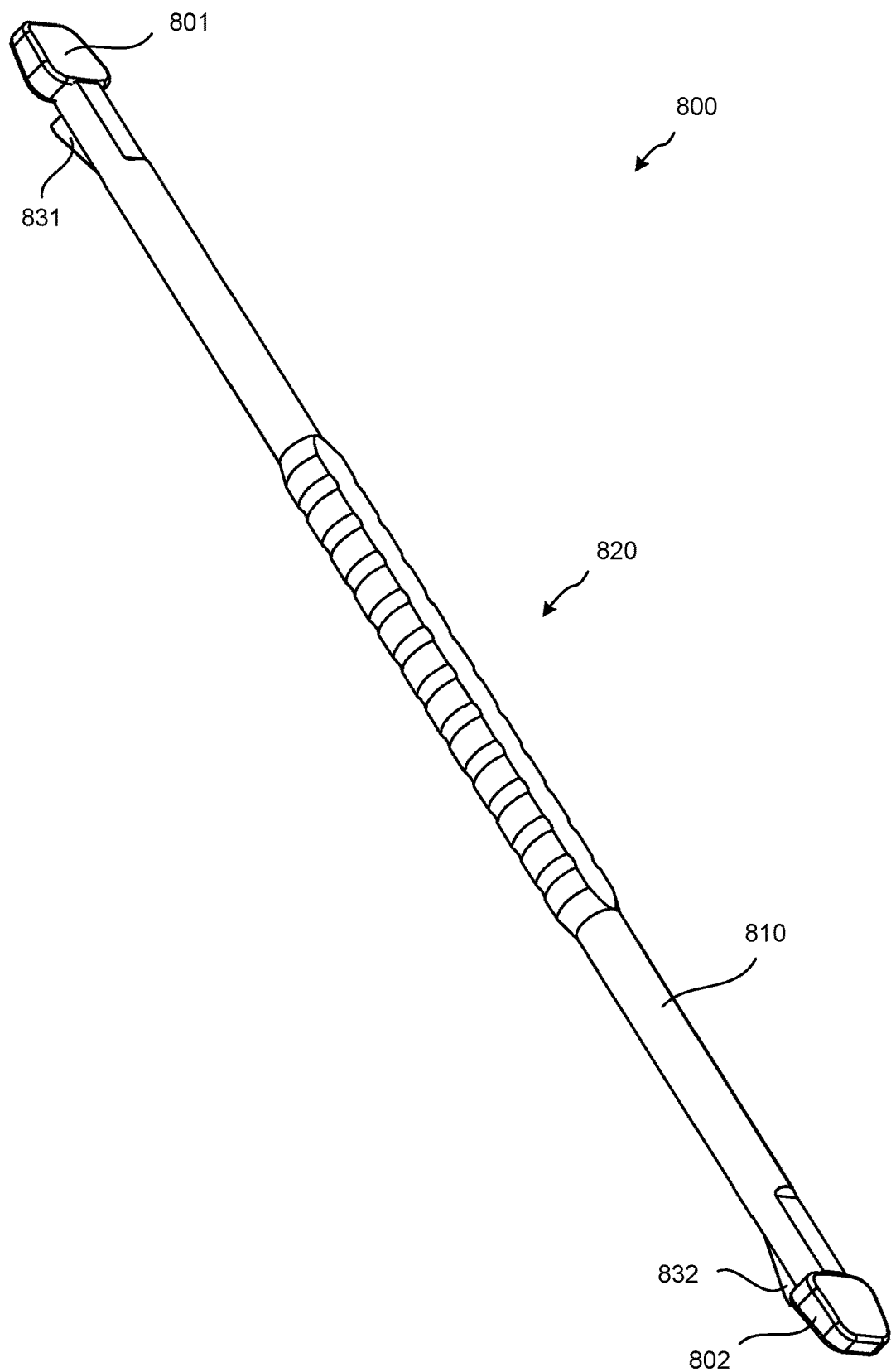
FIG. 8B is a perspective bottom view of the trial tool of FIG. 8A.

FIGS. 8A and 8B are perspective top and bottom views of an example trial tool 800 which may be utilized during a surgical procedure to implant an intervertebral spacer 300. For example, once a surgeon has created a space between two vertebral bodies for the intervertebral spacer 300 (e.g., by removing at least a portion of an intervertebral disc), the surgeon may utilize the trial tool 800 (or another trial tool from a set of trial tools having different sizes) in order to ascertain which size of intervertebral spacer 300 should be implanted in the prepared disc space between the two vertebral bodies.

As shown in FIGS. 8A and 8B, the trial tool 800 may generally comprise a trial shaft 810, a handle portion 820, a first trial component 801 having a first size, a first trial depth stop 831 adjacent the first trial component 801, a second trial component 802 having a second size, and a second trial depth stop 832 adjacent the second trial component 802. The first and second trial depth stops 831, 832 may contact at least one of the vertebral bodies in order to prevent the first and second trial components 801, 801 from being inserted too far inside the prepared disc space.

Figure 9A:
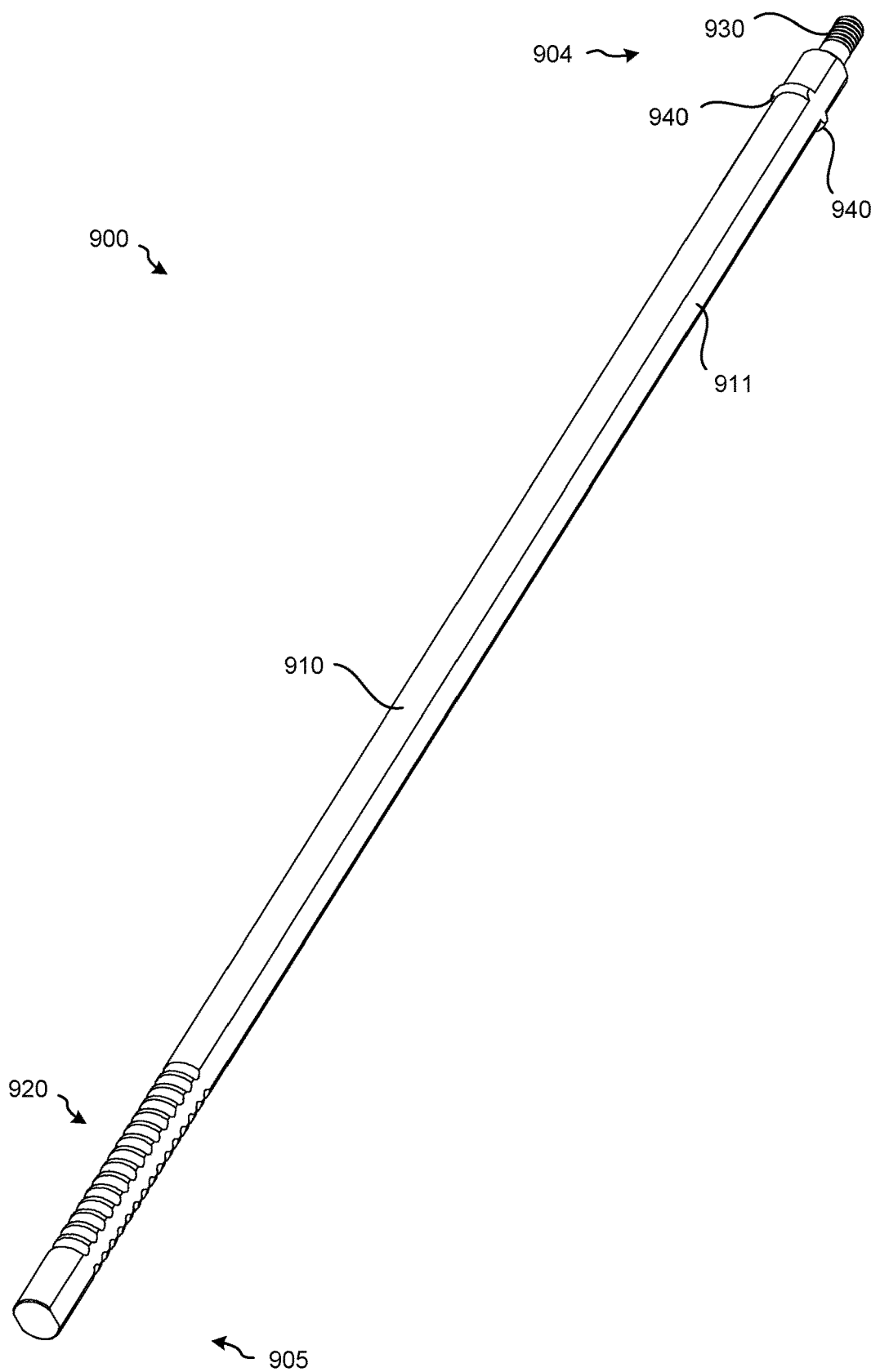
FIG. 9A is a perspective top view of an inserter tool, according to an embodiment of the present disclosure.
Figure 9B:
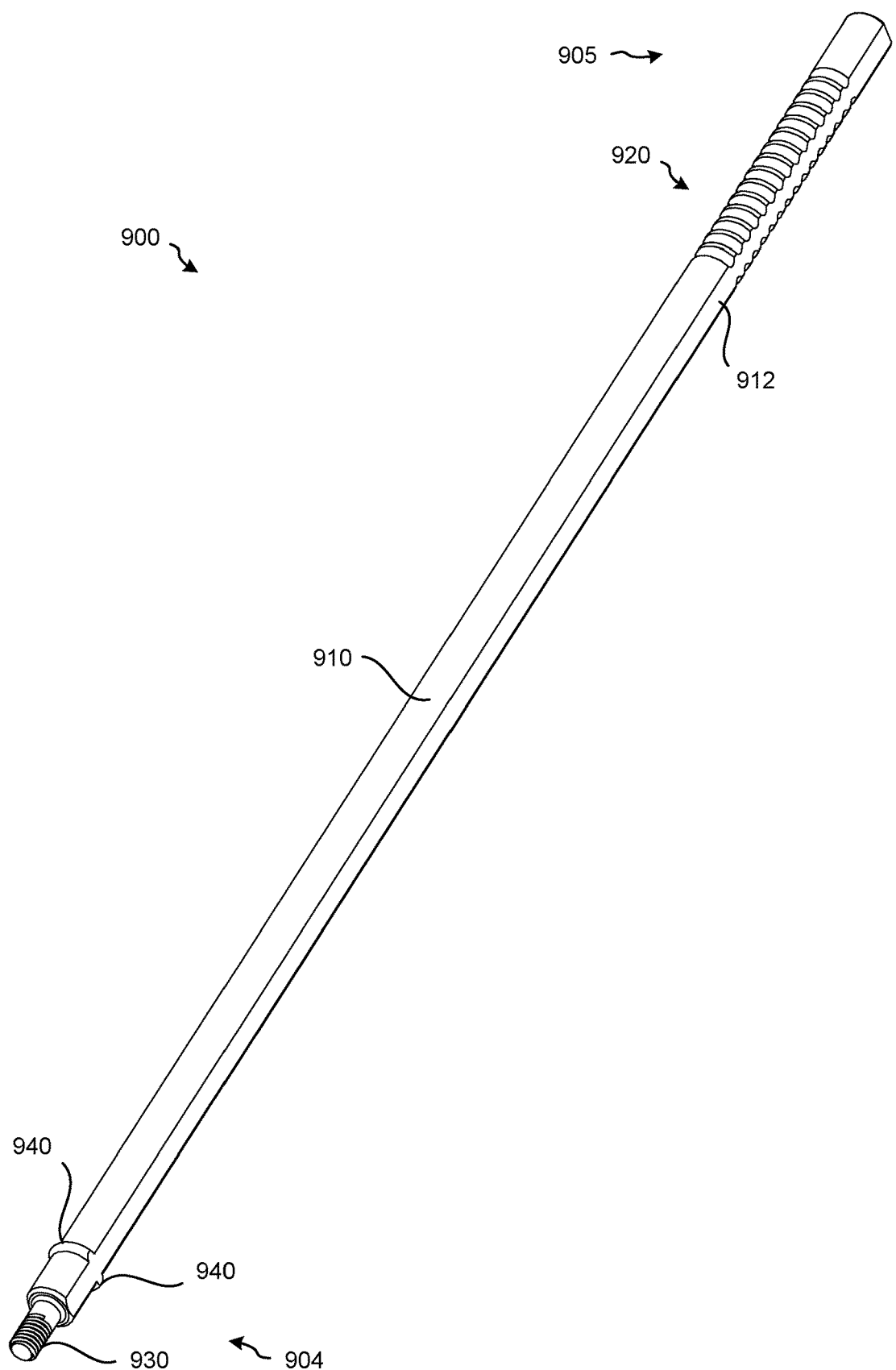
FIG. 9B is a perspective bottom view of the inserter tool of FIG. 9A.
Figures 9C, 9D, 9E:
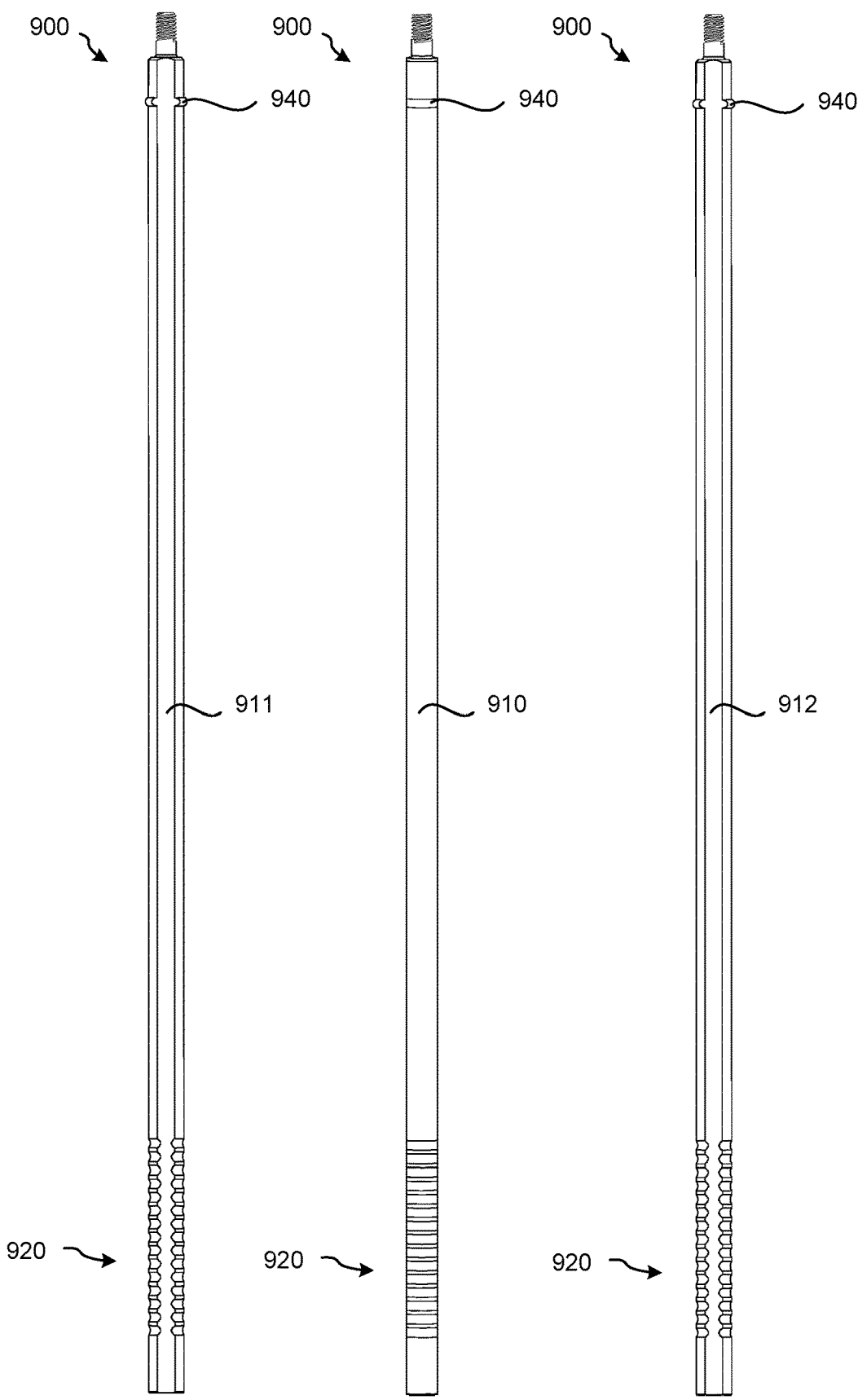
FIG. 9C is a top view of the inserter tool of FIG. 9A.
FIG. 9D is a side view of the inserter tool of FIG. 9A.
FIG. 9E is a bottom view of the inserter tool of FIG. 9A.

FIGS. 9A-9E illustrate various views of an inserter tool 900, according to an embodiment of the present disclosure. Specifically, FIG. 9A is a perspective top view of the inserter tool 900; FIG. 9B is a perspective bottom view of the inserter tool 900; FIG. 9C is a top view of the inserter tool 900; FIG. 9D is a side view of the inserter tool 900; and FIG. 9E is a bottom view of the inserter tool 900. The inserter tool 900 may generally include a shaft 910 having a proximal end 905 and a distal end 904, a first flat surface 911, a second flat surface 912, recesses 920, ridges 940, and second threading 930.

Figure 10A:
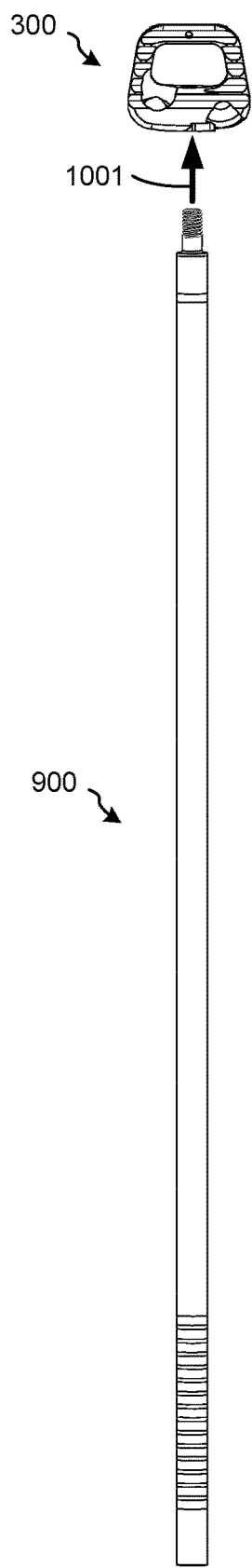
FIG. 10A illustrates an insertion assembly including the inserter tool and the intervertebral spacer, prior to assembly.
Figure 10B:
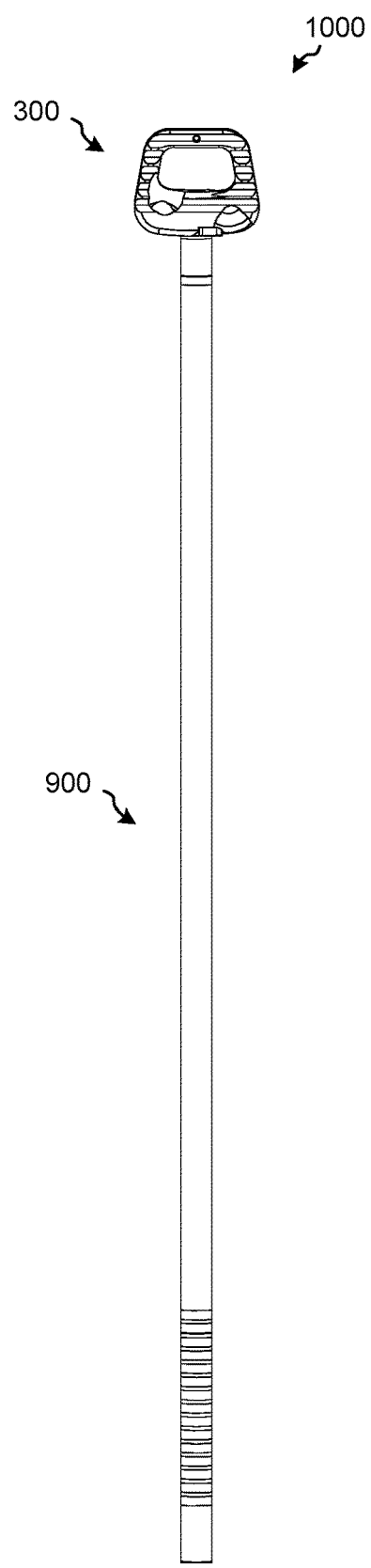
FIG. 10B illustrates the insertion assembly, after assembly.

FIGS. 10A and 10B illustrate how the inserter tool 900 and the intervertebral spacer 300 may be coupled together to form an insertion assembly 1000. Specifically, the distal end 904 of the inserter tool 900 comprising the second threading 930 may be moved distally (e.g., in the direction of arrow 1001), such that the distal end 904 of the inserter tool 900 may pass through the driver engagement channel 460 formed through the locking member 400. The second threading 930 may then be engaged with the first threading 344 within the locking member channel 340 of the intervertebral spacer 300 in order to couple the intervertebral spacer 300 to the inserter tool 900. In at least one embodiment, the insertion assembly 1000 comprises the intervertebral spacer 300 preassembled onto the inserter tool 900, which may then be packaged within a sterile container.

Figure 11A:
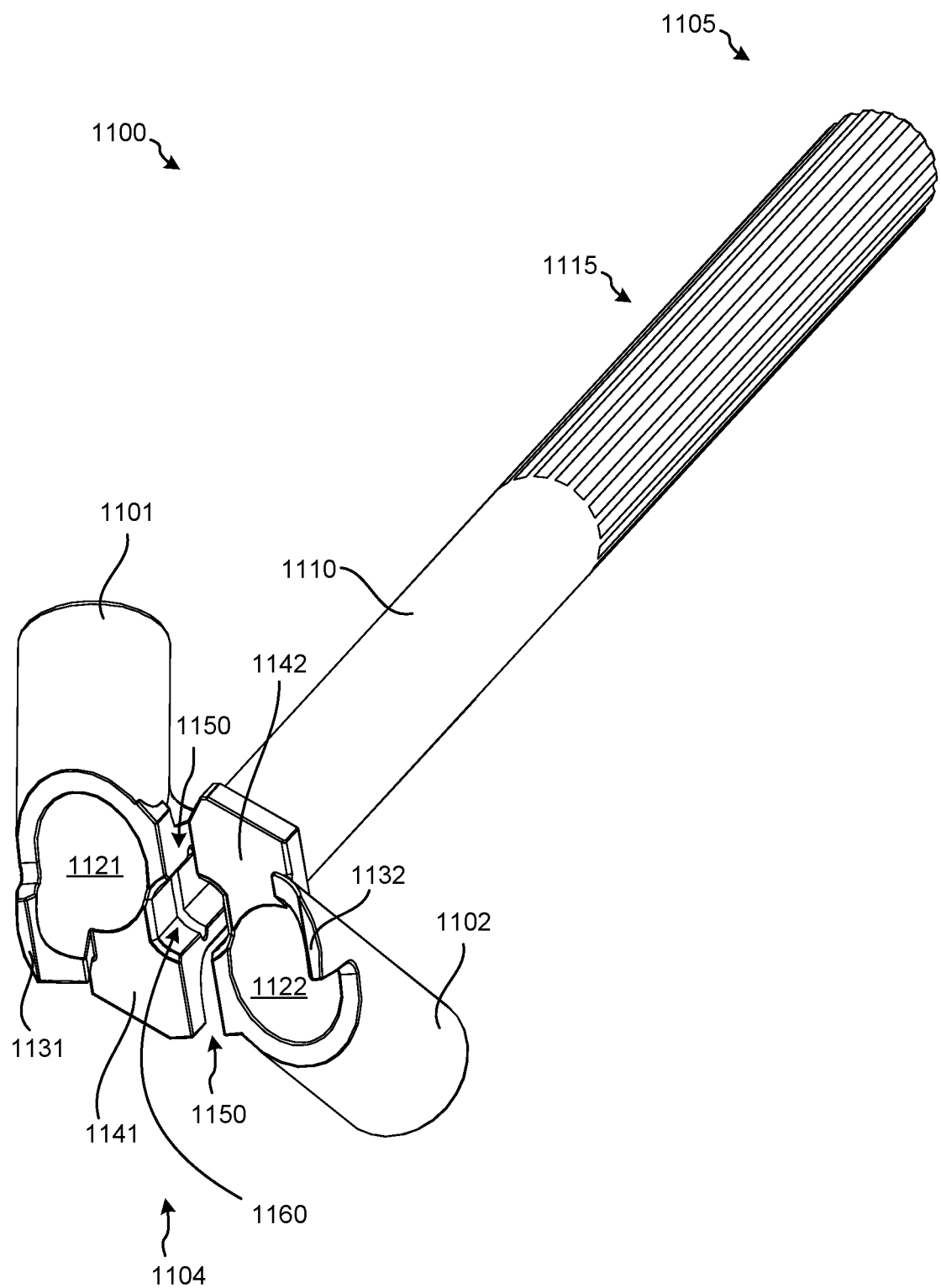
FIG. 11A is a perspective top view of a DTS guide, according to an embodiment of the present disclosure.
Figure 11B:
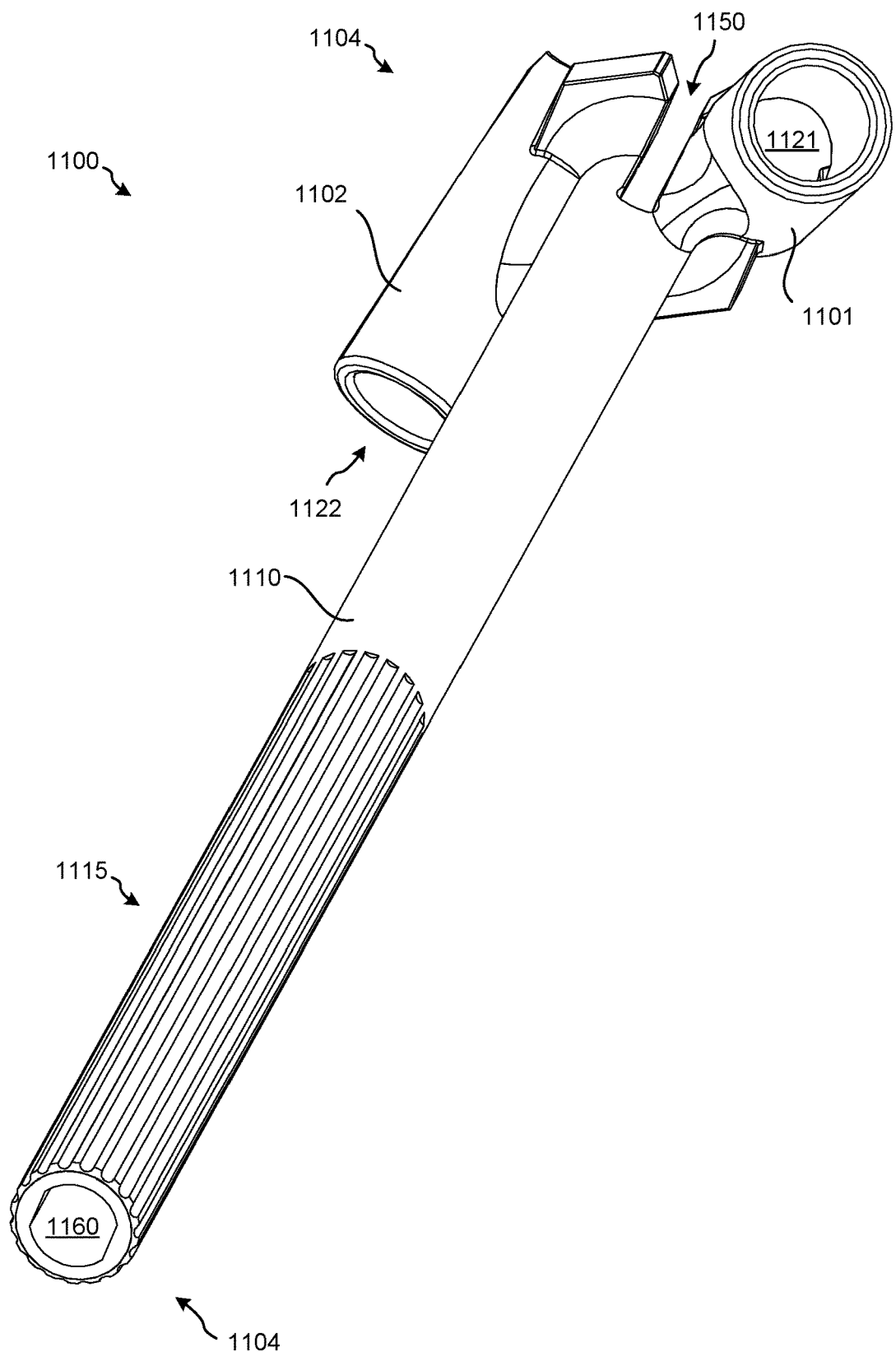
FIG. 11B is a perspective bottom view of the DTS guide of FIG. 11A.
Figure 11E:
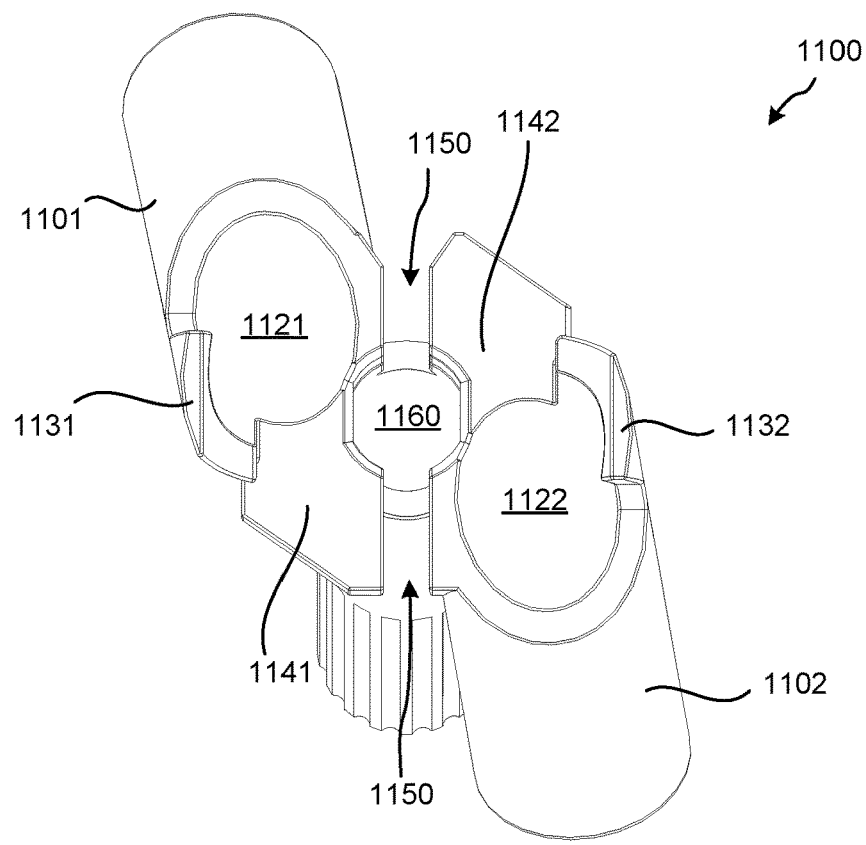
FIG. 11E is a proximal end view of the DTS guide of FIG. 11A.
Figure 11F:
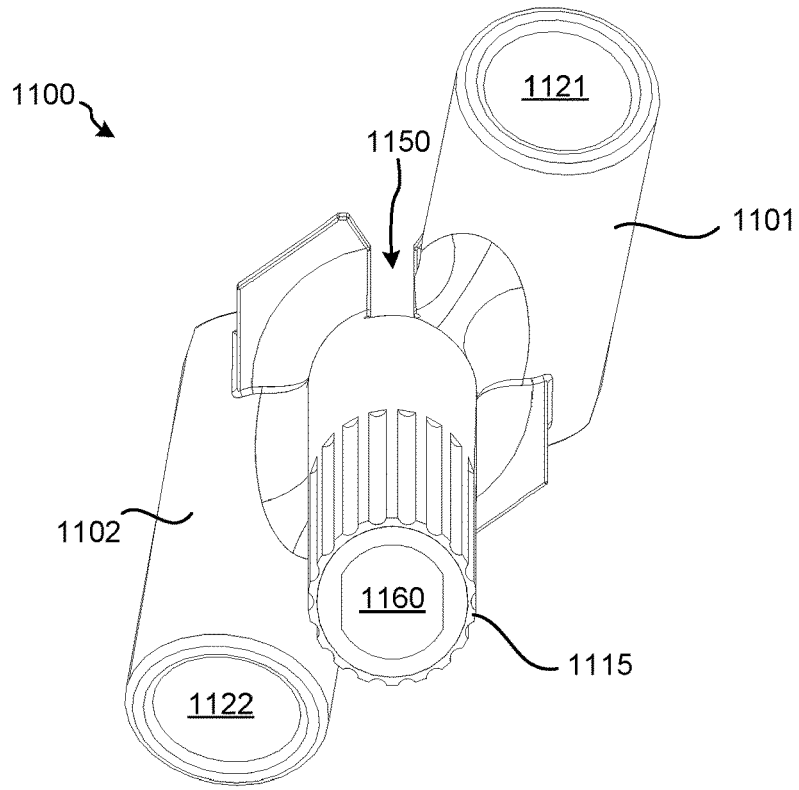
FIG. 11F is a distal end view of the DTS guide of FIG. 11A.

FIGS. 11A-11F illustrate various views of a DTS guide 1100, according to an embodiment of the present disclosure. Specifically, FIG. 11A is a perspective top view of the DTS guide 1100; FIG. 11B is a perspective bottom view of the DTS guide 1100; FIG. 11C is a top view of the DTS guide 1100; FIG. 11D is a bottom view of the DTS guide 1100; FIG. 11E is a proximal end view of the DTS guide 1100; and FIG. 11F is a distal end view of the DTS guide 1100.

The DTS guide 1100 may generally include a proximal end 1105, a distal end 1104, a DTS guide shaft 1110, a first DTS guide member 1101 having a first DTS guide channel 1121, a second DTS guide member 1102 having a second DTS guide channel 1122, an intermediate channel 1150, a first DTS guide wing 1131, a second DTS guide wing 1132, a first depth stop surface 1141, and a second depth stop surface 1142. Each different size of intervertebral spacer disclosed herein may be paired with a corresponding different size of DTS guide.

The DTS guide shaft 1110 may be hollow and have a "double D" shaped DTS guide shaft lumen 1160 that is configured to receive the inserter tool shaft 910, which may also have a complementary "double D" shape due to the first and second flat surfaces 911, 912 formed in the inserter tool shaft 910. The DTS guide shaft 1110 may also include one or more shaft splines 1115, as will be discussed in more detail below with respect to FIGS. 16A and 16B.

Figure 12A:
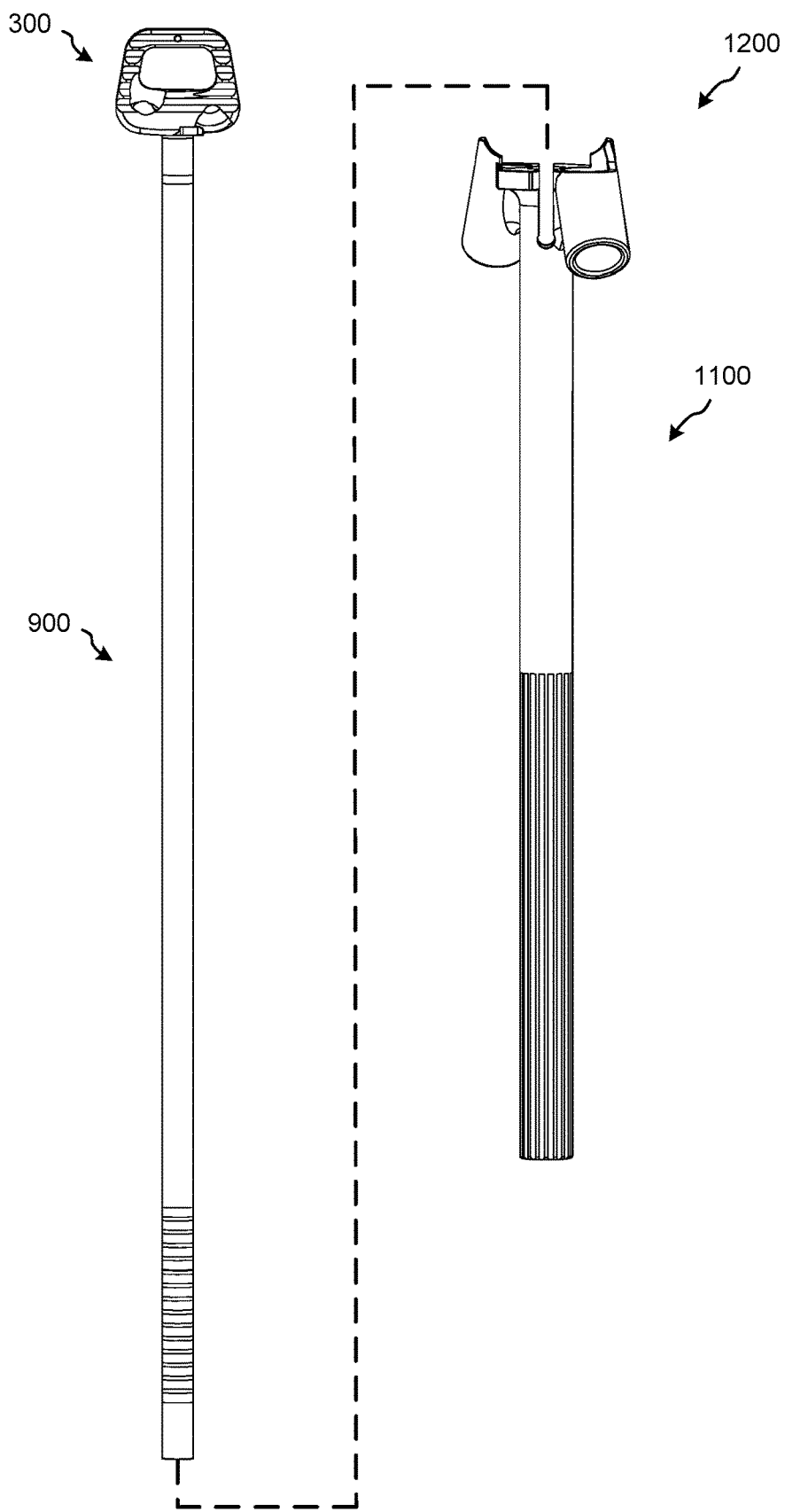
FIG. 12A is an exploded view of an insertion assembly including the inserter tool, the intervertebral spacer, and the DTS guide, prior to assembly.
Figure 12B:
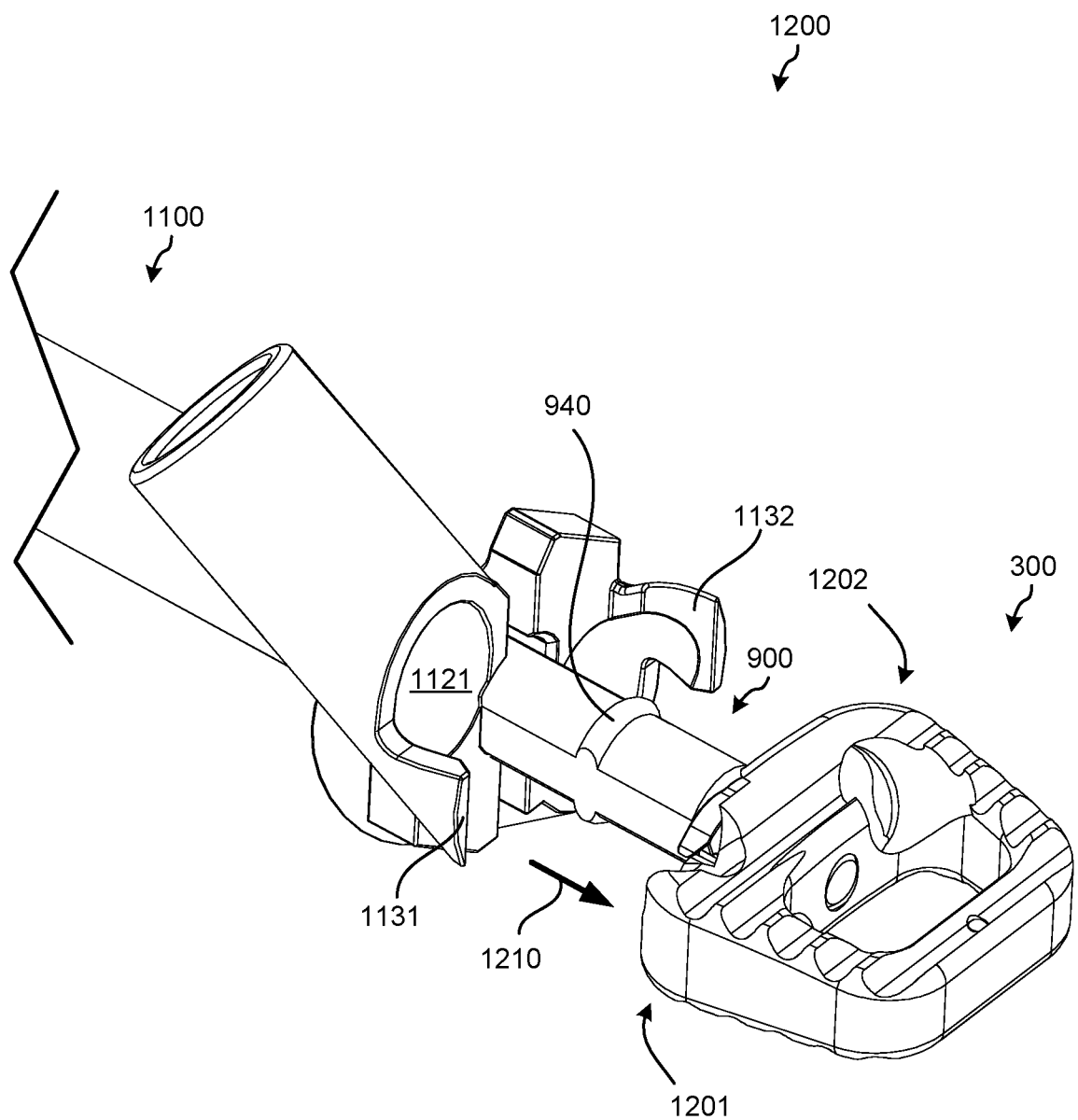
FIG. 12B is a close up view of the distal end of the insertion assembly illustrating the DTS guide engaging with the intervertebral spacer.
Figure 12C:
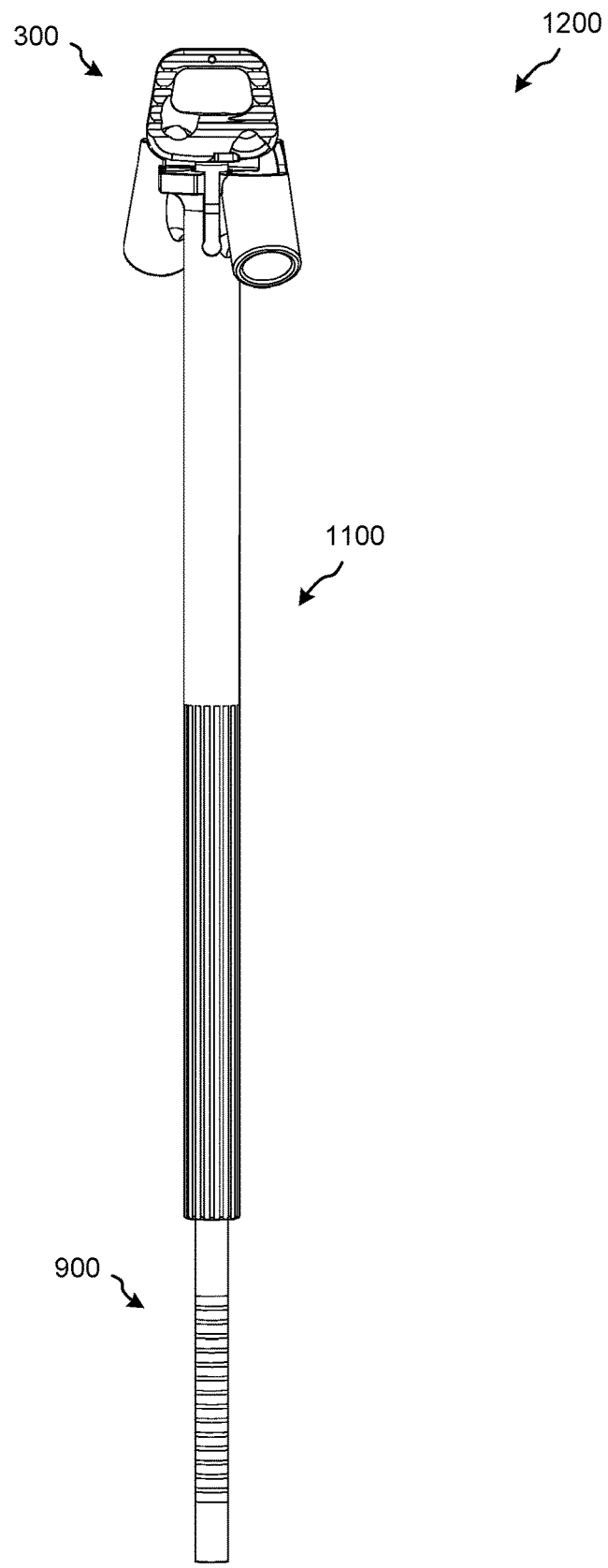
FIG. 12C is a top view of the insertion assembly of FIG. 12A, after assembly.

FIGS. 12A-12C illustrate how the DTS guide 1100 may be coupled with the inserter tool 900 and the intervertebral spacer 300 to form an insertion assembly 1200. Specifically, FIG. 12A is an exploded view of the insertion assembly 1200 prior to assembly; FIG. 12B is a close up view of the distal end of the insertion assembly 1200 as the DTS guide 1100 is moved distally to engage the intervertebral spacer 300; and FIG. 12C is a top view of the insertion assembly 1200 after assembly.

In general, the DTS guide shaft lumen 1160 is configured to receive the inserter tool shaft 910 to slidably couple the DTS guide 1100 with the inserter tool 900. The ridges 940 formed on the inserter tool 900 may couple with recesses (not shown) formed within the DTS guide shaft lumen 1160 in order to removably couple the DTS guide 1100 to the inserter tool 900. As the DTS guide 1100 moves distally (e.g., see Arrow 1210 in FIG. 12B) to couple with the inserter tool 900, the first and second DTS guide wings 1131, 1132 will engage the intervertebral spacer 300 and impart forces on the intervertebral spacer 300 that will act to correctly orient the DTS guide 1100 with respect to the intervertebral spacer 300. In this manner, the first and second DTS guide channels 1121, 1122 will assume a correct alignment with respect to the first and second fastener channels 331, 332 of the intervertebral spacer 300. More specifically, the first DTS guide wing 1131 may be configured to abut against a first surface 1201 of the intervertebral spacer 300, and the second DTS guide wing 1132 may be configured to abut against a second surface 1202 of the intervertebral spacer 300, in order to align the first and second DTS guide channels 1121, 1122 with the first and second fastener channels 331, 332 of the intervertebral spacer 300. Thus, the first DTS guide channel 1121 will be correctly aligned and configured to receive the first fastener or bone screw 701 at the first angle 711 in order to guide the bone screw 701 into the first fastener channel 331 of the intervertebral spacer 300, and the second DTS guide channel 1122 will be configured to receive the second fastener or bone screw 702 at the second angle 712 in order to guide the second bone screw 702 into the second fastener channel 332 of the intervertebral spacer 300.

It will be noted that the first and second DTS guide wings 1131, 1132 may be configured to align the first and second DTS guide channels 1121, 1122 with respect to the first and second fastener channels 331, 332, independently of any additional apertures or recesses formed in the intervertebral spacer 300. It will also be noted that intervertebral spacers of different sizes may be paired with DTS guides of a corresponding size. Moreover, in at least one embodiment, the insertion assembly 1200 may comprise the intervertebral spacer 300 and the DTS guide 1100 preassembled onto the inserter tool 900, which may then be packaged within a sterile container.

Figure 13A:
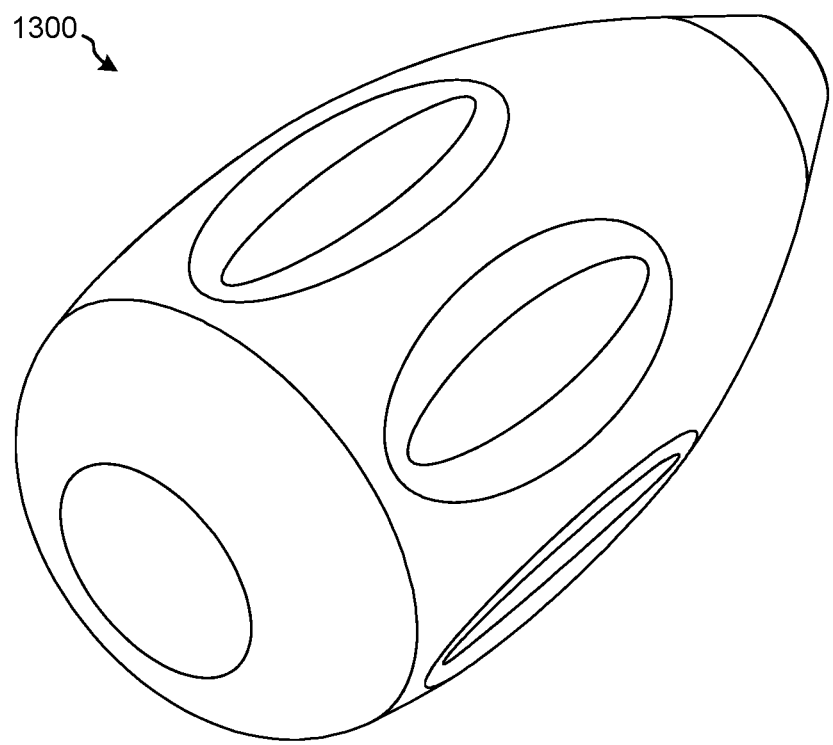
FIG. 13A is a perspective top view of a handle, according to an embodiment of the present disclosure.
Figure 13B:
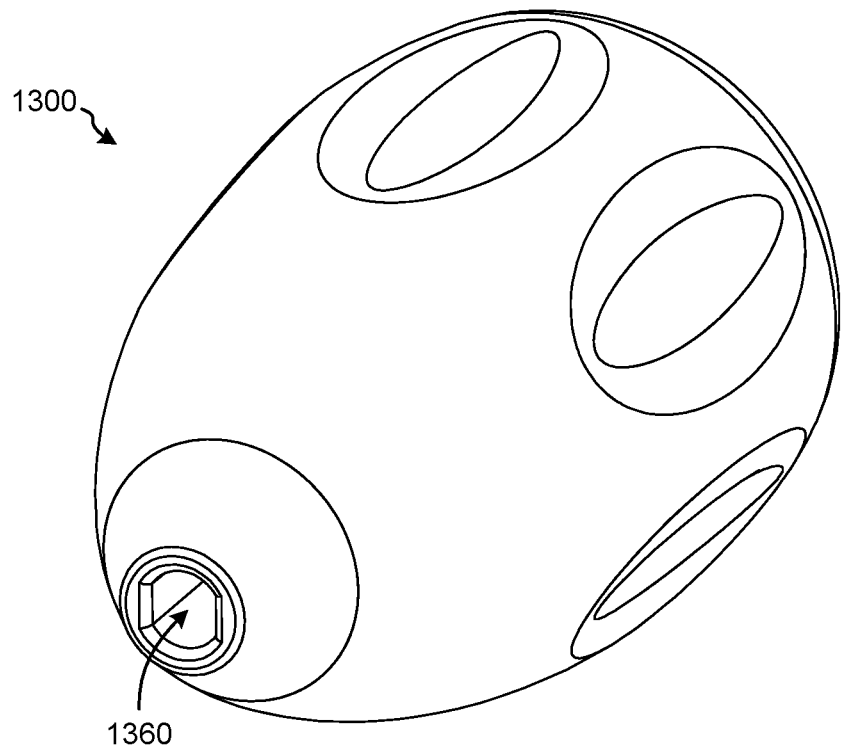
FIG. 13B is a perspective bottom view of the handle of FIG. 13A.

FIGS. 13A and 13B illustrate perspective top and bottom views of a handle 1300 that may be utilized with the insertion assembly 1200 of FIGS. 12A-12C, according to an embodiment of the present disclosure. The handle 1300 may have a "double D" shaped lumen 1360 that is configured to receive the "double D" shaped inserter tool shaft 910.

Figure 14A:
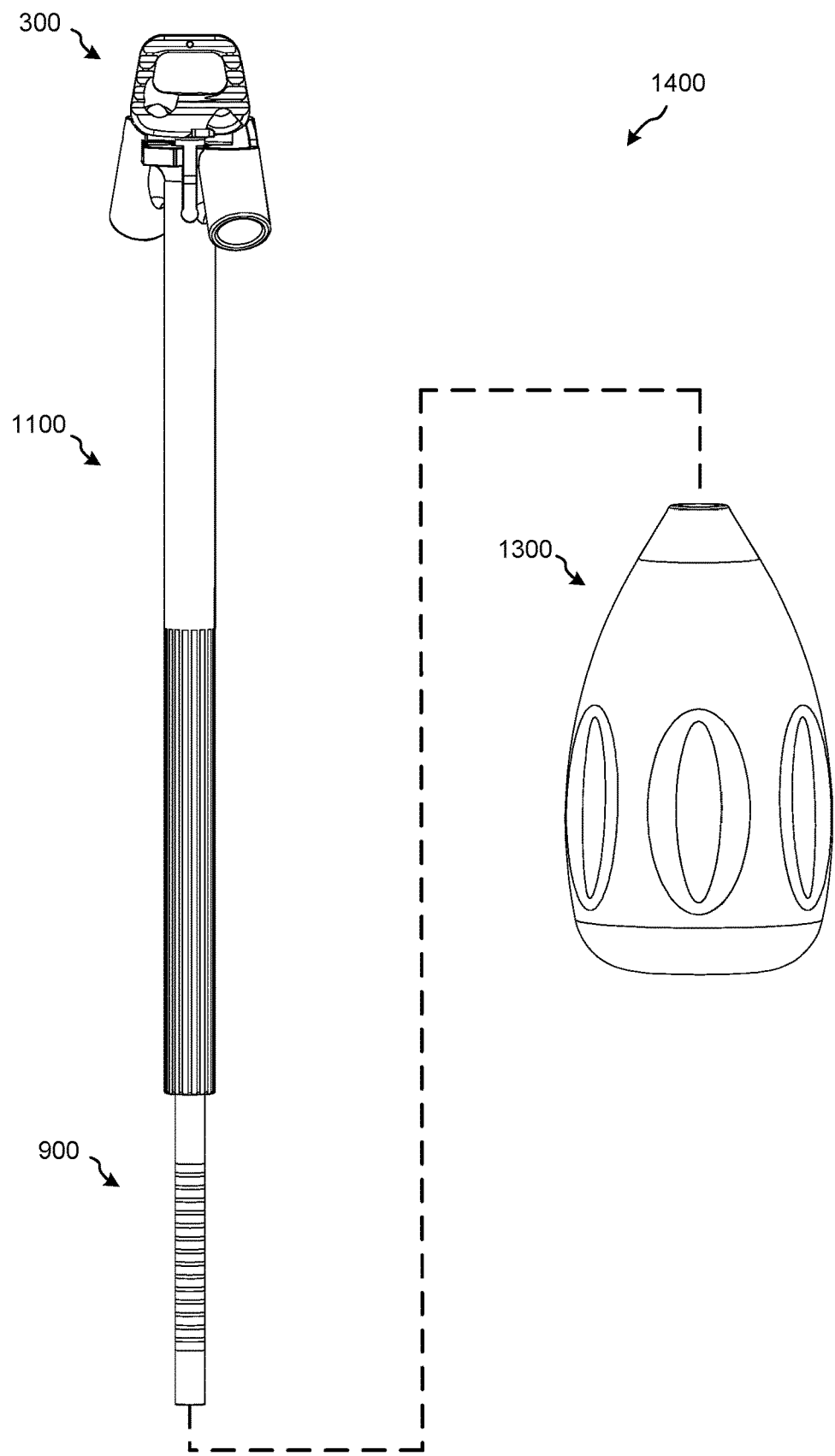
FIG. 14A is an exploded view of an insertion assembly including the inserter tool 900, the intervertebral spacer, the DTS guide, and the handle, prior to assembly.
Figure 14B:
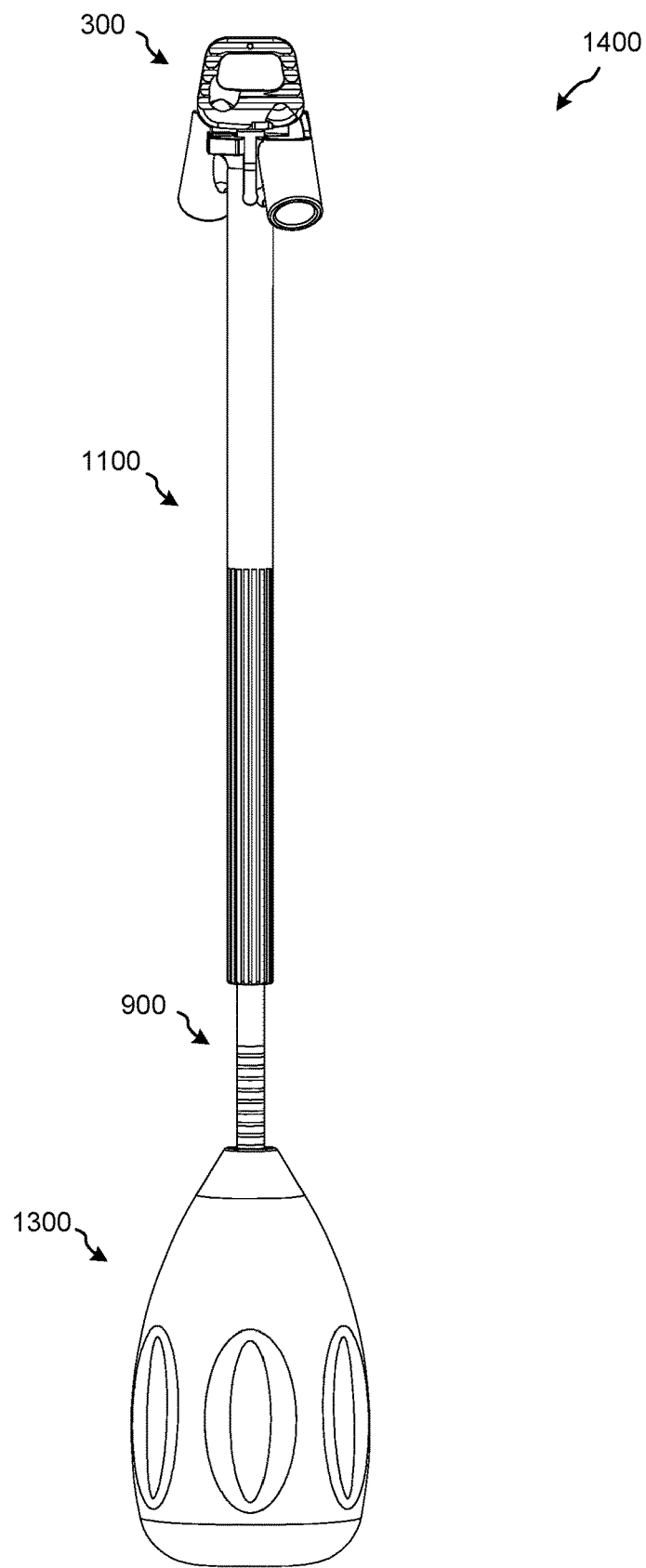
FIG. 14B is a top view of the insertion assembly of FIG. 14A, after assembly.

FIGS. 14A and 14B illustrate how the handle 1300 may be coupled with the inserter tool 900, which itself may be coupled with the intervertebral spacer 300 and the DTS guide 1100, in order to form an insertion assembly 1400. The surgeon may then utilize the insertion assembly 1400 to insert the intervertebral spacer 300 between two vertebral bodies of a patient by using the handle to manipulate the intervertebral spacer 300 into place. The surgeon may also utilize an impact tool (not shown) to strike the proximal end of the handle 1300 and drive the intervertebral spacer 300 into place. The first and second depth stop surfaces 1141, 1142 of the DTS guide 1100 may help prevent the surgeon from inserting the intervertebral spacer 300 too far into the prepared disc space between the two vertebral bodies. Once the intervertebral spacer 300 has been properly placed between the two vertebral bodies, the surgeon may remove the handle 1300 from the insertion assembly 1400.

Figure 15A:
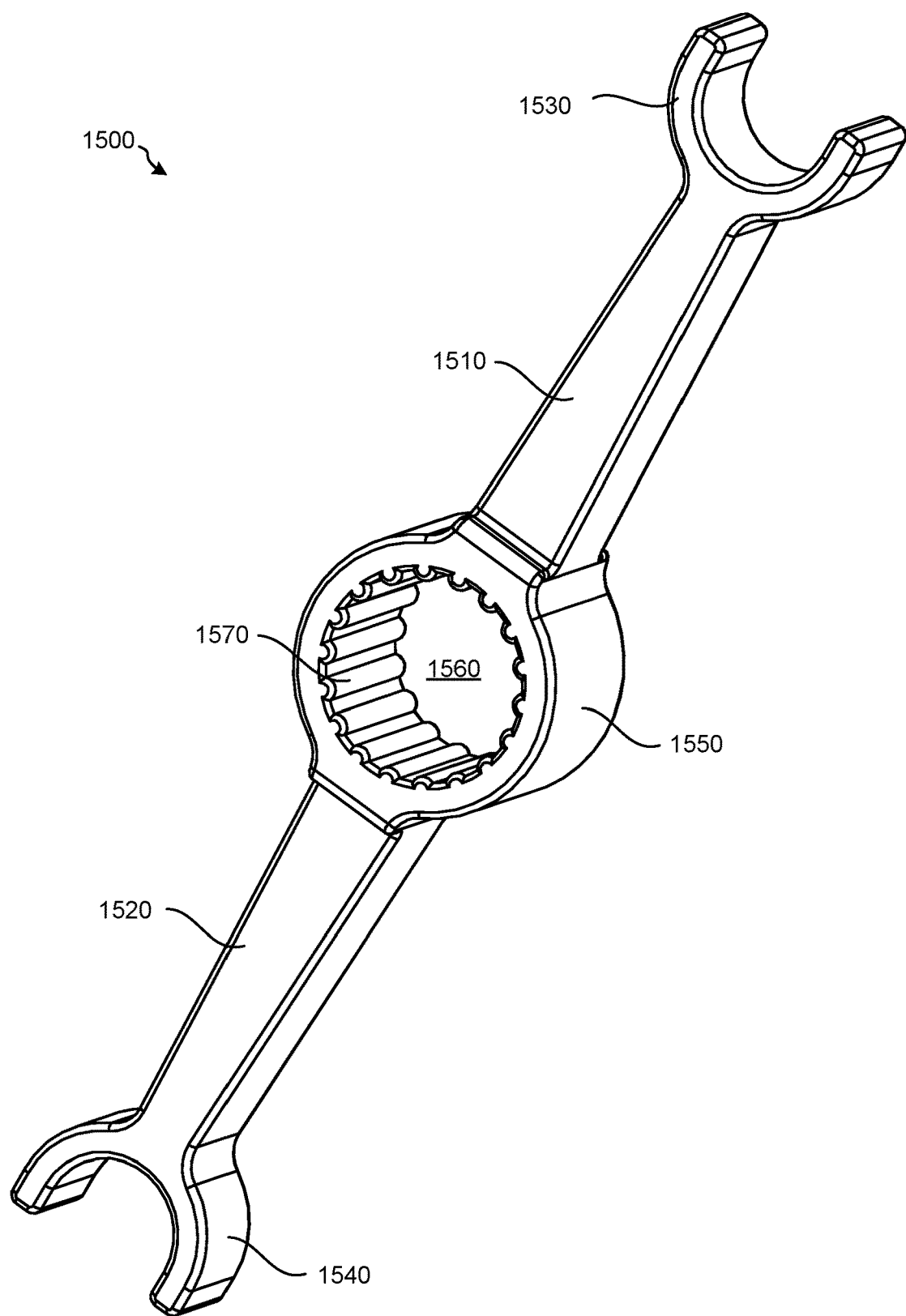
FIG. 15A is a perspective view of a U-support tool, according to an embodiment of the present disclosure.

FIGS. 15A-15D illustrate various views of a U-support tool 1500 that may be utilized with the insertion assembly 1200 of FIG. 12B. Specifically, FIG. 15A is a perspective view of the U-support tool 1500; FIG. 15B is a front side view of the U-support tool 1500; FIG. 15C is a top view of the U-support tool 1500; and FIG. 15D is a left side view of the U-support tool 1500. The U-support tool 1500 may generally include a first arm 1510 having a first U-support 1530, a second arm 1520 having a second U-support 1540, and a ring member 1550 intermediate the first and second arms 1510, 1520 including a ring channel 1560 with one or more ring splines 1570 formed therein.

Figure 16A:
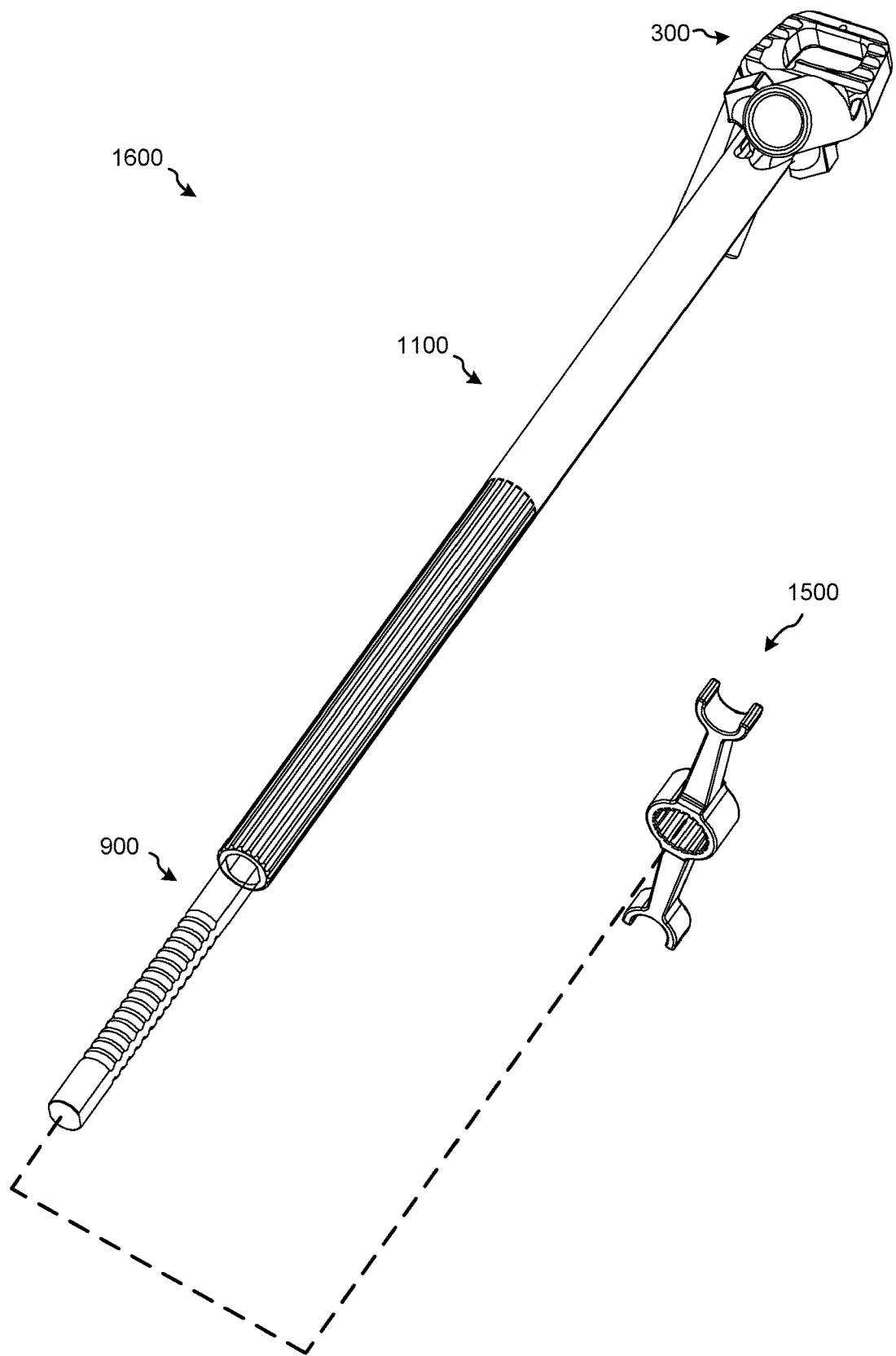
FIG. 16A is an exploded view of an insertion assembly including the inserter tool, the intervertebral spacer, the DTS guide, and the U-support tool, prior to assembly.
Figure 16B:
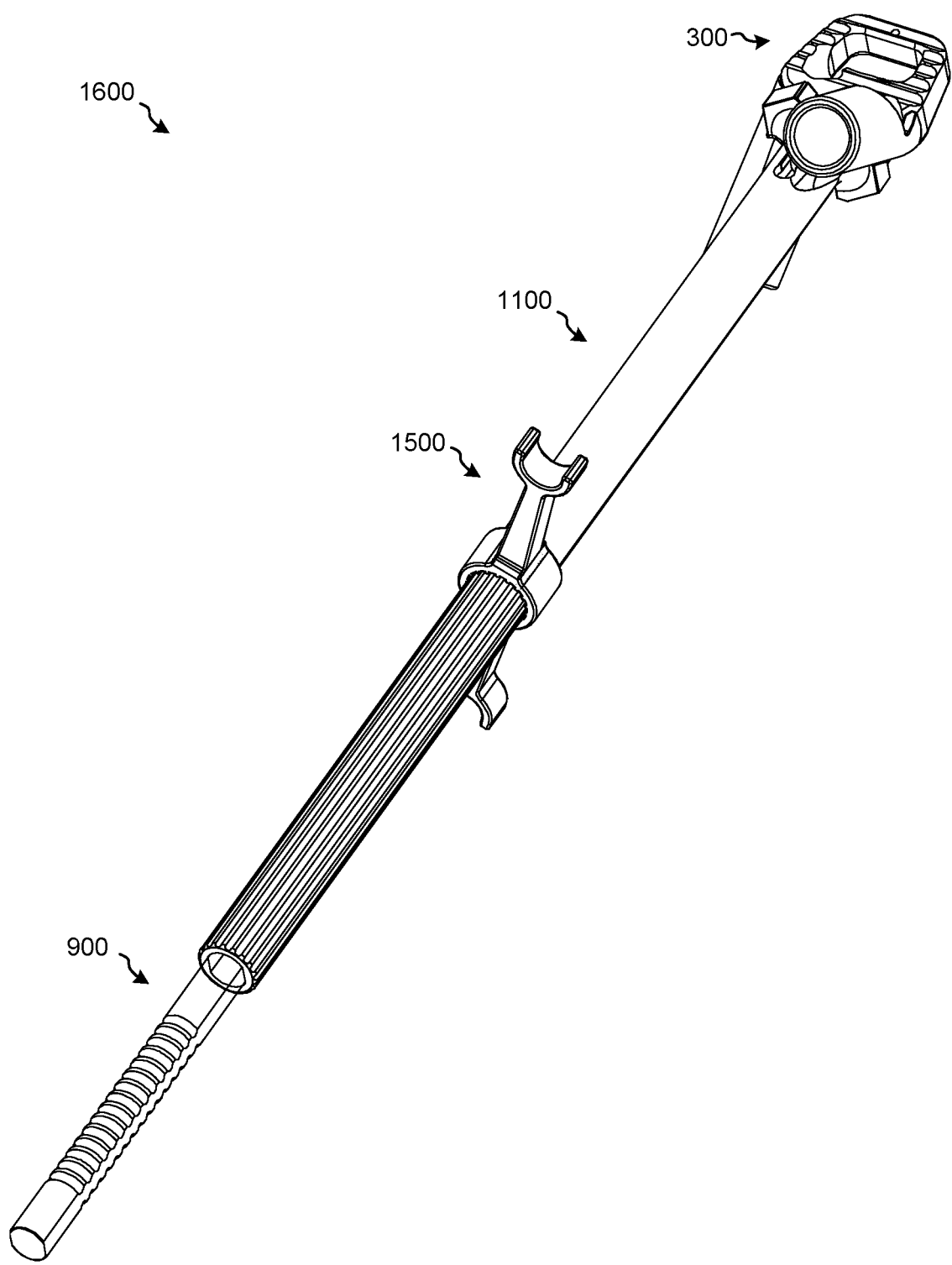
FIG. 16B is a perspective view of the insertion assembly of FIG. 16A, after assembly.

FIGS. 16A and 16B illustrate how the U-support tool 1500 may be coupled to the DTS guide 1100 (which itself may be coupled to the inserter tool 900 and the intervertebral spacer 300) in order to form an insertion assembly 1600. The one or more ring splines 1570 may be configured to engage the one or more shaft splines 1115 formed on the DTS guide 1100 in order to couple the U-support tool 1500 to the DTS guide 1100 at a selected orientation. The U-support tool 1500 may be coupled to the DTS guide 1100 at one or more discrete orientations or angles by rotating the one or more ring splines 1570 relative to the one or more shaft splines 1115 before sliding the U-support tool 1500 onto the DTS guide 1100. The one or more ring splines 1570 and the one or more shaft splines 1115 may be shaped and spaced apart from each other according to any desired distance in order to achieve a desired set of discrete angles between the U-support tool 1500 and the DTS guide 1100. As one non-limiting example, the shape and spacing of the one or more ring splines 1570 and the one or more shaft splines 1115 may be chosen to achieve a set of different orientations that are about 15 degrees apart from each other.

Figure 17:
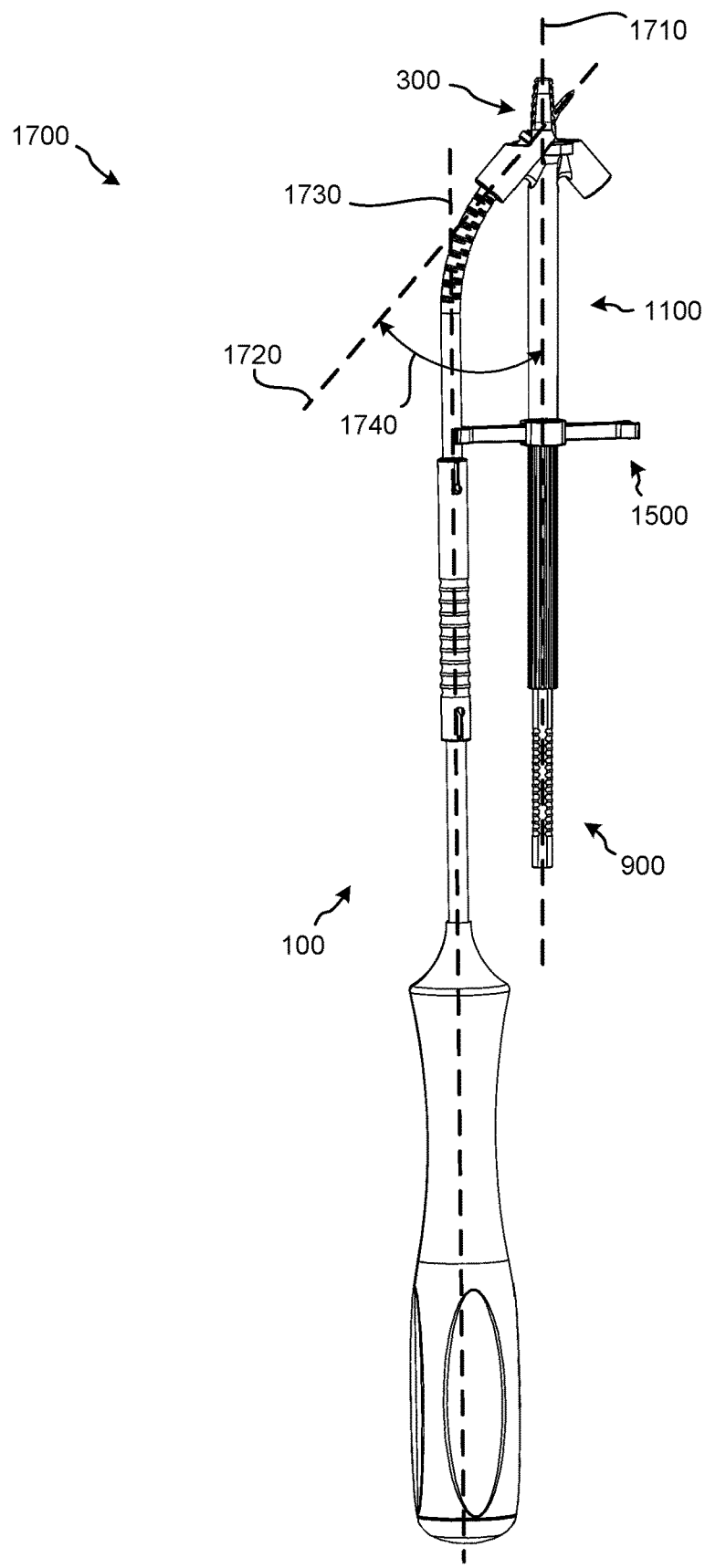
FIG. 17 illustrates an insertion assembly including the inserter tool, the intervertebral spacer, the DTS guide, the U-support tool, and the awl tool.

FIG. 17 illustrates an insertion assembly 1700 including the inserter tool 900, the intervertebral spacer 300, the DTS guide 1100, the U-support tool 1500, and the flexible awl tool 100 assembled together in order to form bone tunnels within vertebral bodies (not shown) adjacent the intervertebral spacer 300. The drill tip 140 of the flexible awl tool 100 can be guided by the DTS guide 1100 through the first and second guide channels 1121, 1122. The awl depth stop ring 150 may abut the first and second depth stops 333, 334 formed in the intervertebral spacer 300 to control the depth of the drill tip 140 that may protrude into the vertebral bodies adjacent the intervertebral spacer 300. The surgeon may also utilize the U-support tool 1500 to help guide the flexible awl shaft 110 of the flexible awl tool 100. For example, the surgeon may press the flexible awl shaft 110 of the flexible awl tool 100 against the U-support tool 1500 while he/she rotates the flexible awl tool 100 and drills bone tunnels into the vertebral bodies adjacent the intervertebral spacer 300. In this manner, a proximal portion of the flexible awl shaft 110 may remain closer to the inserter tool shaft 910 and/or the DTS guide shaft 1110 such that a smaller incision may be utilized during the surgical procedure.

In at least one embodiment, the drill tip 140 may be configured to be received through the first DTS guide channel 1121 at the first angle 711 and the second DTS guide channel 1122 at the second angle 712. Moreover, at least a portion of the flexible awl shaft 110 adjacent the first or second DTS guide members 1101, 1102 may be configured to flex while the drill tip 140 is received through the first or second DTS guide channels 1121, 1122. Additionally, the drill tip 140 received through the first or second DTS guide channels 1121, 1122 at the first or second angles 711, 712 may be at a greater absolute angle 1740 relative to the DTS guide shaft 1110 than a proximal portion of the flexible awl shaft 110. As defined herein, an absolute angle comprises a magnitude of an angle without regard to its sign (e.g., an absolute angle may be represented by a positive real number or zero). For example, FIG. 17 illustrates a DTS guide longitudinal axis 1710, a drill tip longitudinal axis 1720, and a flexible awl tool longitudinal axis 1730. Note how the absolute angle 1740 formed between the DTS guide longitudinal axis 1710 and the drill tip longitudinal axis 1720 is greater than an angle formed between a proximal portion of the flexible awl shaft 110 that lies along the flexible awl tool longitudinal axis 1730 and the DTS guide longitudinal axis 1710.

In at least one embodiment, a proximal portion of the flexible awl shaft 110 may be substantially parallel to the inserter tool shaft 910 and/or substantially parallel to the DTS guide shaft 1110 while the drill tip 140 is received through the first or second DTS guide channels 1121, 1122 at the first or second angles 711, 712.

In at least one embodiment, a proximal portion of the flexible awl shaft 110 may remain substantially parallel to the DTS guide shaft 1110 as the flexible awl shaft 110 is rotated about the flexible awl tool longitudinal axis 1730.

In at least one embodiment, the U-support tool 1500 may be coupled to the DTS guide shaft 1110 and configured to guide the flexible awl shaft 110 as it is rotated about the flexible awl tool longitudinal axis 1730 in order to maintain a proximal portion of the flexible awl shaft 110 substantially parallel to the DTS guide shaft 1110 as the flexible awl shaft 110 is rotated about the flexible awl tool longitudinal axis 1730.

Once the bone tunnels are formed in the vertebral bodies adjacent the intervertebral spacer 300, the flexible awl tool 100 may be removed from the patient in preparation for the next step in the procedure.

However, it will also be understood that in an alternative surgical procedure, the U-support tool 1500 and DTS guide 1100 may be decoupled and removed from the patient, the awl sleeve 130 may be moved to the locked position in order to prevent the flexible awl tool 100 from bending, and a second and third incision may be made in the patient in order to approach the first and second fastener channels 331, 332 of the intervertebral spacer 300 via the second and third incisions with the flexible awl tool 100 in its straight configuration in order to drill the bone tunnels.

Figure 18:
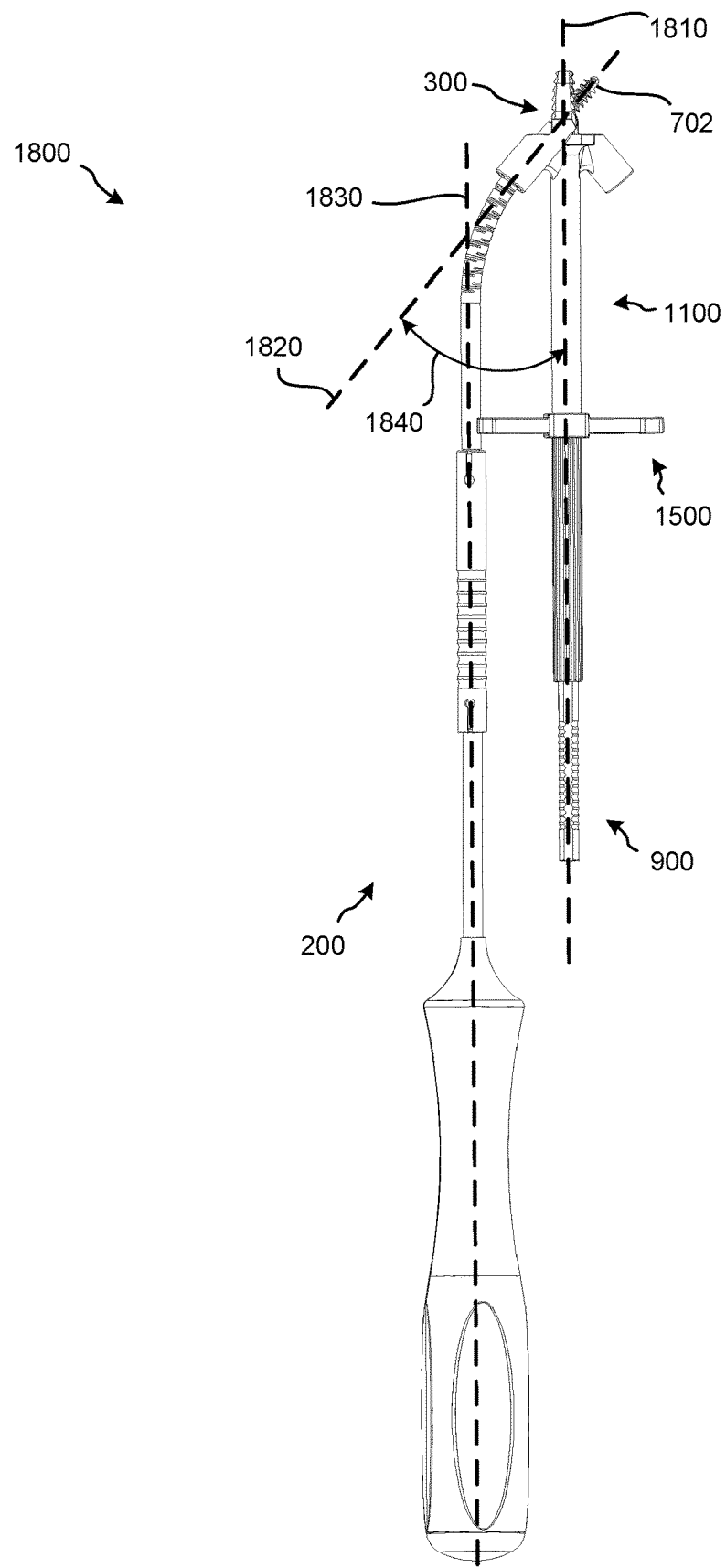
FIG. 18 illustrates an insertion assembly including the inserter tool, the intervertebral spacer, the bone screw, the DTS guide, the U-support tool, and the driver tool.

FIG. 18 illustrates an insertion assembly 1800 including the inserter tool 900, the intervertebral spacer 300, the DTS guide 1100, the U-support tool 1500, and the flexible driver tool 200 assembled together in order to drive bone screws 701, 702 into vertebral bodies (not shown) adjacent the intervertebral spacer 300. The driver engagement feature 240 of the flexible driver tool 200 can be any suitable style (e.g., Torx, hex, etc.) and can include the ability to retainably couple the bone screws 701, 702 (e.g., via a magnetic coupling, a mechanical coupling such as a tapered surface, etc.). The driver engagement feature 240 of the flexible driver tool 200 can be guided by the DTS guide 1100 through the first and second guide channels 1121, 1122. The driver depth stop ring 250 (or a surface of the bone screws 701, 702) may abut the first and second depth stops 333, 334 formed in the intervertebral spacer 300 to control the depth of the bone screws 701, 702 into the vertebral bodies. The surgeon may also utilize the U-support tool 1500 to help guide the flexible driver shaft 210 of the flexible driver tool 200. For example, the surgeon may press the flexible driver shaft 210 of the flexible driver tool 200 against the U-support tool 1500 while he/she rotates the flexible driver tool 200 and drives the bone screws 701, 702 into the vertebral bodies. In this manner, a proximal portion the flexible driver shaft 210 may likewise remain closer to the inserter tool shaft 910 and/or the DTS guide shaft 1110 such that a smaller incision may be utilized during the surgical procedure.

In at least one embodiment, the driver engagement feature 240 may be configured to be received through the first DTS guide channel 1121 at the first angle 711 and the second DTS guide channel 1122 at the second angle 712. Moreover, at least a portion of the flexible driver shaft 210 adjacent the first or second DTS guide members 1101, 1102 may be configured to flex while the driver engagement feature 240 is received through the first or second DTS guide channels 1121, 1122. Additionally, the driver engagement feature 240 received through the first or second DTS guide channels 1121, 1122 at the first or second angles 711, 712 may be at a greater absolute angle 1840 relative to the DTS guide shaft 1110 than a proximal portion of the flexible driver shaft 210. For example, FIG. 18 illustrates a DTS guide longitudinal axis 1810, a driver engagement feature longitudinal axis 1820, and a flexible driver tool longitudinal axis 1830. Note how the absolute angle 1840 formed between the DTS guide longitudinal axis 1810 and the driver engagement feature longitudinal axis 1820 is greater than an angle formed between a proximal portion of the flexible driver shaft 210 that lies along the flexible driver tool longitudinal axis 1830 and the DTS guide longitudinal axis 1810.

In at least one embodiment, a proximal portion of the flexible driver shaft 210 may be substantially parallel to the inserter tool shaft 910 and/or substantially parallel to the DTS guide shaft 1110 while the driver engagement feature 240 is received through the first or second DTS guide channels 1121, 1122 at the first or second angles 711, 712.

In at least one embodiment, a proximal portion of the flexible driver shaft 210 may remain substantially parallel to the DTS guide shaft 1110 as the flexible driver shaft 210 is rotated about the flexible driver tool longitudinal axis 1830.

In at least one embodiment, the U-support tool 1500 may be coupled to the DTS guide shaft 1110 and configured to guide the flexible driver shaft 210 as it is rotated about the flexible driver tool longitudinal axis 1830 in order to maintain a proximal portion of the flexible driver shaft 210 substantially parallel to the DTS guide shaft 1110 as the flexible driver shaft 210 is rotated about the flexible driver tool longitudinal axis 1830.

However, it will also be understood that in an alternative surgical procedure, the U-support tool 1500 and the DTS guide 1100 may be decoupled and removed from the patient, the driver sleeve 230 may be moved to the locked position in order to prevent the flexible driver tool 200 from bending, and a second and third incision may be made in the patient in order to approach the first and second fastener channels 331, 332 of the intervertebral spacer 300 via the second and third incisions with the flexible driver tool 200 in its straight configuration in order to drive the bone screws 701, 702 into the vertebral bodies.

Figure 19:
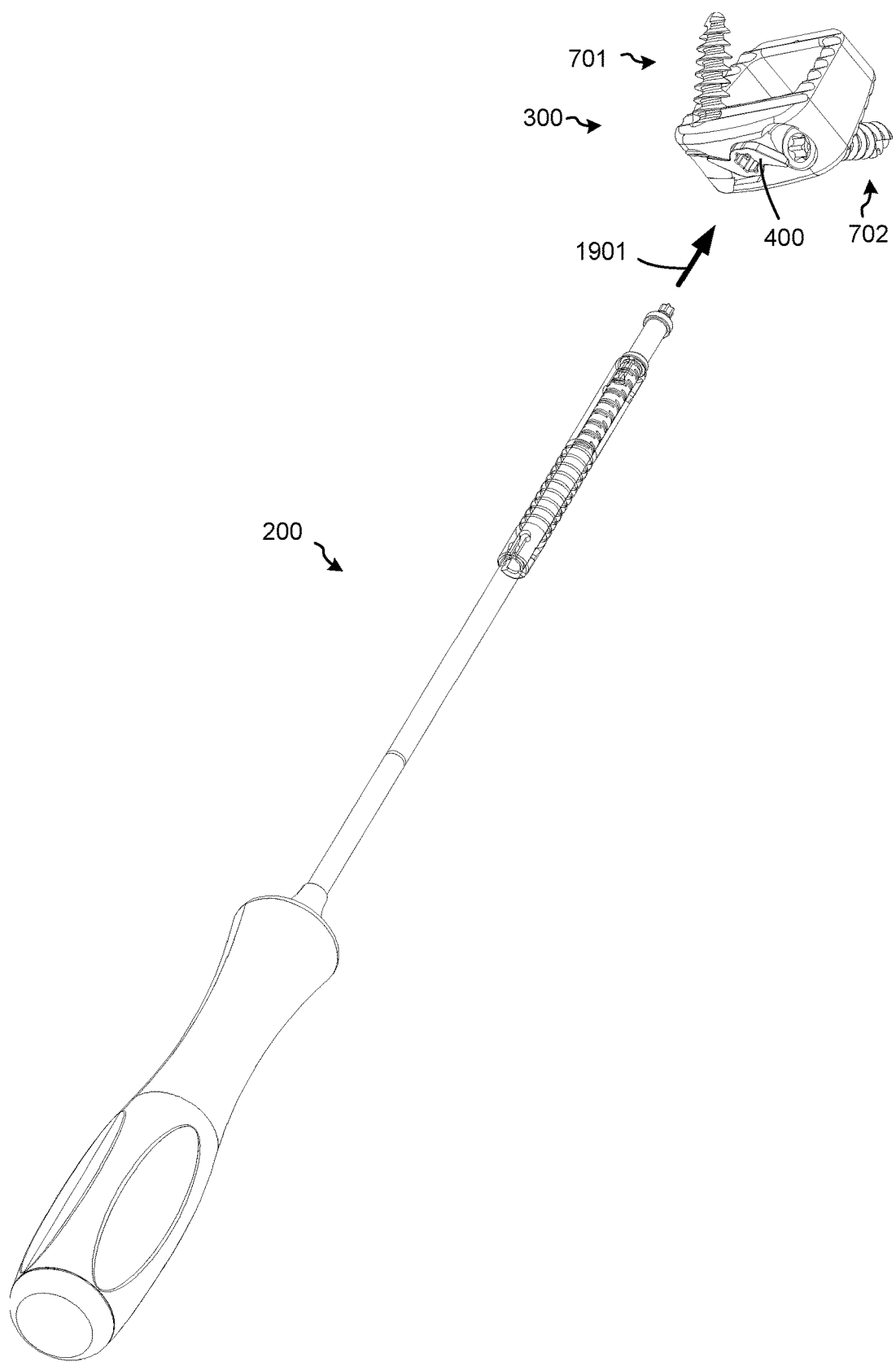
FIG. 19 illustrates the driver tool of FIG. 2A coupling with the locking member to rotate the locking member to a locked position and prevent the bone screws from backing out of the intervertebral spacer.

Once the bone screws have been properly placed into the vertebral bodies adjacent the intervertebral spacer 300, the surgeon may remove all of the tools from the patient in preparation for the next step of the procedure. In this step, the driver sleeve 230 may be moved distally to prevent the flexible driver tool 200 from bending. FIG. 19 illustrates how the flexible driver tool 200 of FIG. 2A may be moved in the direction of arrow 1901 to couple with the locking member 400 and rotate the locking member 400 between an unlocked position and a locked position in order to prevent the bone screws 701, 702 from backing out of the intervertebral spacer 300. A tactile and/or audible "click" may be felt and/or heard by the surgeon when the locking member 400 reaches the unlocked and/or locked positions.

Figure 20:
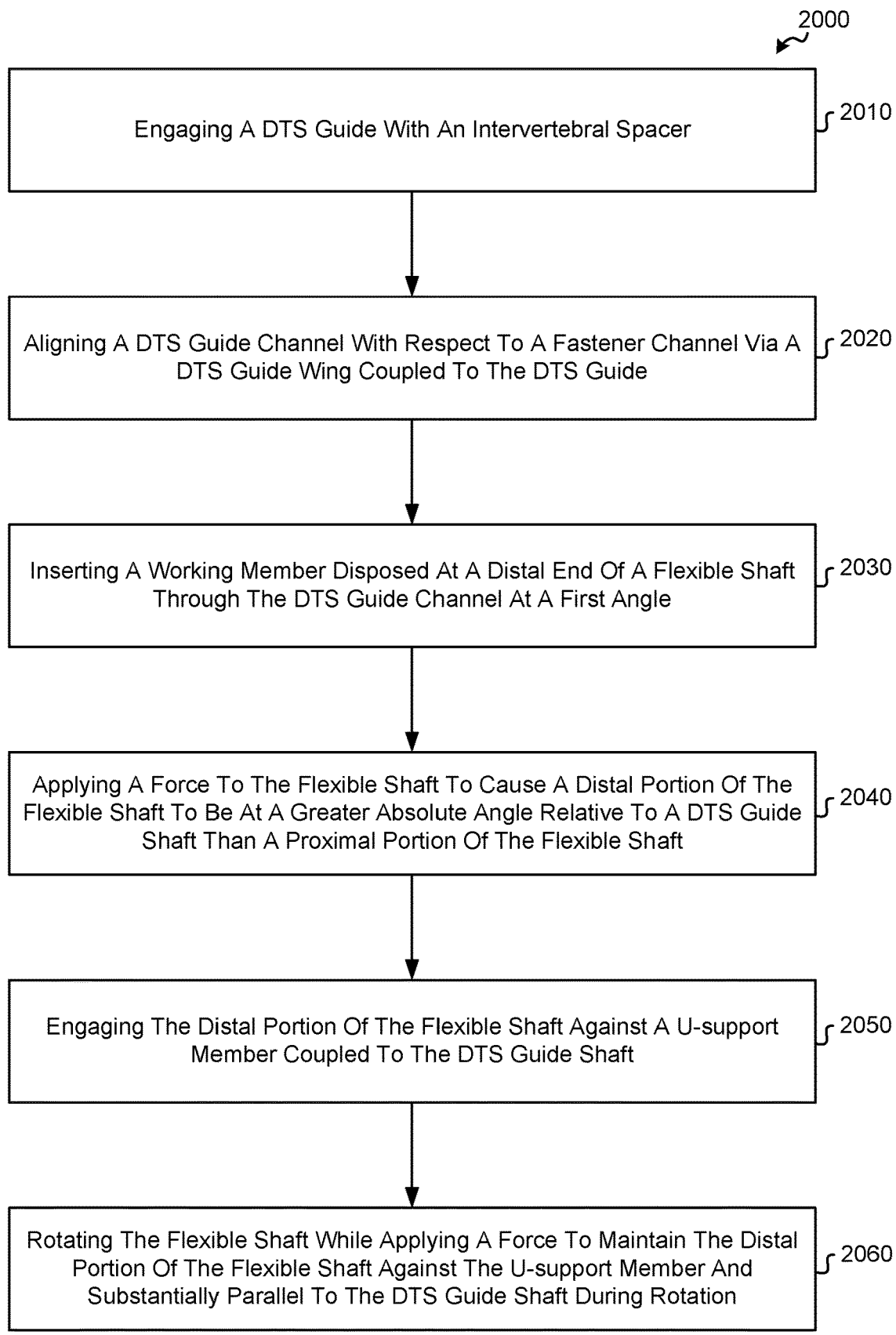
FIG. 20 illustrates a flowchart of a method for implanting an intervertebral spacer between two vertebral bodies of a patient, according to an embodiment of the present disclosure.

FIG. 20 illustrates a flowchart of a method 2000 for implanting an intervertebral spacer between two vertebral bodies of a patient, according to an embodiment of the present disclosure. In general, the method 2000 may include the use of an intervertebral spacer comprising a superior surface configured to engage a superior vertebral body, an inferior surface configured to engage an inferior vertebral body, and a peripheral wall extending from the superior surface to the inferior surface. The peripheral wall may comprise a fastener channel configured to receive a fastener, and the fastener channel may be oriented to pass through the peripheral wall and the superior or inferior surface of the intervertebral spacer at a first angle.

The method 2000 may begin with a step 2010 in which a DTS guide may engage the intervertebral spacer.

Once the DTS guide engages the intervertebral spacer, the method 2000 may proceed to a step 2020 in which a DTS guide channel of the DTS guide may be aligned with respect to the fastener channel of the intervertebral spacer via a DTS guide wing coupled to the DTS guide. The DTS guide wing may be configured to abut against a surface of the peripheral wall to align the DTS guide channel with respect to the fastener channel at the first angle in order to guide the fastener through the DTS guide channel and into the fastener channel of the intervertebral spacer.

Once the DTS guide channel has been aligned with respect to the fastener channel of the intervertebral spacer, the method 2000 may proceed to a step 2030 in which a working member disposed at a distal end of a flexible shaft of a flexible tool may be inserted through the DTS guide channel at the first angle.

Once the working member has been inserted through the DTS guide channel at the first angle, the method 2000 may proceed to a step 2040 in which a force may be applied to the flexible shaft to cause at least a portion of the flexible shaft adjacent the DTS guide channel to flex, such that a distal portion of the flexible shaft is at a greater absolute angle relative to a DTS guide shaft than a proximal portion of the flexible shaft.

Alternatively, or in addition thereto, the method 2000 may also include any one or more of the following steps, which may be performed in any order: (1) a step 2050 in which the distal portion of the flexible shaft may be engaged against a U-support member coupled to the DTS guide shaft; and (2) a step 2060 in which the flexible shaft may be rotated about a longitudinal axis of the flexible shaft while a force is applied to maintain the distal portion of the flexible shaft against the U-support member as the flexible shaft is rotated, such that the distal portion of the flexible shaft remains substantially parallel to the DTS guide shaft as the flexible shaft is rotated.

Any methods disclosed herein comprise one or more steps or actions for performing the described method. One or more of the method steps and/or actions may be omitted from and of the methods disclosed herein. Moreover, any of the method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

As defined herein, "substantially equal to" means "equal to," or within about a + or −10% relative variance from one another.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the systems, methods, and devices disclosed herein.

What is claimed is:

1. An intervertebral spacer insertion system comprising:
    an intervertebral spacer comprising:
        a superior surface configured to engage a superior vertebral body;
        an inferior surface configured to engage an inferior vertebral body; and
        a proximal surface comprising:
            a first fastener channel configured to receive a first fastener, the first fastener channel oriented to pass through the proximal and superior surfaces of the intervertebral spacer at a first angle;
            a second fastener channel configured to receive a second fastener, the second fastener channel oriented to pass through the proximal and inferior surfaces of the intervertebral spacer at a second angle; and
            a locking member channel intermediate the first and second fastener channels, the locking member channel comprising a first engagement feature formed therein; and
    an insertion assembly comprising:
        an inserter tool comprising:
            an inserter tool shaft; and
            a second engagement feature formed on a distal end of the inserter tool shaft,
            wherein the second engagement feature is configured to engage the first engagement feature in order to removably couple the intervertebral spacer with the inserter tool;
        a DTS guide comprising:
            a DTS guide shaft;
            a DTS guide shaft lumen passing through the DTS guide shaft, the DTS guide shaft lumen configured to receive the inserter tool shaft therein and slidably couple the DTS guide with the inserter tool;
            a first DTS guide member having a first DTS guide channel configured to receive the first fastener at the first angle relative to the DTS guide shaft and guide the first fastener into the first fastener channel of the intervertebral spacer;
            a second DTS guide member having a second DTS guide channel configured to receive the second fastener at the second angle relative to the DTS guide shaft and guide the second fastener into the second fastener channel of the intervertebral spacer;
            a first DTS guide wing proximate the first DTS guide member, the first DTS guide wing configured to abut against a first surface of the intervertebral spacer; and
            a second DTS guide wing proximate the second DTS guide member, the second DTS guide wing configured to abut against a second surface of the intervertebral spacer,
            wherein, the first and second DTS guide wings are configured to align the first and second DTS guide channels with respect to the first and second fastener channels, independently of any additional apertures or recesses formed in the intervertebral spacer, in order to respectively guide the first and second fasteners through the first and second DTS guide channels and into the first and second fastener channels of the intervertebral spacer; and
        a flexible tool comprising:
            a flexible shaft; and
            a working member disposed at a distal end of the flexible shaft;
            wherein:
                the working member is configured to be received through the first DTS guide channel at the first angle and the second DTS guide channel at the second angle;
                at least a portion of the flexible shaft adjacent the first or second DTS guide members is configured to flex while the working member is received through the first or second DTS guide channels; and
                the working member received through the first or second DTS guide channels at the first or second angles is at a greater absolute angle relative to the DTS guide shaft than a proximal portion of the flexible shaft.

2. The intervertebral spacer insertion system of claim 1, wherein the proximal portion of the flexible shaft is substantially parallel to the DTS guide shaft while the working member is received through the first or second DTS guide channels at the first or second angles.

3. The intervertebral spacer insertion system of claim 1, wherein the flexible shaft comprises a plurality of slots formed in at least a portion of the flexible shaft, the plurality of slots configured to permit at least a portion of the flexible shaft to flex away from a longitudinal axis of the flexible shaft.

4. The intervertebral spacer insertion system of claim 3, wherein the proximal portion of the flexible shaft remains substantially parallel to the DTS guide shaft as the flexible shaft is rotated about the longitudinal axis.

5. The intervertebral spacer insertion system of claim 4, further comprising a U-support tool coupled to the DTS guide shaft and configured to guide the flexible shaft as it is rotated about the longitudinal axis in order to maintain the proximal portion of the flexible shaft substantially parallel to the DTS guide shaft as the flexible shaft is rotated about the longitudinal axis.

6. The intervertebral spacer insertion system of claim 1, wherein:
    the flexible tool further comprises a sleeve slidably coupled to the flexible shaft and configured to move between a locked position and an unlocked position, wherein:

in the locked position, the sleeve prevents flexion of the flexible shaft; and in the unlocked position, the sleeve allows flexion of the flexible shaft;

the sleeve comprises:
  a first ridge disposed at a proximal end of the sleeve; and
  a second ridge disposed at a distal end of the sleeve; and the flexible shaft comprises:
  a first notch;
  a second notch; and
  a third notch,
  wherein:
    in the unlocked position, the first ridge is received within the first notch and the second ridge is received within the second notch, and
    in the locked position, the first ridge is received within the second notch and the second ridge is received within the third notch.

7. The intervertebral spacer insertion system of claim 1, wherein the working member comprises at least one of:
  a drill tip;
  an awl tip; and
  a driver engagement feature.

8. An insertion assembly configured to insert an intervertebral spacer between two vertebral bodies of a patient, the intervertebral spacer comprising a superior surface configured to engage a superior vertebral body, an inferior surface configured to engage an inferior vertebral body, and a peripheral wall extending from the superior surface to the inferior surface, the peripheral wall comprising a fastener channel configured to receive a fastener, the fastener channel oriented to pass through the peripheral wall and the superior or inferior surface of the intervertebral spacer at a first angle, the insertion assembly comprising:
  a DTS guide comprising:
    a DTS guide shaft;
    a DTS guide member coupled to a distal end of the DTS guide shaft; and
    a DTS guide channel formed through the DTS guide member at the first angle relative to the DTS guide shaft and configured to receive the fastener therethrough,
    wherein the DTS guide is configured to engage the intervertebral spacer and align the DTS guide channel with the fastener channel at the first angle; and
  a flexible tool comprising:
    a flexible shaft; and
    a working member disposed at a distal end of the flexible shaft;
    wherein:
      the working member is configured to be received through the DTS guide channel at the first angle;
      at least a portion of the flexible shaft adjacent the DTS guide member is configured to flex while the working member is received through the DTS guide channel; and
      a distal portion of the flexible shaft is at a greater absolute angle relative to the DTS guide shaft than a proximal portion of the flexible shaft.

9. The insertion assembly of claim 8, wherein the proximal portion of the flexible shaft is substantially parallel to the DTS guide shaft while the working member is received through the DTS guide channel at the first angle.

10. The insertion assembly of claim 8, wherein the flexible shaft comprises a plurality of slots formed in at least a portion of the flexible shaft, the plurality of slots configured to permit at least a portion of the flexible shaft to flex away from a longitudinal axis of the flexible shaft.

11. The insertion assembly of claim 10, wherein the proximal portion of the flexible shaft remains substantially parallel to the DTS guide shaft as the flexible shaft is rotated about the longitudinal axis.

12. The insertion assembly of claim 11, further comprising a U-support tool coupled to the DTS guide shaft and configured to guide the flexible shaft as it is rotated about the longitudinal axis in order to maintain the proximal portion of the flexible shaft substantially parallel to the DTS guide shaft as the flexible shaft is rotated about the longitudinal axis.

13. The insertion assembly of claim 8, wherein the flexible tool further comprises a sleeve slidably coupled to the flexible shaft and configured to move between a locked position and an unlocked position, wherein:
  in the locked position, the sleeve prevents flexion of the flexible shaft; and
  in the unlocked position, the sleeve allows flexion of the flexible shaft.

14. The insertion assembly of claim 13, wherein:
  the sleeve comprises:
    a first ridge disposed at a proximal end of the sleeve; and
    a second ridge disposed at a distal end of the sleeve; and
  the flexible shaft comprises:
    a first notch;
    a second notch; and
    a third notch,
    wherein:
      in the unlocked position, the first ridge is received within the first notch and the second ridge is received within the second notch, and
      in the locked position, the first ridge is received within the second notch and the second ridge is received within the third notch.

15. The insertion assembly of claim 8, wherein the working member comprises at least one of:
  a drill tip;
  an awl tip; and
  a driver engagement feature.

16. The insertion assembly of claim 8, wherein:
  the intervertebral spacer further comprises a locking member channel adjacent the fastener channel and comprising a first engagement feature;
  the insertion assembly further comprises an inserter tool, the inserter tool comprising:
    an inserter tool shaft; and
    a second engagement feature formed on a distal end of the inserter tool shaft,
    wherein the second engagement feature is configured to engage the first engagement feature of the locking member channel to removably couple the intervertebral spacer with the inserter tool; and
  the DTS guide further comprises:
    a DTS guide shaft lumen passing through the DTS guide shaft and configured to receive the inserter tool shaft therein to slidably couple the DTS guide to the inserter tool; and
    a DTS guide wing proximate the DTS guide member, the DTS guide wing configured to abut against a surface of the peripheral wall and align the DTS guide channel with respect to the fastener channel in order to guide the fastener through the DTS guide channel and into the fastener channel of the intervertebral spacer.

17. A method of implanting an intervertebral spacer between two vertebral bodies of a patient, the intervertebral spacer comprising a superior surface configured to engage a superior vertebral body, an inferior surface configured to engage an inferior vertebral body, and a peripheral wall extending from the superior surface to the inferior surface, the peripheral wall comprising a fastener channel configured to receive a fastener, the fastener channel oriented to pass through the peripheral wall and the superior or inferior surface of the intervertebral spacer at a first angle, the method comprising:

engaging a DTS guide with the intervertebral spacer;

aligning a DTS guide channel of the DTS guide with respect to the fastener channel of the intervertebral spacer via a DTS guide wing coupled to the DTS guide, the DTS guide wing configured to abut against a surface of the peripheral wall and align the DTS guide channel with respect to the fastener channel at the first angle in order to guide the fastener through the DTS guide channel and into the fastener channel of the intervertebral spacer;

inserting a working member disposed at a distal end of a flexible shaft of a flexible tool through the DTS guide channel at the first angle; and applying a force to the flexible shaft to cause at least a portion of the flexible shaft adjacent the DTS guide channel to flex, such that a distal portion of the flexible shaft is at a greater absolute angle relative to a DTS guide shaft than a proximal portion of the flexible shaft.

18. The method of claim 17, further comprising:

engaging the distal portion of the flexible shaft against a U-support member coupled to the DTS guide shaft; and rotating the flexible shaft about a longitudinal axis of the flexible shaft, while applying a force to maintain the distal portion of the flexible shaft against the U-support member as the flexible shaft is rotated, such that the distal portion of the flexible shaft remains substantially parallel to the DTS guide shaft as the flexible shaft is rotated.

19. The method of claim 17, wherein the working member comprises an awl tip, the method further comprising:

drilling a bone tunnel in a vertebral body of the patient with the awl tip guided through the DTS guide channel, through the fastener channel of the intervertebral spacer, and into the vertebral body of the patient.

20. The method of claim 17, wherein the working member comprises a driver engagement feature, the method further comprising:

driving a bone screw into a vertebral body of the patient with the driver engagement feature coupled to the bone screw and guided through the DTS guide channel and into the fastener channel of the intervertebral spacer.

* * * * *